United States Patent [19]
Lemke et al.

[11] Patent Number: 5,811,516
[45] Date of Patent: Sep. 22, 1998

[54] TYRO-3 PROTEIN TYROSINE KINASE

[75] Inventors: Greg E. Lemke, Del Mar; Cary H. C. Lai, La Jolla, both of Calif.

[73] Assignee: The Salk Institute for Biological Studies, San Diego, Calif.

[21] Appl. No.: 456,647

[22] Filed: Jun. 2, 1995

Related U.S. Application Data

[62] Division of Ser. No. 237,401, May 2, 1994, which is a continuation of Ser. No. 884,486, May 15, 1992, abandoned.

[51] Int. Cl.$^6$ .................. C07K 14/00; C07K 14/705
[52] U.S. Cl. ................... 530/350; 530/300; 435/6; 435/240.1; 435/240.2; 435/172.3
[58] Field of Search ................... 530/350, 300; 435/6, 240.1, 240.2, 172.3

[56] References Cited

U.S. PATENT DOCUMENTS 5,447,860  9/1995  Ziegler .................. 435/240.1
5,468,634  11/1995  Liu ...................... 435/240.2

OTHER PUBLICATIONS

Lewis et al. (1995) Genovis 31: 13–19.
Ohashi et al. (1995) J. Biochem 117: 1267–75.
Schultz et al (1995) Brain Res MBR 28: 273–80.
Mark et al (1994) J. Biol. Chem 269: 10720–10728.
Dai et al. (1994) Oncogene 9: 975–979.
Fujimoto (1994) Oncogene 9: 693–698.
Crosier et. al (1994) Growth Factors 11: 125–136.
Lai et al. (1994) Oncogene 9: 2567–2878.

*Primary Examiner*—Stephen Walsh
*Assistant Examiner*—Kenneth A. Sorensen
*Attorney, Agent, or Firm*—Fish & Richardson P.C.

[57] ABSTRACT

A novel protein tyrosine kinase (PTK) designated tyro-3 is provided herein. Polynucleotides encoding tyro-3 are also provided. Tyro-3 is identified and characterized as being expressed in brain tissue.

4 Claims, 3 Drawing Sheets

SEQUENCE LISTING ( 1 ) GENERAL INFORMATION:

( i i i ) NUMBER OF SEQUENCES: 54

( 2 ) INFORMATION FOR SEQ ID NO:1:

( i ) SEQUENCE CHARACTERISTICS:
        ( A ) LENGTH: 165 base pairs
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE:
        ( B ) CLONE: Tyro-1

( i x ) FEATURE:
        ( A ) NAME/KEY: CDS
        ( B ) LOCATION: 1..165

( x i ) SEQUENCE DESCRIPTION: SEQ ID NO:1:

```
AAC  ATT  CTG  GTA  AAC  AGC  AAC  TTG  GTC  TGC  AAG  GTG  TCT  GAT  TTC  GGC          48
Asn  Ile  Leu  Val  Asn  Ser  Asn  Leu  Val  Cys  Lys  Val  Ser  Asp  Phe  Gly
 1                    5                        10                       15

ATG  TCC  AGG  GTG  CTT  GAG  GAT  GAC  CCG  GAA  GCA  GCC  TAT  ACT  ACC  AGG          96
Met  Ser  Arg  Val  Leu  Glu  Asp  Asp  Pro  Glu  Ala  Ala  Tyr  Thr  Thr  Arg
               20                       25                       30

GGC  GGC  AAG  ATT  CCC  ATC  CGG  TGG  ACT  GCA  CCA  GAA  GCA  ATT  GCG  TAT         144
```

```
                        Gly  Gly  Lys  Ile  Pro  Ile  Arg  Trp  Thr  Ala  Pro  Glu  Ala  Ile  Ala  Tyr
                                   35                      40                      45

CGT  AAA  TTT  ACC  TCA  GCC  AGT                                                                              165
Arg  Lys  Phe  Thr  Ser  Ala  Ser
      50                      55
```

( 2 ) INFORMATION FOR SEQ ID NO:2:

( i ) SEQUENCE CHARACTERISTICS:
        ( A ) LENGTH: 55 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Asn  Ile  Leu  Val  Asn  Ser  Asn  Leu  Val  Cys  Lys  Val  Ser  Asp  Phe  Gly
 1                    5                     10                     15

Met  Ser  Arg  Val  Leu  Glu  Asp  Asp  Pro  Glu  Ala  Ala  Tyr  Thr  Thr  Arg
               20                     25                     30

Gly  Gly  Lys  Ile  Pro  Ile  Arg  Trp  Thr  Ala  Pro  Glu  Ala  Ile  Ala  Tyr
               35                     40                     45

Arg  Lys  Phe  Thr  Ser  Ala  Ser
      50                     55
```

( 2 ) INFORMATION FOR SEQ ID NO:3:

( i ) SEQUENCE CHARACTERISTICS:
        ( A ) LENGTH: 2437 base pairs
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE:
        ( B ) CLONE: Tyro-2

( i x ) FEATURE:
        ( A ) NAME/KEY: CDS
        ( B ) LOCATION: 3..2118

( x i ) SEQUENCE DESCRIPTION: SEQ ID NO:3:

```
CA  AAC  TGT  GTG  GAG  AAA  TGT  CCA  GAT  GGC  CTA  CAG  GGA  GCA  AAC  AGT        47
    Asn  Cys  Val  Glu  Lys  Cys  Pro  Asp  Gly  Leu  Gln  Gly  Ala  Asn  Ser
     1                    5                     10                     15

TTC  ATT  TTT  AAG  TAT  GCA  GAT  CAG  GAT  CGG  GAG  TGC  CAC  CCT  TGC  CAT       95
Phe  Ile  Phe  Lys  Tyr  Ala  Asp  Gln  Asp  Arg  Glu  Cys  His  Pro  Cys  His
               20                     25                     30

CCA  AAC  TGC  ACC  CAG  GGG  TGT  AAC  GGT  CCC  ACT  AGT  CAT  GAC  TGC  ATT      143
Pro  Asn  Cys  Thr  Gln  Gly  Cys  Asn  Gly  Pro  Thr  Ser  His  Asp  Cys  Ile
               35                     40                     45

TAC  TAC  CCA  TGG  ACG  GGC  CAT  TCC  ACT  TTA  CCA  CAA  CAC  GCT  AGA  ACT      191
Tyr  Tyr  Pro  Trp  Thr  Gly  His  Ser  Thr  Leu  Pro  Gln  His  Ala  Arg  Thr
               50                     55                     60

CCA  CTG  ATT  GCA  GCC  GGA  GTC  ATT  GGA  GGC  CTC  TTC  ATC  CTG  GTG  ATC      239
Pro  Leu  Ile  Ala  Ala  Gly  Val  Ile  Gly  Gly  Leu  Phe  Ile  Leu  Val  Ile
      65                     70                     75

ATG  GCT  TTG  ACA  TTT  GCT  GTC  TAT  GTC  AGA  AGA  AAG  AGC  ATC  AAA  AAG      287
Met  Ala  Leu  Thr  Phe  Ala  Val  Tyr  Val  Arg  Arg  Lys  Ser  Ile  Lys  Lys
 80                    85                     90                     95

AAA  CGT  GCT  TTG  AGG  AGA  TTC  CTG  GAG  ACA  GAG  CTG  GTA  GAG  CCC  TTA      335
Lys  Arg  Ala  Leu  Arg  Arg  Phe  Leu  Glu  Thr  Glu  Leu  Val  Glu  Pro  Leu
               100                    105                    110

ACT  CCC  AGT  GGC  ACG  GCA  CCC  AAT  CAA  GCT  CAA  CTT  CGC  ATT  TTG  AAG      383
```

```
Thr  Pro  Ser  Gly  Thr  Ala  Pro  Asn  Gln  Ala  Gln  Leu  Arg  Ile  Leu  Lys
          115            120                      125

GAA  ACC  GAA  CTA  AAG  AGG  GTA  AAG  GTC  CTT  GGC  TCG  GGA  GCT  TTT  GGA      431
Glu  Thr  Glu  Leu  Lys  Arg  Val  Lys  Val  Leu  Gly  Ser  Gly  Ala  Phe  Gly
          130                      135                      140

ACC  GTT  TAT  AAA  GGT  ATT  TGG  GTG  CCT  GAA  GGT  GAA  ACA  GTG  AAA  ATC      479
Thr  Val  Tyr  Lys  Gly  Ile  Trp  Val  Pro  Glu  Gly  Glu  Thr  Val  Lys  Ile
          145                      150                      155

CCT  GTG  GCT  ATA  AAG  ATC  CTC  AAT  GAA  ACA  ACT  GGC  CCC  AAA  GCC  AAC      527
Pro  Val  Ala  Ile  Lys  Ile  Leu  Asn  Glu  Thr  Thr  Gly  Pro  Lys  Ala  Asn
160                      165                      170                      175

GTG  GAG  TTC  ATG  GAT  GAG  GCT  CTG  ATC  ATG  GCA  AGT  ATG  GAT  CAC  CCA      575
Val  Glu  Phe  Met  Asp  Glu  Ala  Leu  Ile  Met  Ala  Ser  Met  Asp  His  Pro
                    180                      185                      190

CAC  CTA  GTT  CGC  CTA  TTG  GGA  GTG  TGT  CTA  AGT  CCC  ACT  ATC  CAG  TTG      623
His  Leu  Val  Arg  Leu  Leu  Gly  Val  Cys  Leu  Ser  Pro  Thr  Ile  Gln  Leu
                    195                      200                      205

GTT  ACG  CAG  CTG  ATG  CCG  CAT  GCG  TGC  CTA  CTG  GAC  TAT  GTT  CAT  GAA      671
Val  Thr  Gln  Leu  Met  Pro  His  Ala  Cys  Leu  Leu  Asp  Tyr  Val  His  Glu
          210                      215                      220

CAC  AAG  GAT  AAC  ATT  GGA  TCA  CAG  CTG  CTG  TTG  AAC  TGG  TGT  GTC  CAG      719
His  Lys  Asp  Asn  Ile  Gly  Ser  Gln  Leu  Leu  Leu  Asn  Trp  Cys  Val  Gln
          225                      230                      235

ATT  GCT  AAG  GGA  ATG  ATG  TAC  CTA  GAA  GAA  AGA  CGG  CTT  GTT  CAT  CGG      767
Ile  Ala  Lys  Gly  Met  Met  Tyr  Leu  Glu  Glu  Arg  Arg  Leu  Val  His  Arg
240                      245                      250                      255

GAT  CTG  GCA  GCC  CGC  AAT  GTC  TTA  GTG  AAA  TCT  CCA  AAT  CAT  GTT  AAA      815
Asp  Leu  Ala  Ala  Arg  Asn  Val  Leu  Val  Lys  Ser  Pro  Asn  His  Val  Lys
                    260                      265                      270

ATC  ACA  GAT  TTT  GGA  CTG  GCC  CGG  CTC  TTG  GAA  GGA  GAT  GAA  AAA  GAA      863
Ile  Thr  Asp  Phe  Gly  Leu  Ala  Arg  Leu  Leu  Glu  Gly  Asp  Glu  Lys  Glu
                    275                      280                      285

TAC  AAT  GCT  GAT  GGT  GGC  AAG  ATG  CCA  ATT  AAA  TGG  ATG  GCT  CTG  GAA      911
Tyr  Asn  Ala  Asp  Gly  Gly  Lys  Met  Pro  Ile  Lys  Trp  Met  Ala  Leu  Glu
          290                      295                      300

TGT  ATA  CAT  TAT  AGG  AAA  TTC  ACA  CAT  CAA  AGT  GAT  GTT  TGG  AGC  TAT      959
Cys  Ile  His  Tyr  Arg  Lys  Phe  Thr  His  Gln  Ser  Asp  Val  Trp  Ser  Tyr
     305                      310                      315

GGC  GTC  ACT  ATA  TGG  GAA  CTG  ATG  ACC  TTT  GGA  GGA  AAG  CCC  TAT  GAT     1007
Gly  Val  Thr  Ile  Trp  Glu  Leu  Met  Thr  Phe  Gly  Gly  Lys  Pro  Tyr  Asp
320                      325                      330                      335

GGA  ATT  CCA  ACC  CGA  GAA  ATC  CCC  GAT  TTA  CTG  GAG  AAA  GGA  GAG  CGT     1055
Gly  Ile  Pro  Thr  Arg  Glu  Ile  Pro  Asp  Leu  Leu  Glu  Lys  Gly  Glu  Arg
                    340                      345                      350

CTG  CCT  CAG  CCT  CCC  ATC  TGC  ACT  ATT  GAT  GTT  TAC  ATG  GTC  ATG  GTC     1103
Leu  Pro  Gln  Pro  Pro  Ile  Cys  Thr  Ile  Asp  Val  Tyr  Met  Val  Met  Val
               355                      360                      365

AAA  TGT  TGG  ATG  ATC  GAT  GCT  GAC  AGC  AGA  CCT  AAA  TTC  AAA  GAA  CTG     1151
Lys  Cys  Trp  Met  Ile  Asp  Ala  Asp  Ser  Arg  Pro  Lys  Phe  Lys  Glu  Leu
          370                      375                      380

GCT  GCT  GAG  TTT  TCA  AGA  ATG  GCT  AGA  GAC  CCT  CAA  AGA  TAC  CTA  GTT     1199
Ala  Ala  Glu  Phe  Ser  Arg  Met  Ala  Arg  Asp  Pro  Gln  Arg  Tyr  Leu  Val
          385                      390                      395

ATT  CAG  GGT  GAT  GAT  CGT  ATG  AAG  CTT  CCC  AGT  CCA  AAT  GAC  AGC  AAA     1247
Ile  Gln  Gly  Asp  Asp  Arg  Met  Lys  Leu  Pro  Ser  Pro  Asn  Asp  Ser  Lys
400                      405                      410                      415

TTC  TTC  CAG  AAT  CTC  TTG  GAT  GAA  GAG  GAT  TTG  GAA  GAC  ATG  ATG  GAT     1295
Phe  Phe  Gln  Asn  Leu  Leu  Asp  Glu  Glu  Asp  Leu  Glu  Asp  Met  Met  Asp
                    420                      425                      430

GCT  GAG  GAA  TAT  TTG  GTC  CCC  CAG  GCT  TTC  AAC  ATA  CCT  CCT  CCC  ATC     1343
```

```
Ala Glu Glu Tyr Leu Val Pro Gln Ala Phe Asn Ile Pro Pro Pro Ile
        435                 440                 445

TAC ACA TCC AGA ACA AGA ATT GAC TCC AAT AGG AAT CAG TTT GTG TAC    1391
Tyr Thr Ser Arg Thr Arg Ile Asp Ser Asn Arg Asn Gln Phe Val Tyr
        450                 455                 460

CAA GAT GGG GGC TTT GCT ACA CAA CAA GGA ATG CCC ATG CCC TAC AGA    1439
Gln Asp Gly Gly Phe Ala Thr Gln Gln Gly Met Pro Met Pro Tyr Arg
        465                 470                 475

GCC ACA ACC AGC ACC ATA CCA GAG GCT CCA GTA GCT CAG GGT GCA ACG    1487
Ala Thr Thr Ser Thr Ile Pro Glu Ala Pro Val Ala Gln Gly Ala Thr
480                 485                 490                 495

GCT GAG ATG TTT GAT GAC TCC TGC TGT AAT GGT ACC CTA CGA AAG CCA    1535
Ala Glu Met Phe Asp Asp Ser Cys Cys Asn Gly Thr Leu Arg Lys Pro
                    500                 505                 510

GTG GCA CCC CAT GTC CAA GAG GAC AGT AGC ACT CAG AGG TAT AGT GCT    1583
Val Ala Pro His Val Gln Glu Asp Ser Ser Thr Gln Arg Tyr Ser Ala
                515                 520                 525

GAT CCC ACA GTG TTC GCC CCA GAA CGG AAT CCT CGA GGA GAA CTG GAT    1631
Asp Pro Thr Val Phe Ala Pro Glu Arg Asn Pro Arg Gly Glu Leu Asp
            530                 535                 540

GAA GAA GGC TAC ATG ACT CCA ATG CAT GAC AAG CCC AAA CAA GAA TAT    1679
Glu Glu Gly Tyr Met Thr Pro Met His Asp Lys Pro Lys Gln Glu Tyr
        545                 550                 555

CTG AAT CCT GTG GAA GAG AAC CCT TTT GTG TCC CGA AGG AAG AAT GGA    1727
Leu Asn Pro Val Glu Glu Asn Pro Phe Val Ser Arg Arg Lys Asn Gly
560                 565                 570                 575

GAT CTT CAA GCT TTA GAT AAT CCG GAG TAT CAC AGT GCT TCC AGC GGT    1775
Asp Leu Gln Ala Leu Asp Asn Pro Glu Tyr His Ser Ala Ser Ser Gly
                    580                 585                 590

CCA CCC AAG GCG GAG GAT GAA TAC GTG AAT GAG CCT CTA TAC CTC AAC    1823
Pro Pro Lys Ala Glu Asp Glu Tyr Val Asn Glu Pro Leu Tyr Leu Asn
                595                 600                 605

ACC TTC GCC AAT GCC TTG GGG AGT GCA GAG TAC ATG AAA AAC AGT GTA    1871
Thr Phe Ala Asn Ala Leu Gly Ser Ala Glu Tyr Met Lys Asn Ser Val
            610                 615                 620

CTG TCT GTG CCA GAG AAA GCC AAG AAA GCA TTT GAC AAC CCC GAC TAC    1919
Leu Ser Val Pro Glu Lys Ala Lys Lys Ala Phe Asp Asn Pro Asp Tyr
        625                 630                 635

TGG AAC CAC AGC CTG CCA CCC CGG AGC ACC CTT CAG CAC CCA GAC TAC    1967
Trp Asn His Ser Leu Pro Pro Arg Ser Thr Leu Gln His Pro Asp Tyr
640                 645                 650                 655

CTG CAG GAA TAC AGC ACA AAA TAT TTT TAT AAA CAG AAT GGA CGG ATC    2015
Leu Gln Glu Tyr Ser Thr Lys Tyr Phe Tyr Lys Gln Asn Gly Arg Ile
                    660                 665                 670

CGC CCC ATT GTG GCA GAG AAT CCT GAG TAC CTC TCG GAG TTC TCG CTG    2063
Arg Pro Ile Val Ala Glu Asn Pro Glu Tyr Leu Ser Glu Phe Ser Leu
                675                 680                 685

AAG CCT GGC ACT ATG CTG CCC CCT CCG CCC TAC AGA CAC CGG AAT ACT    2111
Lys Pro Gly Thr Met Leu Pro Pro Pro Pro Tyr Arg His Arg Asn Thr
            690                 695                 700

GTG GTG T GAGCTTGGCT AGAGTGTTAG GTGGAGAAAC ACACACCCAC TCCATTTCCC    2168
Val Val
705

TTCCCCCTCC TCTTTCTCTG GTGGTCTTCC TTCTTCTCCC AAGGCCAGTA GTTTGACAC    2228

TTCCAAGTGG AAGCAGTAGA GATGCAATGA TAGTTCTGTG CTTACCTAAC TTGAATATTA    2288

GAAGGAAAGA CTGAAAGAGA AAGACAGGGA TACACACACT GTTTCTTCGT TTCTTCATAT    2348

GGGTTGGTTA ACAGAGTGTC AAAGCTAGAG AAGGTCTAGG AAGTATAAGG CAATACTGCC    2408

TGCTGTCAAA GAGCCCCATC TTTCTTCTC                                     2437
```

( 2 ) INFORMATION FOR SEQ ID NO:4:

( i ) SEQUENCE CHARACTERISTICS:
        ( A ) LENGTH: 705 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Asn Cys Val Glu Lys Cys Pro Asp Gly Leu Gln Gly Ala Asn Ser Phe
  1               5                  10                  15

Ile Phe Lys Tyr Ala Asp Gln Asp Arg Glu Cys His Pro Cys His Pro
             20                  25                  30

Asn Cys Thr Gln Gly Cys Asn Gly Pro Thr Ser His Asp Cys Ile Tyr
         35                  40                  45

Tyr Pro Trp Thr Gly His Ser Thr Leu Pro Gln His Ala Arg Thr Pro
     50                  55                  60

Leu Ile Ala Ala Gly Val Ile Gly Leu Phe Ile Leu Val Ile Met
 65                  70                  75                  80

Ala Leu Thr Phe Ala Val Tyr Val Arg Arg Lys Ser Ile Lys Lys Lys
                 85                  90                  95

Arg Ala Leu Arg Arg Phe Leu Glu Thr Glu Leu Val Glu Pro Leu Thr
             100                 105                 110

Pro Ser Gly Thr Ala Pro Asn Gln Ala Gln Leu Arg Ile Leu Lys Glu
         115                 120                 125

Thr Glu Leu Lys Arg Val Lys Val Leu Gly Ser Gly Ala Phe Gly Thr
     130                 135                 140

Val Tyr Lys Gly Ile Trp Val Pro Glu Gly Glu Thr Val Lys Ile Pro
145                 150                 155                 160

Val Ala Ile Lys Ile Leu Asn Glu Thr Thr Gly Pro Lys Ala Asn Val
                 165                 170                 175

Glu Phe Met Asp Glu Ala Leu Ile Met Ala Ser Met Asp His Pro His
             180                 185                 190

Leu Val Arg Leu Leu Gly Val Cys Leu Ser Pro Thr Ile Gln Leu Val
         195                 200                 205

Thr Gln Leu Met Pro His Ala Cys Leu Leu Asp Tyr Val His Glu His
     210                 215                 220

Lys Asp Asn Ile Gly Ser Gln Leu Leu Leu Asn Trp Cys Val Gln Ile
225                 230                 235                 240

Ala Lys Gly Met Met Tyr Leu Glu Glu Arg Arg Leu Val His Arg Asp
                 245                 250                 255

Leu Ala Ala Arg Asn Val Leu Val Lys Ser Pro Asn His Val Lys Ile
             260                 265                 270

Thr Asp Phe Gly Leu Ala Arg Leu Leu Glu Gly Asp Glu Lys Glu Tyr
         275                 280                 285

Asn Ala Asp Gly Gly Lys Met Pro Ile Lys Trp Met Ala Leu Glu Cys
     290                 295                 300

Ile His Tyr Arg Lys Phe Thr His Gln Ser Asp Val Trp Ser Tyr Gly
305                 310                 315                 320

Val Thr Ile Trp Glu Leu Met Thr Phe Gly Lys Pro Tyr Asp Gly
                 325                 330                 335

Ile Pro Thr Arg Glu Ile Pro Asp Leu Leu Glu Lys Gly Glu Arg Leu
             340                 345                 350

Pro Gln Pro Pro Ile Cys Thr Ile Asp Val Tyr Met Val Met Val Lys
```

|  |  |  | 355 |  |  |  | 360 |  |  |  | 365 |  |  |
|---|---|---|---|---|---|---|---|---|---|---|---|---|---|
| Cys | Trp<br>370 | Met | Ile | Asp | Ala | Asp<br>375 | Ser | Arg | Pro | Lys | Phe<br>380 | Lys | Glu | Leu | Ala |
| Ala<br>385 | Glu | Phe | Ser | Arg | Met<br>390 | Ala | Arg | Asp | Pro | Gln<br>395 | Arg | Tyr | Leu | Val | Ile<br>400 |
| Gln | Gly | Asp | Asp | Arg<br>405 | Met | Lys | Leu | Pro | Ser<br>410 | Pro | Asn | Asp | Ser | Lys<br>415 | Phe |
| Phe | Gln | Asn | Leu<br>420 | Leu | Asp | Glu | Glu | Asp<br>425 | Leu | Glu | Asp | Met | Met<br>430 | Asp | Ala |
| Glu | Glu | Tyr<br>435 | Leu | Val | Pro | Gln | Ala<br>440 | Phe | Asn | Ile | Pro | Pro<br>445 | Pro | Ile | Tyr |
| Thr | Ser<br>450 | Arg | Thr | Arg | Ile | Asp<br>455 | Ser | Asn | Arg | Asn | Gln<br>460 | Phe | Val | Tyr | Gln |
| Asp<br>465 | Gly | Gly | Phe | Ala | Thr<br>470 | Gln | Gln | Gly | Met | Pro<br>475 | Met | Pro | Tyr | Arg | Ala<br>480 |
| Thr | Thr | Ser | Thr | Ile<br>485 | Pro | Glu | Ala | Pro | Val<br>490 | Ala | Gln | Gly | Ala | Thr<br>495 | Ala |
| Glu | Met | Phe | Asp<br>500 | Asp | Ser | Cys | Cys | Asn<br>505 | Gly | Thr | Leu | Arg | Lys<br>510 | Pro | Val |
| Ala | Pro | His<br>515 | Val | Gln | Glu | Asp | Ser<br>520 | Ser | Thr | Gln | Arg | Tyr<br>525 | Ser | Ala | Asp |
| Pro | Thr<br>530 | Val | Phe | Ala | Pro | Glu<br>535 | Arg | Asn | Pro | Arg | Gly<br>540 | Glu | Leu | Asp | Glu |
| Glu<br>545 | Gly | Tyr | Met | Thr | Pro<br>550 | Met | His | Asp | Lys | Pro<br>555 | Lys | Gln | Glu | Tyr | Leu<br>560 |
| Asn | Pro | Val | Glu | Glu<br>565 | Asn | Pro | Phe | Val | Ser<br>570 | Arg | Arg | Lys | Asn | Gly<br>575 | Asp |
| Leu | Gln | Ala | Leu<br>580 | Asp | Asn | Pro | Glu | Tyr<br>585 | His | Ser | Ala | Ser | Ser<br>590 | Gly | Pro |
| Pro | Lys | Ala<br>595 | Glu | Asp | Glu | Tyr | Val<br>600 | Asn | Glu | Pro | Leu | Tyr<br>605 | Leu | Asn | Thr |
| Phe | Ala<br>610 | Asn | Ala | Leu | Gly | Ser<br>615 | Ala | Glu | Tyr | Met | Lys<br>620 | Asn | Ser | Val | Leu |
| Ser<br>625 | Val | Pro | Glu | Lys | Ala<br>630 | Lys | Lys | Ala | Phe | Asp<br>635 | Asn | Pro | Asp | Tyr | Trp<br>640 |
| Asn | His | Ser | Leu | Pro<br>645 | Pro | Arg | Ser | Thr | Leu<br>650 | Gln | His | Pro | Asp | Tyr<br>655 | Leu |
| Gln | Glu | Tyr | Ser<br>660 | Thr | Lys | Tyr | Phe | Tyr<br>665 | Lys | Gln | Asn | Gly | Arg<br>670 | Ile | Arg |
| Pro | Ile | Val<br>675 | Ala | Glu | Asn | Pro | Glu<br>680 | Tyr | Leu | Ser | Glu | Phe<br>685 | Ser | Leu | Lys |
| Pro | Gly<br>690 | Thr | Met | Leu | Pro | Pro<br>695 | Pro | Pro | Tyr | Arg | His<br>700 | Arg | Asn | Thr | Val |
| Val<br>705 |  |  |  |  |  |  |  |  |  |  |  |  |  |  |  |

( 2 ) INFORMATION FOR SEQ ID NO:5:

( i ) SEQUENCE CHARACTERISTICS:
        ( A ) LENGTH: 3307 base pairs
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE:

-continued ( B ) CLONE: Tyro-3

( i x ) FEATURE:
    ( A ) NAME/KEY: CDS
    ( B ) LOCATION: 237..2859

( x i ) SEQUENCE DESCRIPTION: SEQ ID NO:5:

```
CGGCGGCGGC  GGCGGCTGTG  GAAGGAGCGC  GGTGGCCCAG  CCGCAGCCCC  GGGGACTCCT       60

CGCTGCTGAC  GGCGGTGGCC  GCGGCTCTAG  GCGGCCGCGG  GTCCGGGACG  CCCGGGCCGA      120

GCGCCGCCCC  CCGCCCCTCC  CGCGGGCCTC  CCGCCCCTCC  TCCGCCACCC  TCCTCTCTGC      180

GCTCGCGGGC  CGGGCCCGGC  ATGGTGCGGC  GTCGCCGCCG  ATGGCTGAGG  CGGAGC         236
```

| | | | | | | | | | | | | | | | | |
|---|---|---|---|---|---|---|---|---|---|---|---|---|---|---|---|---|
| ATG | GGG | TGG | CCG | GGG | CTC | CGG | CCG | CTG | CTG | CTG | GCG | GGA | CTG | GCT | TCT | 284 |
| Met | Gly | Trp | Pro | Gly | Leu | Arg | Pro | Leu | Leu | Leu | Ala | Gly | Leu | Ala | Ser | |
| 1 | | | | 5 | | | | | 10 | | | | | 15 | | |
| CTG | CTG | CTC | CCC | GGG | TCT | GCG | GCC | GCA | GGC | CTG | AAG | CTC | ATG | GGC | GCC | 332 |
| Leu | Leu | Leu | Pro | Gly | Ser | Ala | Ala | Ala | Gly | Leu | Lys | Leu | Met | Gly | Ala | |
| | | | 20 | | | | | 25 | | | | | 30 | | | |
| CCA | GTG | AAG | ATG | ACC | GTG | TCT | CAG | GGG | CAG | CCA | GTG | AAG | CTC | AAC | TGC | 380 |
| Pro | Val | Lys | Met | Thr | Val | Ser | Gln | Gly | Gln | Pro | Val | Lys | Leu | Asn | Cys | |
| | | 35 | | | | | 40 | | | | | 45 | | | | |
| AGC | GTG | GAG | GGG | ATG | GAG | GAC | CCT | GAC | ATC | CAC | TGG | ATG | AAG | GAT | GGC | 428 |
| Ser | Val | Glu | Gly | Met | Glu | Asp | Pro | Asp | Ile | His | Trp | Met | Lys | Asp | Gly | |
| | 50 | | | | | 55 | | | | | 60 | | | | | |
| ACC | GTG | GTC | CAG | AAT | GCA | AGC | CAG | GTG | TCC | ATC | TCC | ATC | AGC | GAG | CAC | 476 |
| Thr | Val | Val | Gln | Asn | Ala | Ser | Gln | Val | Ser | Ile | Ser | Ile | Ser | Glu | His | |
| 65 | | | | | 70 | | | | | 75 | | | | | 80 | |
| AGC | TGG | ATT | GGC | TTA | CTC | AGC | CTA | AAG | TCA | GTG | GAA | CGG | TCT | GAT | GCT | 524 |
| Ser | Trp | Ile | Gly | Leu | Leu | Ser | Leu | Lys | Ser | Val | Glu | Arg | Ser | Asp | Ala | |
| | | | | 85 | | | | | 90 | | | | | 95 | | |
| GGC | CTG | TAC | TGG | TGC | CAG | GTG | AAG | GAT | GGG | GAG | GAA | ACC | AAG | ATT | TCT | 572 |
| Gly | Leu | Tyr | Trp | Cys | Gln | Val | Lys | Asp | Gly | Glu | Glu | Thr | Lys | Ile | Ser | |
| | | | 100 | | | | | 105 | | | | | 110 | | | |
| CAG | TCA | GTA | TGG | CTC | ACT | GTC | GAA | GGT | GTG | CCA | TTC | TTC | ACA | GTG | GAA | 620 |
| Gln | Ser | Val | Trp | Leu | Thr | Val | Glu | Gly | Val | Pro | Phe | Phe | Thr | Val | Glu | |
| | | 115 | | | | | 120 | | | | | 125 | | | | |
| CCA | AAA | GAT | CTG | GCG | GTG | CCA | CCC | AAT | GCC | CCT | TTT | CAG | CTG | TCT | TGT | 668 |
| Pro | Lys | Asp | Leu | Ala | Val | Pro | Pro | Asn | Ala | Pro | Phe | Gln | Leu | Ser | Cys | |
| | 130 | | | | | 135 | | | | | 140 | | | | | |
| GAG | GCT | GTG | GGT | CCT | CCA | GAA | CCC | GTA | ACC | ATT | TAC | TGG | TGG | AGA | GGA | 716 |
| Glu | Ala | Val | Gly | Pro | Pro | Glu | Pro | Val | Thr | Ile | Tyr | Trp | Trp | Arg | Gly | |
| 145 | | | | | 150 | | | | | 155 | | | | | 160 | |
| CTC | ACT | AAG | GTT | GGG | GGA | CCT | GCT | CCC | TCT | CCC | TCT | GTT | TTA | AAT | GTG | 764 |
| Leu | Thr | Lys | Val | Gly | Gly | Pro | Ala | Pro | Ser | Pro | Ser | Val | Leu | Asn | Val | |
| | | | | 165 | | | | | 170 | | | | | 175 | | |
| ACA | GGA | GTG | ACC | CAG | CGC | ACA | GAG | TTT | TCT | TGT | GAA | GCC | CGC | AAC | ATA | 812 |
| Thr | Gly | Val | Thr | Gln | Arg | Thr | Glu | Phe | Ser | Cys | Glu | Ala | Arg | Asn | Ile | |
| | | | 180 | | | | | 185 | | | | | 190 | | | |
| AAA | GGC | CTG | GCC | ACT | TCC | CGA | CCA | GCC | ATT | GTT | CGC | CTT | CAA | GCA | CCG | 860 |
| Lys | Gly | Leu | Ala | Thr | Ser | Arg | Pro | Ala | Ile | Val | Arg | Leu | Gln | Ala | Pro | |
| | | 195 | | | | | 200 | | | | | 205 | | | | |
| CCT | GCA | GCT | CCT | TTC | AAC | ACC | ACA | GTA | ACA | ACG | ATC | TCC | AGC | TAC | AAC | 908 |
| Pro | Ala | Ala | Pro | Phe | Asn | Thr | Thr | Val | Thr | Thr | Ile | Ser | Ser | Tyr | Asn | |
| | 210 | | | | | 215 | | | | | 220 | | | | | |
| GCT | AGC | GTG | GCC | TGG | GTG | CCA | GGT | GCT | GAC | GGC | CTA | GCT | CTG | CTG | CAT | 956 |
| Ala | Ser | Val | Ala | Trp | Val | Pro | Gly | Ala | Asp | Gly | Leu | Ala | Leu | Leu | His | |
| 225 | | | | | 230 | | | | | 235 | | | | | 240 | |
| TCC | TGT | ACT | GTA | CAG | GTG | GCA | CAC | GCC | CCA | GGA | GAA | TGG | GAG | GCC | CTT | 1004 |
| Ser | Cys | Thr | Val | Gln | Val | Ala | His | Ala | Pro | Gly | Glu | Trp | Glu | Ala | Leu | |
| | | | | 245 | | | | | 250 | | | | | 255 | | |

| | | | | | | | | | | | | | | | | |
|---|---|---|---|---|---|---|---|---|---|---|---|---|---|---|---|---|
| GCT | GTT | GTG | GTT | CCT | GTG | CCA | CCT | TTT | ACC | TGC | CTG | CTT | CGG | AAC | TTG | 1052 |
| Ala | Val | Val | Val | Pro | Val | Pro | Pro | Phe | Thr | Cys | Leu | Leu | Arg | Asn | Leu | |
| | | | 260 | | | | 265 | | | | | | 270 | | | |
| GCC | CCT | GCC | ACC | AAC | TAC | AGC | CTT | AGG | GTG | CGC | TGT | GCC | AAT | GCC | TTG | 1100 |
| Ala | Pro | Ala | Thr | Asn | Tyr | Ser | Leu | Arg | Val | Arg | Cys | Ala | Asn | Ala | Leu | |
| | 275 | | | | | 280 | | | | | 285 | | | | | |
| GGC | CCT | TCT | CCC | TAC | GGC | GAC | TGG | GTG | CCC | TTT | CAG | ACA | AAG | GGC | CTA | 1148 |
| Gly | Pro | Ser | Pro | Tyr | Gly | Asp | Trp | Val | Pro | Phe | Gln | Thr | Lys | Gly | Leu | |
| | 290 | | | | 295 | | | | | | 300 | | | | | |
| GCG | CCA | CGC | AGA | GCT | CCT | CAG | AAT | TTC | CAT | GCC | ATT | CGT | ACC | GAC | TCA | 1196 |
| Ala | Pro | Arg | Arg | Ala | Pro | Gln | Asn | Phe | His | Ala | Ile | Arg | Thr | Asp | Ser | |
| 305 | | | | | 310 | | | | | 315 | | | | | 320 | |
| GGC | CTT | ATC | CTG | GAA | TGG | GAA | GAA | GTG | ATT | CCT | GAG | GAC | CCT | GGG | GAA | 1244 |
| Gly | Leu | Ile | Leu | Glu | Trp | Glu | Glu | Val | Ile | Pro | Glu | Asp | Pro | Gly | Glu | |
| | | | | 325 | | | | | 330 | | | | | 335 | | |
| GGC | CCC | CTA | GGA | CCT | TAT | AAG | CTG | TCC | TGG | GTC | CAA | GAA | AAT | GGA | ACC | 1292 |
| Gly | Pro | Leu | Gly | Pro | Tyr | Lys | Leu | Ser | Trp | Val | Gln | Glu | Asn | Gly | Thr | |
| | | | 340 | | | | 345 | | | | | | 350 | | | |
| CAG | GAT | GAG | CTG | ATG | GTG | GAA | GGG | ACC | AGG | GCC | AAT | CTG | ACC | GAC | TGG | 1340 |
| Gln | Asp | Glu | Leu | Met | Val | Glu | Gly | Thr | Arg | Ala | Asn | Leu | Thr | Asp | Trp | |
| | | 355 | | | | | 360 | | | | | 365 | | | | |
| GTA | CCC | CAG | AAG | GAC | CTG | ATT | TTG | CGT | GTG | TGT | GCC | TCC | AAT | GCA | ATT | 1388 |
| Val | Pro | Gln | Lys | Asp | Leu | Ile | Leu | Arg | Val | Cys | Ala | Ser | Asn | Ala | Ile | |
| | 370 | | | | | 375 | | | | | 380 | | | | | |
| GGT | GAT | GGG | CCC | TGG | AGT | CAG | CCA | CTG | GTG | GTG | TCT | TCT | CAT | GAC | CAT | 1436 |
| Gly | Asp | Gly | Pro | Trp | Ser | Gln | Pro | Leu | Val | Val | Ser | Ser | His | Asp | His | |
| 385 | | | | | 390 | | | | | 395 | | | | | 400 | |
| GCA | GGG | AGG | CAG | GGC | CCT | CCC | CAC | AGC | CGC | ACA | TCC | TGG | GTG | CCT | GTG | 1484 |
| Ala | Gly | Arg | Gln | Gly | Pro | Pro | His | Ser | Arg | Thr | Ser | Trp | Val | Pro | Val | |
| | | | | 405 | | | | | 410 | | | | | 415 | | |
| GTC | CTG | GGC | GTG | CTC | ACC | GCC | CTG | ATC | ACA | GCT | GCT | GCC | TTG | GCC | CTC | 1532 |
| Val | Leu | Gly | Val | Leu | Thr | Ala | Leu | Ile | Thr | Ala | Ala | Ala | Leu | Ala | Leu | |
| | | | 420 | | | | | 425 | | | | | 430 | | | |
| ATC | CTG | CTT | CGG | AAG | AGA | CGC | AAG | GAG | ACG | CGT | TTC | GGG | CAA | GCC | TTT | 1580 |
| Ile | Leu | Leu | Arg | Lys | Arg | Arg | Lys | Glu | Thr | Arg | Phe | Gly | Gln | Ala | Phe | |
| | | 435 | | | | | 440 | | | | | 445 | | | | |
| GAC | AGT | GTC | ATG | GCC | CGA | GGG | GAG | CCA | GCT | GTA | CAC | TTC | CGG | GCA | GCC | 1628 |
| Asp | Ser | Val | Met | Ala | Arg | Gly | Glu | Pro | Ala | Val | His | Phe | Arg | Ala | Ala | |
| | 450 | | | | | 455 | | | | | 460 | | | | | |
| CGA | TCT | TTC | AAT | CGA | GAA | AGG | CCT | GAA | CGC | ATT | GAG | GCC | ACA | TTG | GAT | 1676 |
| Arg | Ser | Phe | Asn | Arg | Glu | Arg | Pro | Glu | Arg | Ile | Glu | Ala | Thr | Leu | Asp | |
| 465 | | | | | 470 | | | | | 475 | | | | | 480 | |
| AGC | CTG | GGC | ATC | AGC | GAT | GAA | TTG | AAG | GAA | AAG | CTG | GAG | GAT | GTC | CTC | 1724 |
| Ser | Leu | Gly | Ile | Ser | Asp | Glu | Leu | Lys | Glu | Lys | Leu | Glu | Asp | Val | Leu | |
| | | | | 485 | | | | | 490 | | | | | 495 | | |
| ATT | CCA | GAG | CAG | CAG | TTC | ACC | CTC | GGT | CGG | ATG | TTG | GGC | AAA | GGA | GAG | 1772 |
| Ile | Pro | Glu | Gln | Gln | Phe | Thr | Leu | Gly | Arg | Met | Leu | Gly | Lys | Gly | Glu | |
| | | | 500 | | | | | 505 | | | | | 510 | | | |
| TTT | GGA | TCA | GTG | CGG | GAA | GCC | CAG | CTA | AAG | CAG | GAA | GAT | GGC | TCC | TTC | 1820 |
| Phe | Gly | Ser | Val | Arg | Glu | Ala | Gln | Leu | Lys | Gln | Glu | Asp | Gly | Ser | Phe | |
| | | 515 | | | | | 520 | | | | | 525 | | | | |
| GTG | AAA | GTG | GCA | GTG | AAG | ATG | CTG | AAA | GCT | GAC | ATC | ATT | GCC | TCA | AGC | 1868 |
| Val | Lys | Val | Ala | Val | Lys | Met | Leu | Lys | Ala | Asp | Ile | Ile | Ala | Ser | Ser | |
| | 530 | | | | | 535 | | | | | 540 | | | | | |
| GAC | ATA | GAA | GAG | TTC | CTC | CGG | GAA | GCA | GCT | TGC | ATG | AAG | GAG | TTT | GAC | 1916 |
| Asp | Ile | Glu | Glu | Phe | Leu | Arg | Glu | Ala | Ala | Cys | Met | Lys | Glu | Phe | Asp | |
| 545 | | | | | 550 | | | | | 555 | | | | | 560 | |
| CAT | CCA | CAC | GTG | GCC | AAG | CTT | GTT | GGG | GTG | AGC | CTC | CGG | AGC | AGG | GCT | 1964 |
| His | Pro | His | Val | Ala | Lys | Leu | Val | Gly | Val | Ser | Leu | Arg | Ser | Arg | Ala | |
| | | | | 565 | | | | | 570 | | | | | 575 | | |

| | | | | | | | | | | | | | | | | |
|---|---|---|---|---|---|---|---|---|---|---|---|---|---|---|---|---|
| AAA | GGT | CGT | CTC | CCC | ATT | CCC | ATG | GTC | ATC | CTG | CCC | TTC | ATG | AAA | CAT | 2012 |
| Lys | Gly | Arg | Leu<br>580 | Pro | Ile | Pro | Met<br>585 | Val | Ile | Leu | Pro | Phe | Met<br>590 | Lys | His | |
| GGA | GAC | TTG | CAC | GCC | TTT | CTG | CTC | GCC | TCC | CGA | ATC | GGG | GAG | AAC | CCT | 2060 |
| Gly | Asp | Leu | His<br>595 | Ala | Phe | Leu | Leu<br>600 | Ala | Ser | Arg | Ile | Gly<br>605 | Glu | Asn | Pro | |
| TTT | AAC | CTG | CCC | CTC | CAG | ACC | CTG | GTC | CGG | TTC | ATG | GTG | GAC | ATT | CGC | 2108 |
| Phe | Asn<br>610 | Leu | Pro | Leu | Gln | Thr<br>615 | Leu | Val | Arg | Phe | Met<br>620 | Val | Asp | Ile | Arg | |
| TGT | GGC | ATG | GAG | TAC | CTG | AGC | TCC | CGG | AAC | TTC | ATC | CAC | CGA | GAC | CTA | 2156 |
| Cys<br>625 | Gly | Met | Glu | Tyr | Leu<br>630 | Ser | Ser | Arg | Asn | Phe<br>635 | Ile | His | Arg | Asp | Leu<br>640 | |
| GCA | GCT | CGG | AAT | TGC | ATG | CTG | GCC | GAG | GAC | ATG | ACA | GTG | TGT | GTG | GCT | 2204 |
| Ala | Ala | Arg | Asn | Cys<br>645 | Met | Leu | Ala | Glu | Asp<br>650 | Met | Thr | Val | Cys | Val<br>655 | Ala | |
| GAT | TTT | GGA | CTC | TCT | CGG | AAA | ATC | TAT | AGC | GGG | GAC | TAT | TAT | CGT | CAG | 2252 |
| Asp | Phe | Gly | Leu<br>660 | Ser | Arg | Lys | Ile | Tyr<br>665 | Ser | Gly | Asp | Tyr | Tyr<br>670 | Arg | Gln | |
| GGC | TGT | GCC | TCC | AAA | TTG | CCC | GTC | AAG | TGG | CTG | GCC | CTG | GAG | AGC | TTG | 2300 |
| Gly | Cys | Ala<br>675 | Ser | Lys | Leu | Pro | Val<br>680 | Lys | Trp | Leu | Ala | Leu<br>685 | Glu | Ser | Leu | |
| GCT | GAC | AAC | TTG | TAT | ACT | GTA | CAC | AGT | GAT | GTG | TGG | GCC | TTC | GGG | GTG | 2348 |
| Ala | Asp<br>690 | Asn | Leu | Tyr | Thr | Val<br>695 | His | Ser | Asp | Val | Trp<br>700 | Ala | Phe | Gly | Val | |
| ACC | ATG | TGG | GAG | ATC | ATG | ACT | CGT | GGG | CAG | ACG | CCA | TAT | GCT | GGC | ATT | 2396 |
| Thr<br>705 | Met | Trp | Glu | Ile | Met<br>710 | Thr | Arg | Gly | Gln | Thr<br>715 | Pro | Tyr | Ala | Gly | Ile<br>720 | |
| GAA | AAT | GCC | GAG | ATT | TAC | AAC | TAC | CTC | ATC | GGC | GGG | AAC | CGC | CTG | AAG | 2444 |
| Glu | Asn | Ala | Glu | Ile<br>725 | Tyr | Asn | Tyr | Leu | Ile<br>730 | Gly | Gly | Asn | Arg | Leu<br>735 | Lys | |
| CAG | CCT | CCG | GAG | TGC | ATG | GAG | GAA | GTG | TAT | GAT | CTC | ATG | TAC | CAG | TGC | 2492 |
| Gln | Pro | Pro | Glu<br>740 | Cys | Met | Glu | Glu | Val<br>745 | Tyr | Asp | Leu | Met | Tyr<br>750 | Gln | Cys | |
| TGG | AGC | GCC | GAC | CCC | AAG | CAG | CGC | CCA | AGC | TTC | ACG | TGT | CTG | CGA | ATG | 2540 |
| Trp | Ser | Ala<br>755 | Asp | Pro | Lys | Gln | Arg<br>760 | Pro | Ser | Phe | Thr | Cys<br>765 | Leu | Arg | Met | |
| GAA | CTG | GAG | AAC | ATT | CTG | GGC | CAC | CTG | TCT | GTG | CTG | TCC | ACC | AGC | CAG | 2588 |
| Glu | Leu | Glu<br>770 | Asn | Ile | Leu | Gly | His<br>775 | Leu | Ser | Val | Leu | Ser<br>780 | Thr | Ser | Gln | |
| GAC | CCC | TTG | TAC | ATC | AAC | ATT | GAG | AGA | GCT | GAG | CAG | CCT | ACT | GAG | AGT | 2636 |
| Asp<br>785 | Pro | Leu | Tyr | Ile | Asn<br>790 | Ile | Glu | Arg | Ala | Glu<br>795 | Gln | Pro | Thr | Glu | Ser<br>800 | |
| GGC | AGC | CCT | GAG | GTC | CAC | TGT | GGA | GAG | CGA | TCC | AGC | AGC | GAG | GCA | GGG | 2684 |
| Gly | Ser | Pro | Glu | Val<br>805 | His | Cys | Gly | Glu | Arg<br>810 | Ser | Ser | Ser | Glu | Ala<br>815 | Gly | |
| GAC | GGC | AGT | GGC | GTG | GGG | GCA | GTA | GGT | GGC | ATC | CCC | AGT | GAC | TCT | CGG | 2732 |
| Asp | Gly | Ser | Gly<br>820 | Val | Gly | Ala | Val | Gly<br>825 | Gly | Ile | Pro | Ser | Asp<br>830 | Ser | Arg | |
| TAC | ATC | TTC | AGC | CCC | GGA | GGG | CTA | TCC | GAG | TCA | CCA | GGG | CAG | CTG | GAG | 2780 |
| Tyr | Ile | Phe | Ser<br>835 | Pro | Gly | Gly | Leu | Ser<br>840 | Glu | Ser | Pro | Gly | Gln<br>845 | Leu | Glu | |
| CAG | CAG | CCA | GAA | AGC | CCC | CTC | AAT | GAG | AAC | CAG | AGG | CTG | TTG | TTG | CTG | 2828 |
| Gln | Gln | Pro<br>850 | Glu | Ser | Pro | Leu | Asn<br>855 | Glu | Asn | Gln | Arg<br>860 | Leu | Leu | Leu | Leu | |
| CAG | CAA | GGG | CTA | CTG | CCT | CAC | AGT | AGC | TGT | T | AACCCTCAGG | CAGAGGAAAG | | | | 2879 |
| Gln<br>865 | Gln | Gly | Leu | Leu | Pro<br>870 | His | Ser | Ser | Cys | | | | | | | |
| TTGGGGCCCC | TGGCTCTGCT | GACCGCTGTG | CTGCCTGACT | AGGCCCAGTC | TGATCACAGC | | | | | | | | | | | 2939 |
| CCAGGCAGCA | AGGTATGGAG | GCTCCTGTGG | TAGCCCTCCC | AAGCTGTGCT | GGCGCCTGGA | | | | | | | | | | | 2999 |

| CGGACCAAAT | TGCCCAATCC | CAGTTCTTCC | TGCAGCCGCT | CTGGCCAGCC | TGGCATCAGT | 3059 |
| TCAGGCCTTG | GCTTACAGGA | GGTGAGCCAG | AGCTGGTTGC | CTGAATGCAG | GCAGCTGGCA | 3119 |
| GGAGGGGAGG | GTGGCTATGT | TTCCATGGGT | ACCATGGTTG | TGGATGGCAG | TAAGGGAGGG | 3179 |
| TAGCAACAGC | CCTGTGCGCC | CTACCCTCCT | GGCTGAGCTG | CTCCTACTTT | AGTGCATGCT | 3239 |
| TGGAGCCGCC | TGCAGCCTGG | AACTCAGCAC | TGCCCACCAC | ACTTGGGCCG | AAATGCCAGG | 3299 |
| TTTGCCCC   |            |            |            |            |            | 3307 |

( 2 ) INFORMATION FOR SEQ ID NO:6:

( i ) SEQUENCE CHARACTERISTICS:
        ( A ) LENGTH: 874 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Gly  Trp  Pro  Gly  Leu  Arg  Pro  Leu  Leu  Leu  Ala  Gly  Leu  Ala  Ser
 1              5                        10                       15

Leu  Leu  Leu  Pro  Gly  Ser  Ala  Ala  Ala  Gly  Leu  Lys  Leu  Met  Gly  Ala
                20                       25                       30

Pro  Val  Lys  Met  Thr  Val  Ser  Gln  Gly  Gln  Pro  Val  Lys  Leu  Asn  Cys
           35                        40                       45

Ser  Val  Glu  Gly  Met  Glu  Asp  Pro  Asp  Ile  His  Trp  Met  Lys  Asp  Gly
     50                       55                       60

Thr  Val  Val  Gln  Asn  Ala  Ser  Gln  Val  Ser  Ile  Ser  Ile  Ser  Glu  His
 65                       70                       75                       80

Ser  Trp  Ile  Gly  Leu  Leu  Ser  Leu  Lys  Ser  Val  Glu  Arg  Ser  Asp  Ala
                     85                       90                       95

Gly  Leu  Tyr  Trp  Cys  Gln  Val  Lys  Asp  Gly  Glu  Glu  Thr  Lys  Ile  Ser
               100                      105                      110

Gln  Ser  Val  Trp  Leu  Thr  Val  Glu  Gly  Val  Pro  Phe  Phe  Thr  Val  Glu
          115                       120                      125

Pro  Lys  Asp  Leu  Ala  Val  Pro  Pro  Asn  Ala  Pro  Phe  Gln  Leu  Ser  Cys
     130                      135                      140

Glu  Ala  Val  Gly  Pro  Pro  Glu  Pro  Val  Thr  Ile  Tyr  Trp  Trp  Arg  Gly
145                      150                      155                      160

Leu  Thr  Lys  Val  Gly  Gly  Pro  Ala  Pro  Ser  Pro  Ser  Val  Leu  Asn  Val
                     165                      170                      175

Thr  Gly  Val  Thr  Gln  Arg  Thr  Glu  Phe  Ser  Cys  Glu  Ala  Arg  Asn  Ile
               180                      185                      190

Lys  Gly  Leu  Ala  Thr  Ser  Arg  Pro  Ala  Ile  Val  Arg  Leu  Gln  Ala  Pro
          195                      200                      205

Pro  Ala  Ala  Pro  Phe  Asn  Thr  Thr  Val  Thr  Thr  Ile  Ser  Ser  Tyr  Asn
     210                      215                      220

Ala  Ser  Val  Ala  Trp  Val  Pro  Gly  Ala  Asp  Gly  Leu  Ala  Leu  Leu  His
225                      230                      235                      240

Ser  Cys  Thr  Val  Gln  Val  Ala  His  Ala  Pro  Gly  Glu  Trp  Glu  Ala  Leu
                     245                      250                      255

Ala  Val  Val  Val  Pro  Val  Pro  Pro  Phe  Thr  Cys  Leu  Leu  Arg  Asn  Leu
               260                      265                      270

Ala  Pro  Ala  Thr  Asn  Tyr  Ser  Leu  Arg  Val  Arg  Cys  Ala  Asn  Ala  Leu
          275                      280                      285

Gly  Pro  Ser  Pro  Tyr  Gly  Asp  Trp  Val  Pro  Phe  Gln  Thr  Lys  Gly  Leu
     290                      295                      300
```

| Ala | Pro | Arg | Arg | Ala | Pro | Gln | Asn | Phe | His | Ala | Ile | Arg | Thr | Asp | Ser |
| 305 | | | | 310 | | | | | 315 | | | | | | 320 |

| Gly | Leu | Ile | Leu | Glu | Trp | Glu | Glu | Val | Ile | Pro | Glu | Asp | Pro | Gly | Glu |
| | | | | 325 | | | | | 330 | | | | | 335 | |

| Gly | Pro | Leu | Gly | Pro | Tyr | Lys | Leu | Ser | Trp | Val | Gln | Glu | Asn | Gly | Thr |
| | | | 340 | | | | | 345 | | | | | 350 | | |

| Gln | Asp | Glu | Leu | Met | Val | Glu | Gly | Thr | Arg | Ala | Asn | Leu | Thr | Asp | Trp |
| | | 355 | | | | | 360 | | | | | 365 | | | |

| Val | Pro | Gln | Lys | Asp | Leu | Ile | Leu | Arg | Val | Cys | Ala | Ser | Asn | Ala | Ile |
| 370 | | | | | 375 | | | | | 380 | | | | | |

| Gly | Asp | Gly | Pro | Trp | Ser | Gln | Pro | Leu | Val | Val | Ser | Ser | His | Asp | His |
| 385 | | | | 390 | | | | | 395 | | | | | | 400 |

| Ala | Gly | Arg | Gln | Gly | Pro | Pro | His | Ser | Arg | Thr | Ser | Trp | Val | Pro | Val |
| | | | | 405 | | | | | 410 | | | | | 415 | |

| Val | Leu | Gly | Val | Leu | Thr | Ala | Leu | Ile | Thr | Ala | Ala | Ala | Leu | Ala | Leu |
| | | | 420 | | | | | 425 | | | | | 430 | | |

| Ile | Leu | Leu | Arg | Lys | Arg | Arg | Lys | Glu | Thr | Arg | Phe | Gly | Gln | Ala | Phe |
| | | 435 | | | | | 440 | | | | | 445 | | | |

| Asp | Ser | Val | Met | Ala | Arg | Gly | Glu | Pro | Ala | Val | His | Phe | Arg | Ala | Ala |
| 450 | | | | | 455 | | | | | 460 | | | | | |

| Arg | Ser | Phe | Asn | Arg | Glu | Arg | Pro | Glu | Arg | Ile | Glu | Ala | Thr | Leu | Asp |
| 465 | | | | | 470 | | | | | 475 | | | | | 480 |

| Ser | Leu | Gly | Ile | Ser | Asp | Glu | Leu | Lys | Glu | Lys | Leu | Glu | Asp | Val | Leu |
| | | | | 485 | | | | | 490 | | | | | 495 | |

| Ile | Pro | Glu | Gln | Gln | Phe | Thr | Leu | Gly | Arg | Met | Leu | Gly | Lys | Gly | Glu |
| | | | 500 | | | | | 505 | | | | | 510 | | |

| Phe | Gly | Ser | Val | Arg | Glu | Ala | Gln | Leu | Lys | Gln | Glu | Asp | Gly | Ser | Phe |
| | | 515 | | | | | 520 | | | | | 525 | | | |

| Val | Lys | Val | Ala | Val | Lys | Met | Leu | Lys | Ala | Asp | Ile | Ile | Ala | Ser | Ser |
| | 530 | | | | | 535 | | | | | 540 | | | | |

| Asp | Ile | Glu | Glu | Phe | Leu | Arg | Glu | Ala | Ala | Cys | Met | Lys | Glu | Phe | Asp |
| 545 | | | | | 550 | | | | | 555 | | | | | 560 |

| His | Pro | His | Val | Ala | Lys | Leu | Val | Gly | Val | Ser | Leu | Arg | Ser | Arg | Ala |
| | | | | 565 | | | | | 570 | | | | | 575 | |

| Lys | Gly | Arg | Leu | Pro | Ile | Pro | Met | Val | Ile | Leu | Pro | Phe | Met | Lys | His |
| | | | 580 | | | | | 585 | | | | | 590 | | |

| Gly | Asp | Leu | His | Ala | Phe | Leu | Leu | Ala | Ser | Arg | Ile | Gly | Glu | Asn | Pro |
| | | | 595 | | | | | 600 | | | | | 605 | | |

| Phe | Asn | Leu | Pro | Leu | Gln | Thr | Leu | Val | Arg | Phe | Met | Val | Asp | Ile | Arg |
| | | 610 | | | | | 615 | | | | | 620 | | | |

| Cys | Gly | Met | Glu | Tyr | Leu | Ser | Ser | Arg | Asn | Phe | Ile | His | Arg | Asp | Leu |
| 625 | | | | | 630 | | | | | 635 | | | | | 640 |

| Ala | Ala | Arg | Asn | Cys | Met | Leu | Ala | Glu | Asp | Met | Thr | Val | Cys | Val | Ala |
| | | | | 645 | | | | | 650 | | | | | 655 | |

| Asp | Phe | Gly | Leu | Ser | Arg | Lys | Ile | Tyr | Ser | Gly | Asp | Tyr | Tyr | Arg | Gln |
| | | | 660 | | | | | 665 | | | | | 670 | | |

| Gly | Cys | Ala | Ser | Lys | Leu | Pro | Val | Lys | Trp | Leu | Ala | Leu | Glu | Ser | Leu |
| | | 675 | | | | | 680 | | | | | 685 | | | |

| Ala | Asp | Asn | Leu | Tyr | Thr | Val | His | Ser | Asp | Val | Trp | Ala | Phe | Gly | Val |
| | 690 | | | | | 695 | | | | | 700 | | | | |

| Thr | Met | Trp | Glu | Ile | Met | Thr | Arg | Gly | Gln | Thr | Pro | Tyr | Ala | Gly | Ile |
| 705 | | | | | 710 | | | | | 715 | | | | | 720 |

| Glu | Asn | Ala | Glu | Ile | Tyr | Asn | Tyr | Leu | Ile | Gly | Gly | Asn | Arg | Leu | Lys |

|     |     |     |     |     |     |     |     |     |     |     |     |     |     |     |
|-----|-----|-----|-----|-----|-----|-----|-----|-----|-----|-----|-----|-----|-----|-----|
|     |     |     |     | 725 |     |     |     | 730 |     |     |     | 735 |     |     |
| Gln | Pro | Pro | Glu | Cys | Met | Glu | Glu | Val | Tyr | Asp | Leu | Met | Tyr | Gln | Cys |
|     |     |     | 740 |     |     |     | 745 |     |     |     |     | 750 |     |     |
| Trp | Ser | Ala | Asp | Pro | Lys | Gln | Arg | Pro | Ser | Phe | Thr | Cys | Leu | Arg | Met |
|     |     | 755 |     |     |     |     | 760 |     |     |     |     | 765 |     |     |
| Glu | Leu | Glu | Asn | Ile | Leu | Gly | His | Leu | Ser | Val | Leu | Ser | Thr | Ser | Gln |
|     |     | 770 |     |     |     |     | 775 |     |     |     |     | 780 |     |     |
| Asp | Pro | Leu | Tyr | Ile | Asn | Ile | Glu | Arg | Ala | Glu | Gln | Pro | Thr | Glu | Ser |
| 785 |     |     |     |     | 790 |     |     |     |     | 795 |     |     |     |     | 800 |
| Gly | Ser | Pro | Glu | Val | His | Cys | Gly | Glu | Arg | Ser | Ser | Ser | Glu | Ala | Gly |
|     |     |     |     | 805 |     |     |     |     | 810 |     |     |     |     | 815 |     |
| Asp | Gly | Ser | Gly | Val | Gly | Ala | Val | Gly | Gly | Ile | Pro | Ser | Asp | Ser | Arg |
|     |     |     | 820 |     |     |     |     | 825 |     |     |     |     | 830 |     |     |
| Tyr | Ile | Phe | Ser | Pro | Gly | Gly | Leu | Ser | Glu | Ser | Pro | Gly | Gln | Leu | Glu |
|     |     | 835 |     |     |     |     | 840 |     |     |     |     | 845 |     |     |     |
| Gln | Gln | Pro | Glu | Ser | Pro | Leu | Asn | Glu | Asn | Gln | Arg | Leu | Leu | Leu | Leu |
|     | 850 |     |     |     |     | 855 |     |     |     |     | 860 |     |     |     |     |
| Gln | Gln | Gly | Leu | Leu | Pro | His | Ser | Ser | Cys |     |     |     |     |     |     |
| 865 |     |     |     |     | 870 |     |     |     |     |     |     |     |     |     |     |

( 2 ) INFORMATION FOR SEQ ID NO:7:

( i ) SEQUENCE CHARACTERISTICS:
  ( A ) LENGTH: 165 base pairs
  ( B ) TYPE: nucleic acid
  ( C ) STRANDEDNESS: single
  ( D ) TOPOLOGY: linear ( i i ) MOLECULE TYPE: DNA ( v i i ) IMMEDIATE SOURCE:
  ( B ) CLONE: Tyro-4

( i x ) FEATURE:
  ( A ) NAME/KEY: CDS
  ( B ) LOCATION: 1..165

( x i ) SEQUENCE DESCRIPTION: SEQ ID NO:7:

| AAC | ATC | TTG | ATC | AAC | AGT | AAC | TTG | GTG | TGC | AAA | GTC | TCT | GAC | TTC | GGA | 48 |
|-----|-----|-----|-----|-----|-----|-----|-----|-----|-----|-----|-----|-----|-----|-----|-----|----|
| Asn | Ile | Leu | Ile | Asn | Ser | Asn | Leu | Val | Cys | Lys | Val | Ser | Asp | Phe | Gly |    |
| 1   |     |     |     | 5   |     |     |     |     | 10  |     |     |     |     | 15  |     |    |
| CTT | TCT | CGA | GTG | TTG | GAA | GAT | GAC | CCT | GAA | GCT | GCT | TAC | ACC | ACC | AGA | 96 |
| Leu | Ser | Arg | Val | Leu | Glu | Asp | Asp | Pro | Glu | Ala | Ala | Tyr | Thr | Thr | Arg |    |
|     |     |     | 20  |     |     |     |     | 25  |     |     |     |     | 30  |     |     |    |
| GGA | GGA | AAG | ATA | CCA | ATA | AGG | TGG | ACA | TCA | CCA | GAA | GCA | ATT | GCC | TAC | 144 |
| Gly | Gly | Lys | Ile | Pro | Ile | Arg | Trp | Thr | Ser | Pro | Glu | Ala | Ile | Ala | Tyr |    |
|     |     |     | 35  |     |     |     | 40  |     |     |     |     | 45  |     |     |     |    |
| CGC | AAG | TTC | ACA | TCA | GCC | AGC |     |     |     |     |     |     |     |     |     | 165 |
| Arg | Lys | Phe | Thr | Ser | Ala | Ser |     |     |     |     |     |     |     |     |     |    |
|     | 50  |     |     |     |     | 55  |     |     |     |     |     |     |     |     |     |    |

( 2 ) INFORMATION FOR SEQ ID NO:8:

( i ) SEQUENCE CHARACTERISTICS:
  ( A ) LENGTH: 55 amino acids
  ( B ) TYPE: amino acid
  ( D ) TOPOLOGY: linear ( i i ) MOLECULE TYPE: protein ( x ) SEQUENCE DESCRIPTION: SEQ ID NO:8:

| Asn | Ile | Leu | Ile | Asn | Ser | Asn | Leu | Val | Cys | Lys | Val | Ser | Asp | Phe | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Ser | Arg | Val | Leu | Glu | Asp | Asp | Pro | Glu | Ala | Ala | Tyr | Thr | Thr | Arg |
|-----|-----|-----|-----|-----|-----|-----|-----|-----|-----|-----|-----|-----|-----|-----|-----|
|     |     |     | 20  |     |     |     | 25  |     |     |     |     | 30  |     |     |     |

| Gly | Gly | Lys | Ile | Pro | Ile | Arg | Trp | Thr | Ser | Pro | Glu | Ala | Ile | Ala | Tyr |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Arg | Lys | Phe | Thr | Ser | Ala | Ser |
|-----|-----|-----|-----|-----|-----|-----|
|     | 50  |     |     |     |     | 55  |

( 2 ) INFORMATION FOR SEQ ID NO:9:

( i ) SEQUENCE CHARACTERISTICS:
        ( A ) LENGTH: 171 base pairs
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE:
        ( B ) CLONE: Tyro-5

( i x ) FEATURE:
        ( A ) NAME/KEY: CDS
        ( B ) LOCATION: 1..171

( x i ) SEQUENCE DESCRIPTION: SEQ ID NO:9:

| AAC | ATC | CTT | GTC | AAT | AGC | AAC | CTG | GTG | TGC | AAG | GTG | TCT | GAC | TTC | GGG | 48 |
|-----|-----|-----|-----|-----|-----|-----|-----|-----|-----|-----|-----|-----|-----|-----|-----|----|
| Asn | Ile | Leu | Val | Asn | Ser | Asn | Leu | Val | Cys | Lys | Val | Ser | Asp | Phe | Gly |    |
| 1   |     |     |     | 5   |     |     |     |     | 10  |     |     |     |     | 15  |     |    |

| CTC | TCA | CGC | TTC | CTG | GAG | GAC | GAC | ACA | TCT | GAC | CCC | ACC | TAC | ACC | AGC | 96 |
|-----|-----|-----|-----|-----|-----|-----|-----|-----|-----|-----|-----|-----|-----|-----|-----|----|
| Leu | Ser | Arg | Phe | Leu | Glu | Asp | Asp | Thr | Ser | Asp | Pro | Thr | Tyr | Thr | Ser |    |
|     |     |     | 20  |     |     |     | 25  |     |     |     |     | 30  |     |     |     |    |

| GCT | CTG | GGT | GGG | AAG | ATC | CCC | ATC | CGT | TGG | ACA | GCA | CCG | GAA | GCC | ATC | 144 |
|-----|-----|-----|-----|-----|-----|-----|-----|-----|-----|-----|-----|-----|-----|-----|-----|-----|
| Ala | Leu | Gly | Gly | Lys | Ile | Pro | Ile | Arg | Trp | Thr | Ala | Pro | Glu | Ala | Ile |     |
|     |     | 35  |     |     |     |     | 40  |     |     |     |     | 45  |     |     |     |     |

| CAG | TAC | CGG | AAA | TTC | ACC | TCA | GCC | AGT | 171 |
|-----|-----|-----|-----|-----|-----|-----|-----|-----|-----|
| Gln | Tyr | Arg | Lys | Phe | Thr | Ser | Ala | Ser |     |
|     | 50  |     |     |     |     | 55  |     |     |     |

( 2 ) INFORMATION FOR SEQ ID NO:10:

( i ) SEQUENCE CHARACTERISTICS:
        ( A ) LENGTH: 57 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| Asn | Ile | Leu | Val | Asn | Ser | Asn | Leu | Val | Cys | Lys | Val | Ser | Asp | Phe | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Ser | Arg | Phe | Leu | Glu | Asp | Asp | Thr | Ser | Asp | Pro | Thr | Tyr | Thr | Ser |
|-----|-----|-----|-----|-----|-----|-----|-----|-----|-----|-----|-----|-----|-----|-----|-----|
|     |     |     | 20  |     |     |     | 25  |     |     |     |     | 30  |     |     |     |

| Ala | Leu | Gly | Gly | Lys | Ile | Pro | Ile | Arg | Trp | Thr | Ala | Pro | Glu | Ala | Ile |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Gln | Tyr | Arg | Lys | Phe | Thr | Ser | Ala | Ser |
|-----|-----|-----|-----|-----|-----|-----|-----|-----|
|     | 50  |     |     |     |     | 55  |     |     |

( 2 ) INFORMATION FOR SEQ ID NO:11:

( i ) SEQUENCE CHARACTERISTICS:
        ( A ) LENGTH: 171 base pairs
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE:
  ( B ) CLONE: Tyro-6

( i x ) FEATURE:
  ( A ) NAME/KEY: CDS
  ( B ) LOCATION: 1..171

( x i ) SEQUENCE DESCRIPTION: SEQ ID NO:11:

```
AAC ATC CTT GTC AAC AGT AAC TTG GTC TGC AAA GTA TCT GAC TTT GGG      48
Asn Ile Leu Val Asn Ser Asn Leu Val Cys Lys Val Ser Asp Phe Gly
 1               5                  10                  15

CTC TCC CGC TTC CTG GAG GAC GAC CCC TCA GAC CCC ACC TAC ACC AGC      96
Leu Ser Arg Phe Leu Glu Asp Asp Pro Ser Asp Pro Thr Tyr Thr Ser
             20                  25                  30

TCC CTG GGT GGG AAG ATC CCT ATC CGT TGG ACC GCC CCA GAG GCC ATA     144
Ser Leu Gly Gly Lys Ile Pro Ile Arg Trp Thr Ala Pro Glu Ala Ile
         35                  40                  45

GCC TAT CGG AAG TTC ACG TCT GCC AGC                                  171
Ala Tyr Arg Lys Phe Thr Ser Ala Ser
     50                  55
```

( 2 ) INFORMATION FOR SEQ ID NO:12:

( i ) SEQUENCE CHARACTERISTICS:
    ( A ) LENGTH: 57 amino acids
    ( B ) TYPE: amino acid
    ( D ) TOPOLOGY: linear ( i i ) MOLECULE TYPE: protein ( x i ) SEQUENCE DESCRIPTION: SEQ ID NO:12:

```
Asn Ile Leu Val Asn Ser Asn Leu Val Cys Lys Val Ser Asp Phe Gly
 1               5                  10                  15

Leu Ser Arg Phe Leu Glu Asp Asp Pro Ser Asp Pro Thr Tyr Thr Ser
             20                  25                  30

Ser Leu Gly Gly Lys Ile Pro Ile Arg Trp Thr Ala Pro Glu Ala Ile
         35                  40                  45

Ala Tyr Arg Lys Phe Thr Ser Ala Ser
     50                  55
```

( 2 ) INFORMATION FOR SEQ ID NO:13:

( i ) SEQUENCE CHARACTERISTICS:
    ( A ) LENGTH: 162 base pairs
    ( B ) TYPE: nucleic acid
    ( C ) STRANDEDNESS: single
    ( D ) TOPOLOGY: linear ( i i ) MOLECULE TYPE: DNA ( v i i ) IMMEDIATE SOURCE:
    ( B ) CLONE: Tyro-7

( i x ) FEATURE:
    ( A ) NAME/KEY: CDS
    ( B ) LOCATION: 1..162

( x i ) SEQUENCE DESCRIPTION: SEQ ID NO:13:

```
AAC TGC ATG CTG AAT GAG AAC ATG TCC GTG TGC GTG GCA GAC TTC GGG      48
Asn Cys Met Leu Asn Glu Asn Met Ser Val Cys Val Ala Asp Phe Gly
 1               5                  10                  15

CTC TCC AAG AAG ATC TAC AAT GGG GAT TAC TAC CGC CAA GGG CGC ATT      96
Leu Ser Lys Lys Ile Tyr Asn Gly Asp Tyr Tyr Arg Gln Gly Arg Ile
             20                  25                  30

GCC AAG ATG CCA GTC AAG TGG ATT GCT ATC GAG AGT CTG GCA GAT CGA     144
Ala Lys Met Pro Val Lys Trp Ile Ala Ile Glu Ser Leu Ala Asp Arg
         35                  40                  45
```

```
GTC  TAC  ACC  AGC  AAG  AGT                                                                                      162
Val  Tyr  Thr  Ser  Lys  Ser
      50
```

( 2 ) INFORMATION FOR SEQ ID NO:14:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Asn  Cys  Met  Leu  Asn  Glu  Asn  Met  Ser  Val  Cys  Val  Ala  Asp  Phe  Gly
 1              5                         10                         15

Leu  Ser  Lys  Lys  Ile  Tyr  Asn  Gly  Asp  Tyr  Tyr  Arg  Gln  Gly  Arg  Ile
               20                        25                        30

Ala  Lys  Met  Pro  Val  Lys  Trp  Ile  Ala  Ile  Glu  Ser  Leu  Ala  Asp  Arg
               35                        40                        45

Val  Tyr  Thr  Ser  Lys  Ser
      50
```

( 2 ) INFORMATION FOR SEQ ID NO:15:

( i ) SEQUENCE CHARACTERISTICS:
        ( A ) LENGTH: 159 base pairs
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE:
        ( B ) CLONE: Tyro-8

( i x ) FEATURE:
        ( A ) NAME/KEY: CDS
        ( B ) LOCATION: 1..159

( x i ) SEQUENCE DESCRIPTION: SEQ ID NO:15:

```
AAC  TGT  TTG  GTG  GAC  AGT  GAT  CTC  TCC  GTG  AAA  GTC  TCA  GAC  TTT  GGA   48
Asn  Cys  Leu  Val  Asp  Ser  Asp  Leu  Ser  Val  Lys  Val  Ser  Asp  Phe  Gly
 1              5                         10                        15

ATG  ACG  AGA  TAT  GTC  CTT  GAT  GAC  CAG  TAT  GTC  AGT  TCA  GTA  GGA  ACC   96
Met  Thr  Arg  Tyr  Val  Leu  Asp  Asp  Gln  Tyr  Val  Ser  Ser  Val  Gly  Thr
               20                        25                        30

AAG  TTT  CCA  GTC  AAG  TGG  TCG  GCC  CCA  GAG  GTG  TTT  CAC  TAT  TTC  AAA  144
Lys  Phe  Pro  Val  Lys  Trp  Ser  Ala  Pro  Glu  Val  Phe  His  Tyr  Phe  Lys
               35                        40                        45

TAC  AGC  AGC  AAG  TCG                                                          159
Tyr  Ser  Ser  Lys  Ser
      50
```

( 2 ) INFORMATION FOR SEQ ID NO:16:

( i ) SEQUENCE CHARACTERISTICS:
        ( A ) LENGTH: 53 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Asn  Cys  Leu  Val  Asp  Ser  Asp  Leu  Ser  Val  Lys  Val  Ser  Asp  Phe  Gly
 1              5                         10                        15
```

```
Met  Thr  Arg  Tyr  Val  Leu  Asp  Asp  Gln  Tyr  Val  Ser  Ser  Val  Gly  Thr
          20                       25                      30

Lys  Phe  Pro  Val  Lys  Trp  Ser  Ala  Pro  Glu  Val  Phe  His  Tyr  Phe  Lys
          35                       40                      45

Tyr  Ser  Ser  Lys  Ser
          50
```

( 2 ) INFORMATION FOR SEQ ID NO:17:

( i ) SEQUENCE CHARACTERISTICS:
        ( A ) LENGTH: 162 base pairs
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE:
        ( B ) CLONE: Tyro-9

( i x ) FEATURE:
        ( A ) NAME/KEY: CDS
        ( B ) LOCATION: 1..162

( x i ) SEQUENCE DESCRIPTION: SEQ ID NO:17:

```
AAC  GTG  CTG  GTG  ACC  GAG  GAT  GAC  GTG  ATG  AAG  ATC  GCT  GAC  TTT  GGT        48
Asn  Val  Leu  Val  Thr  Glu  Asp  Asp  Val  Met  Lys  Ile  Ala  Asp  Phe  Gly
 1                       5                       10                      15

CTG  GCC  CGT  GGT  GTC  CAC  CAC  ATC  GAC  TAC  TAT  AAG  AAA  ACC  AGC  AAT        96
Leu  Ala  Arg  Gly  Val  His  His  Ile  Asp  Tyr  Tyr  Lys  Lys  Thr  Ser  Asn
               20                       25                      30

GGC  CGC  CTG  CCA  GTC  AAG  TGG  ATG  GCT  CCT  GAG  GCG  TTG  TTT  GAC  CGT       144
Gly  Arg  Leu  Pro  Val  Lys  Trp  Met  Ala  Pro  Glu  Ala  Leu  Phe  Asp  Arg
          35                       40                      45

GTA  TAC  ACA  CAC  CAG  AGT                                                         162
Val  Tyr  Thr  His  Gln  Ser
 50
```

( 2 ) INFORMATION FOR SEQ ID NO:18:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Asn  Val  Leu  Val  Thr  Glu  Asp  Asp  Val  Met  Lys  Ile  Ala  Asp  Phe  Gly
 1                       5                       10                      15

Leu  Ala  Arg  Gly  Val  His  His  Ile  Asp  Tyr  Tyr  Lys  Lys  Thr  Ser  Asn
               20                       25                      30

Gly  Arg  Leu  Pro  Val  Lys  Trp  Met  Ala  Pro  Glu  Ala  Leu  Phe  Asp  Arg
          35                       40                      45

Val  Tyr  Thr  His  Gln  Ser
 50
```

( 2 ) INFORMATION FOR SEQ ID NO:19:

( i ) SEQUENCE CHARACTERISTICS:
        ( A ) LENGTH: 3120 base pairs
        ( B ) TYPE: nucleic acid
        ( C ) STRANDEDNESS: single
        ( D ) TOPOLOGY: linear ( i i ) MOLECULE TYPE: DNA -continued (vii) IMMEDIATE SOURCE:
    (B) CLONE: Tyro-10

(ix) FEATURE:
    (A) NAME/KEY: CDS
    (B) LOCATION: 485..3047

(xi) SEQUENCE DESCRIPTION: SEQ ID NO:19:

```
GGGCCCGGGT CTAAGTGGAC TTCTCTTGGT GTGTCAGGAA AAGTTCGGAA AAGCGGCAGA      60
GGGCAGAGTT TGAATCAGGG CGGAAGGGCA GGGAGCTGGG CTCTTCAAGA CTCAGGACCG     120
AGGCAGATCT CATGTTTTGG GGTCTGGATT TGTGTCAGCG AGGGAAGAAC AGGCGCCAAT     180
AACCAAAGAA GGCTGAAGCG AGGTACAGGA CTCCATAGCA GCTGCAAGTA CAATAAACAG     240
TTTTAGCAGA GCTGGAAATG TTGGCAGGCA AGACAGGCCG ATCGCAGAGT CGGGCTGCTG     300
GAGAGAGGGA AATCTACAAG CGACCTGACA TTTGGTGCTC TAGAGCATTC TAAGGCTTGC     360
TGCTTGACTT CTAAAGAAGC TGAAATAATT GAGGAGGAGC GGGGACCCTC TGTTTCCAAG     420
GACTCTGTTC TGCAGAGAAT GTTCTGCACC CTCTGATACT CCAGATCCAA CTCCGTCTTC     480
```

| | | | | | | | | | | | | | | | | | |
|---|---|---|---|---|---|---|---|---|---|---|---|---|---|---|---|---|---|
| TGAA | ATG | ATC | CCG | ATT | CCC | AGA | ATG | CCC | CTG | GTG | CTG | CTC | CTG | CTC | TTG | | 529 |
| | Met | Ile | Pro | Ile | Pro | Arg | Met | Pro | Leu | Val | Leu | Leu | Leu | Leu | Leu | | |
| | 1 | | | 5 | | | | | 10 | | | | | | 15 | | |
| CTC | ATC | CTG | GGT | TCT | GCA | AAA | GCT | CAG | GTT | AAT | CCA | GCC | ATA | TGC | CGC | | 577 |
| Leu | Ile | Leu | Gly | Ser | Ala | Lys | Ala | Gln | Val | Asn | Pro | Ala | Ile | Cys | Arg | | |
| | | | | 20 | | | | 25 | | | | | 30 | | | | |
| TAT | CCT | CTG | GGC | ATG | TCA | GGA | GGC | CAC | ATT | CCA | GAT | GAG | GAC | ATC | ACA | | 625 |
| Tyr | Pro | Leu | Gly | Met | Ser | Gly | Gly | His | Ile | Pro | Asp | Glu | Asp | Ile | Thr | | |
| | | | 35 | | | | 40 | | | | | 45 | | | | | |
| GCC | TCA | AGT | CAG | TGG | TCA | GAA | TCC | ACG | GCT | GCC | AAA | TAT | GGG | AGG | CTG | | 673 |
| Ala | Ser | Ser | Gln | Trp | Ser | Glu | Ser | Thr | Ala | Ala | Lys | Tyr | Gly | Arg | Leu | | |
| | | 50 | | | | | 55 | | | | | | 60 | | | | |
| GAC | TCT | GAA | GAA | GGA | GAT | GGA | GCC | TGG | TGT | CCT | GAG | ATT | CCA | GTG | CAA | | 721 |
| Asp | Ser | Glu | Glu | Gly | Asp | Gly | Ala | Trp | Cys | Pro | Glu | Ile | Pro | Val | Gln | | |
| | 65 | | | | 70 | | | | | 75 | | | | | | | |
| CCC | GAT | GAC | CTG | AAG | GAA | TTT | CTG | CAG | ATT | GAC | TTG | CGA | ACC | CTA | CAC | | 769 |
| Pro | Asp | Asp | Leu | Lys | Glu | Phe | Leu | Gln | Ile | Asp | Leu | Arg | Thr | Leu | His | | |
| 80 | | | | | 85 | | | | | 90 | | | | | 95 | | |
| TTT | ATC | ACT | CTT | GTG | GGG | ACC | CAG | GGG | CGC | CAT | GCA | GGG | GGT | CAT | GGC | | 817 |
| Phe | Ile | Thr | Leu | Val | Gly | Thr | Gln | Gly | Arg | His | Ala | Gly | Gly | His | Gly | | |
| | | | | 100 | | | | | 105 | | | | | 110 | | | |
| ATT | GAA | TTT | GCA | CCC | ATG | TAC | AAG | ATC | AAC | TAC | AGT | CGG | GAT | GGC | AGT | | 865 |
| Ile | Glu | Phe | Ala | Pro | Met | Tyr | Lys | Ile | Asn | Tyr | Ser | Arg | Asp | Gly | Ser | | |
| | | | | 115 | | | | | 120 | | | | | 125 | | | |
| CGC | TGG | ATC | TCC | TGG | CGT | AAC | CGG | CAT | GGG | AAG | CAG | GTG | CTT | GAT | GGA | | 913 |
| Arg | Trp | Ile | Ser | Trp | Arg | Asn | Arg | His | Gly | Lys | Gln | Val | Leu | Asp | Gly | | |
| | | | 130 | | | | 135 | | | | | 140 | | | | | |
| AAC | AGT | AAC | CCT | TAT | GAT | GTA | TTC | CTG | AAG | GAC | TTG | GAG | CCA | CCC | ATC | | 961 |
| Asn | Ser | Asn | Pro | Tyr | Asp | Val | Phe | Leu | Lys | Asp | Leu | Glu | Pro | Pro | Ile | | |
| | 145 | | | | | 150 | | | | | 155 | | | | | | |
| GTC | GCC | AGA | TTT | GTT | CGC | CTT | ATC | CCA | GTC | ACT | GAC | CAC | TCC | ATG | AAC | | 1009 |
| Val | Ala | Arg | Phe | Val | Arg | Leu | Ile | Pro | Val | Thr | Asp | His | Ser | Met | Asn | | |
| 160 | | | | | 165 | | | | | 170 | | | | | 175 | | |
| GTG | TGC | ATG | AGG | GTT | GAG | CTT | TAT | GGT | TGT | GTC | TGG | CTA | GAT | GGC | TTG | | 1057 |
| Val | Cys | Met | Arg | Val | Glu | Leu | Tyr | Gly | Cys | Val | Trp | Leu | Asp | Gly | Leu | | |
| | | | | 180 | | | | | 185 | | | | | 190 | | | |
| GTA | TCC | TAC | AAT | GCT | CCA | GCT | GGA | CAG | CAG | TTT | GTA | CTC | CCT | GGA | GGC | | 1105 |
| Val | Ser | Tyr | Asn | Ala | Pro | Ala | Gly | Gln | Gln | Phe | Val | Leu | Pro | Gly | Gly | | |
| | | | 195 | | | | 200 | | | | | 205 | | | | | |
| TCC | ATC | ATT | TAT | CTG | AAT | GAT | TCT | GTC | TAT | GAT | GGA | GCT | GTT | GGG | TAC | | 1153 |
| Ser | Ile | Ile | Tyr | Leu | Asn | Asp | Ser | Val | Tyr | Asp | Gly | Ala | Val | Gly | Tyr | | |
| | | 210 | | | | | 215 | | | | | 220 | | | | | |

| | | | | | | | | | | | | | | | | |
|---|---|---|---|---|---|---|---|---|---|---|---|---|---|---|---|---|
| AGC | ATG | ACT | GAA | GGG | CTA | GGC | CAG | TTG | ACT | GAT | GGA | GTA | TCC | GGC | CTG | 1201 |
| Ser | Met | Thr | Glu | Gly | Leu | Gly | Gln | Leu | Thr | Asp | Gly | Val | Ser | Gly | Leu | |
| | 225 | | | | 230 | | | | | 235 | | | | | | |
| GAT | GAT | TTT | ACC | CAG | ACC | CAT | GAA | TAC | CAC | GTG | TGG | CCT | GGC | TAT | GAC | 1249 |
| Asp | Asp | Phe | Thr | Gln | Thr | His | Glu | Tyr | His | Val | Trp | Pro | Gly | Tyr | Asp | |
| 240 | | | | | 245 | | | | | 250 | | | | | 255 | |
| TAC | GTG | GGA | TGG | CGG | AAC | GAA | AGT | GCT | ACC | AAC | GGT | TTC | ATT | GAG | ATC | 1297 |
| Tyr | Val | Gly | Trp | Arg | Asn | Glu | Ser | Ala | Thr | Asn | Gly | Phe | Ile | Glu | Ile | |
| | | | | 260 | | | | | 265 | | | | | 270 | | |
| ATG | TTT | GAA | TTT | GAC | CGA | ATC | AGG | AAT | TTT | ACT | ACC | ATG | AAG | GTC | CAC | 1345 |
| Met | Phe | Glu | Phe | Asp | Arg | Ile | Arg | Asn | Phe | Thr | Thr | Met | Lys | Val | His | |
| | | | 275 | | | | | 280 | | | | | 285 | | | |
| TGC | AAC | AAC | ATG | TTT | GCT | AAA | GGT | GTG | AAG | ATT | TTT | AAG | GAG | GTC | CAG | 1393 |
| Cys | Asn | Asn | Met | Phe | Ala | Lys | Gly | Val | Lys | Ile | Phe | Lys | Glu | Val | Gln | |
| | | 290 | | | | | 295 | | | | | 300 | | | | |
| TGC | TAC | TTT | CGC | TCG | GAA | GCC | AGC | GAG | TGG | GAA | CCC | ACT | GCT | GTC | TAC | 1441 |
| Cys | Tyr | Phe | Arg | Ser | Glu | Ala | Ser | Glu | Trp | Glu | Pro | Thr | Ala | Val | Tyr | |
| | 305 | | | | | 310 | | | | | 315 | | | | | |
| TTT | CCC | CTG | GTC | CTG | GAC | GAT | GTG | AAC | CCC | AGT | GCC | CGG | TTT | GTC | ACG | 1489 |
| Phe | Pro | Leu | Val | Leu | Asp | Asp | Val | Asn | Pro | Ser | Ala | Arg | Phe | Val | Thr | |
| 320 | | | | | 325 | | | | | 330 | | | | | 335 | |
| GTG | CCC | CTC | CAC | CAC | CGA | ATG | GCC | AGT | GCC | ATC | AAG | TGC | CAA | TAC | CAT | 1537 |
| Val | Pro | Leu | His | His | Arg | Met | Ala | Ser | Ala | Ile | Lys | Cys | Gln | Tyr | His | |
| | | | | 340 | | | | | 345 | | | | | 350 | | |
| TTT | GCC | GAC | ACG | TGG | ATG | ATG | TTC | AGC | GAG | ATC | ACT | TTC | CAA | TCA | GAT | 1585 |
| Phe | Ala | Asp | Thr | Trp | Met | Met | Phe | Ser | Glu | Ile | Thr | Phe | Gln | Ser | Asp | |
| | | | 355 | | | | | 360 | | | | | 365 | | | |
| GCT | GCA | ATG | TAT | AAC | AAC | TCT | GGA | GCC | CTT | CCC | ACC | TCT | CCT | ATG | GCA | 1633 |
| Ala | Ala | Met | Tyr | Asn | Asn | Ser | Gly | Ala | Leu | Pro | Thr | Ser | Pro | Met | Ala | |
| | | 370 | | | | | 375 | | | | | 380 | | | | |
| CCC | ACC | ACC | TAT | GAT | CCC | ATG | CTT | AAA | GTT | GAT | GAT | AGC | AAC | ACT | CGG | 1681 |
| Pro | Thr | Thr | Tyr | Asp | Pro | Met | Leu | Lys | Val | Asp | Asp | Ser | Asn | Thr | Arg | |
| | 385 | | | | | 390 | | | | | 395 | | | | | |
| ATC | CTG | ATT | GGT | TGC | TTG | GTG | GCC | ATC | ATC | TTC | ATC | CTG | CTG | GCT | ATC | 1729 |
| Ile | Leu | Ile | Gly | Cys | Leu | Val | Ala | Ile | Ile | Phe | Ile | Leu | Leu | Ala | Ile | |
| 400 | | | | | 405 | | | | | 410 | | | | | 415 | |
| ATC | GTC | ATC | ATC | CTG | TGG | AGG | CAG | TTC | TGG | CAG | AAG | ATG | CTA | GAA | AAG | 1777 |
| Ile | Val | Ile | Ile | Leu | Trp | Arg | Gln | Phe | Trp | Gln | Lys | Met | Leu | Glu | Lys | |
| | | | | 420 | | | | | 425 | | | | | 430 | | |
| GCT | TCA | CGG | AGG | ATG | CTG | GAT | GAT | GAA | ATG | ACA | GTC | AGC | CTT | TCC | CTG | 1825 |
| Ala | Ser | Arg | Arg | Met | Leu | Asp | Asp | Glu | Met | Thr | Val | Ser | Leu | Ser | Leu | |
| | | | 435 | | | | | 440 | | | | | 445 | | | |
| CCC | AGC | GAG | TCC | AGC | ATG | TTC | AAT | AAC | AAC | CGC | TCC | TCA | TCA | CCA | AGT | 1873 |
| Pro | Ser | Glu | Ser | Ser | Met | Phe | Asn | Asn | Asn | Arg | Ser | Ser | Ser | Pro | Ser | |
| | | 450 | | | | | 455 | | | | | 460 | | | | |
| GAA | CAG | GAG | TCC | AAC | TCT | ACT | TAT | GAT | CGA | ATC | TTC | CCC | CTT | CGC | CCT | 1921 |
| Glu | Gln | Glu | Ser | Asn | Ser | Thr | Tyr | Asp | Arg | Ile | Phe | Pro | Leu | Arg | Pro | |
| | 465 | | | | | 470 | | | | | 475 | | | | | |
| GAC | TAC | CAG | GAG | CCA | TCC | AGA | CTG | ATC | CGA | AAG | CTT | CCA | GAG | TTT | GCT | 1969 |
| Asp | Tyr | Gln | Glu | Pro | Ser | Arg | Leu | Ile | Arg | Lys | Leu | Pro | Glu | Phe | Ala | |
| 480 | | | | | 485 | | | | | 490 | | | | | 495 | |
| CCA | GGA | GAG | GAG | GAG | TCA | GGG | TGC | AGT | GGT | GTT | GTG | AAG | CCG | GCC | CAG | 2017 |
| Pro | Gly | Glu | Glu | Glu | Ser | Gly | Cys | Ser | Gly | Val | Val | Lys | Pro | Ala | Gln | |
| | | | | 500 | | | | | 505 | | | | | 510 | | |
| CCC | AAT | GGA | CCT | GAG | GGC | GTG | CCC | CAC | TAT | GCA | GAA | GCC | GAC | ATA | GTG | 2065 |
| Pro | Asn | Gly | Pro | Glu | Gly | Val | Pro | His | Tyr | Ala | Glu | Ala | Asp | Ile | Val | |
| | | | 515 | | | | | 520 | | | | | 525 | | | |
| AAT | CTC | CAG | GGA | GTG | ACA | GGT | GGC | AAC | ACC | TAC | TGT | GTG | CCT | GCT | GTA | 2113 |
| Asn | Leu | Gln | Gly | Val | Thr | Gly | Gly | Asn | Thr | Tyr | Cys | Val | Pro | Ala | Val | |
| | | 530 | | | | | 535 | | | | | 540 | | | | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ACC | ATG | GAT | CTG | CTA | TCG | GGG | AAA | GAT | GTG | GCT | GTG | GAA | GAG | TTC | CCC | 2161 |
| Thr | Met | Asp | Leu | Leu | Ser | Gly | Lys | Asp | Val | Ala | Val | Glu | Glu | Phe | Pro |      |
|     | 545 |     |     |     |     |     | 550 |     |     |     |     | 555 |     |     |     |      |
| AGG | AAA | CTG | TTG | GCC | TTC | AAG | GAG | AAG | CTG | GGA | GAA | GGC | CAG | TTT | GGG | 2209 |
| Arg | Lys | Leu | Leu | Ala | Phe | Lys | Glu | Lys | Leu | Gly | Glu | Gly | Gln | Phe | Gly |      |
| 560 |     |     |     |     | 565 |     |     |     |     | 570 |     |     |     |     | 575 |      |
| GAG | GTT | CAT | CTC | TGT | GAA | GTG | GAG | GGA | ATG | GAA | AAA | TTC | AAA | GAC | AAA | 2257 |
| Glu | Val | His | Leu | Cys | Glu | Val | Glu | Gly | Met | Glu | Lys | Phe | Lys | Asp | Lys |      |
|     |     |     |     | 580 |     |     |     |     | 585 |     |     |     |     | 590 |     |      |
| GAT | TTT | GCA | CTA | GAT | GTC | AGT | GCC | AAC | CAG | CCT | GTC | CTG | GTG | GCC | GTG | 2305 |
| Asp | Phe | Ala | Leu | Asp | Val | Ser | Ala | Asn | Gln | Pro | Val | Leu | Val | Ala | Val |      |
|     |     |     | 595 |     |     |     |     | 600 |     |     |     |     | 605 |     |     |      |
| AAA | ATG | CTC | CGA | GCA | GAT | GCC | AAC | AAG | AAT | GCC | AGG | AAT | GAT | TTT | CTT | 2353 |
| Lys | Met | Leu | Arg | Ala | Asp | Ala | Asn | Lys | Asn | Ala | Arg | Asn | Asp | Phe | Leu |      |
|     |     | 610 |     |     |     |     | 615 |     |     |     |     | 620 |     |     |     |      |
| AAG | GAG | ATC | AAG | ATC | ATG | TCT | CGG | CTC | AAG | GAC | CCA | AAC | ATC | ATC | CGT | 2401 |
| Lys | Glu | Ile | Lys | Ile | Met | Ser | Arg | Leu | Lys | Asp | Pro | Asn | Ile | Ile | Arg |      |
|     | 625 |     |     |     |     | 630 |     |     |     |     | 635 |     |     |     |     |      |
| CTC | TTA | GCT | GTG | TGC | ATC | ACT | GAG | GAC | CCG | CTC | TGC | ATG | ATC | ACG | GAA | 2449 |
| Leu | Leu | Ala | Val | Cys | Ile | Thr | Glu | Asp | Pro | Leu | Cys | Met | Ile | Thr | Glu |      |
| 640 |     |     |     |     | 645 |     |     |     |     | 650 |     |     |     |     | 655 |      |
| TAC | ATG | GAG | AAT | GGA | GAT | CTT | AAT | CAG | TTT | CTT | TCT | CGC | CAC | GAG | CCT | 2497 |
| Tyr | Met | Glu | Asn | Gly | Asp | Leu | Asn | Gln | Phe | Leu | Ser | Arg | His | Glu | Pro |      |
|     |     |     |     | 660 |     |     |     |     | 665 |     |     |     |     | 670 |     |      |
| CTG | AGT | TCC | TGT | TCT | AGT | GAT | GCC | ACA | GTC | AGT | TAC | GCC | AAC | CTG | AAG | 2545 |
| Leu | Ser | Ser | Cys | Ser | Ser | Asp | Ala | Thr | Val | Ser | Tyr | Ala | Asn | Leu | Lys |      |
|     |     |     | 675 |     |     |     |     | 680 |     |     |     |     | 685 |     |     |      |
| TTT | ATG | GCA | ACC | CAG | ATT | GCC | TCT | GGT | ATG | AAG | TAC | CTT | TCG | TCT | CTC | 2593 |
| Phe | Met | Ala | Thr | Gln | Ile | Ala | Ser | Gly | Met | Lys | Tyr | Leu | Ser | Ser | Leu |      |
|     |     | 690 |     |     |     |     | 695 |     |     |     |     | 700 |     |     |     |      |
| AAC | TTT | GTC | CAC | CGA | GAT | CTG | GCC | ACA | CGA | AAC | TGT | TTA | GTG | GGC | AAG | 2641 |
| Asn | Phe | Val | His | Arg | Asp | Leu | Ala | Thr | Arg | Asn | Cys | Leu | Val | Gly | Lys |      |
|     | 705 |     |     |     |     | 710 |     |     |     |     | 715 |     |     |     |     |      |
| AAT | TAC | ACC | ATC | AAG | ATA | GCT | GAT | TTT | GGC | ATG | AGC | AGA | AAC | CTG | TAC | 2689 |
| Asn | Tyr | Thr | Ile | Lys | Ile | Ala | Asp | Phe | Gly | Met | Ser | Arg | Asn | Leu | Tyr |      |
| 720 |     |     |     |     | 725 |     |     |     |     | 730 |     |     |     |     | 735 |      |
| AGT | GGT | GAT | TAC | TAC | CGG | ATC | CAG | GGC | CGG | GCG | GTG | CTC | CCC | ATT | CGC | 2737 |
| Ser | Gly | Asp | Tyr | Tyr | Arg | Ile | Gln | Gly | Arg | Ala | Val | Leu | Pro | Ile | Arg |      |
|     |     |     |     | 740 |     |     |     |     | 745 |     |     |     |     | 750 |     |      |
| TGG | ATG | TCC | TGG | GAA | AGC | ATC | TTG | CTG | GGC | AAA | TTC | ACC | ACG | GCA | AGT | 2785 |
| Trp | Met | Ser | Trp | Glu | Ser | Ile | Leu | Leu | Gly | Lys | Phe | Thr | Thr | Ala | Ser |      |
|     |     |     | 755 |     |     |     |     | 760 |     |     |     |     | 765 |     |     |      |
| GAT | GTG | TGG | GCC | TTT | GGG | GTG | ACT | CTG | TGG | GAG | ACC | TTC | ACC | TTT | TGC | 2833 |
| Asp | Val | Trp | Ala | Phe | Gly | Val | Thr | Leu | Trp | Glu | Thr | Phe | Thr | Phe | Cys |      |
|     |     | 770 |     |     |     |     | 775 |     |     |     |     | 780 |     |     |     |      |
| CAG | GAG | CAG | CCC | TAT | TCC | CAG | CTG | TCG | GAT | GAG | CAG | GTT | ATC | GAG | AAC | 2881 |
| Gln | Glu | Gln | Pro | Tyr | Ser | Gln | Leu | Ser | Asp | Glu | Gln | Val | Ile | Glu | Asn |      |
|     | 785 |     |     |     |     | 790 |     |     |     |     | 795 |     |     |     |     |      |
| ACT | GGA | GAG | TTC | TTC | CGA | GAC | CAA | GGG | AGG | CAG | ATC | TAT | CTC | CCT | CAA | 2929 |
| Thr | Gly | Glu | Phe | Phe | Arg | Asp | Gln | Gly | Arg | Gln | Ile | Tyr | Leu | Pro | Gln |      |
| 800 |     |     |     |     | 805 |     |     |     |     | 810 |     |     |     |     | 815 |      |
| CCA | GCC | CTT | TGC | CCC | GAC | TCT | GTG | TAT | AAG | CTG | ATG | CTC | AGC | TGC | TGG | 2977 |
| Pro | Ala | Leu | Cys | Pro | Asp | Ser | Val | Tyr | Lys | Leu | Met | Leu | Ser | Cys | Trp |      |
|     |     |     |     | 820 |     |     |     |     | 825 |     |     |     |     | 830 |     |      |
| AGA | AGA | GAA | ACC | AAG | CAC | CGG | CCA | TCC | TTC | CAG | GAA | ATA | CAC | CTC | CTG | 3025 |
| Arg | Arg | Glu | Thr | Lys | His | Arg | Pro | Ser | Phe | Gln | Glu | Ile | His | Leu | Leu |      |
|     |     |     | 835 |     |     |     |     | 840 |     |     |     |     | 845 |     |     |      |

|     |     |     |     |     |     |     | | |
| --- | --- | --- | --- | --- | --- | --- | --- | --- |
| CTT | CTT | CAG | CAA | GGA | GCC | GAG | T GATGATGCAT CAGCACCTGG CAGTGTTCCT | 3077 |
| Leu | Leu | Gln | Gln | Gly | Ala | Glu | | |
|     |     | 850 |     |     |     |     | | |

GTGGCCCAGA TCCTTCCCAC AAGACCTACT GCTCACCCAC ATC    3120

(2) INFORMATION FOR SEQ ID NO:20:

(i) SEQUENCE CHARACTERISTICS:
        (A) LENGTH: 854 amino acids
        (B) TYPE: amino acid
        (D) TOPOLOGY: linear (ii) MOLECULE TYPE: protein (xi) SEQUENCE DESCRIPTION: SEQ ID NO:20:

```
Met Ile Pro Ile Pro Arg Met Pro Leu Val Leu Leu Leu Leu Leu
 1               5                  10                  15

Ile Leu Gly Ser Ala Lys Ala Gln Val Asn Pro Ala Ile Cys Arg Tyr
            20                  25                  30

Pro Leu Gly Met Ser Gly Gly His Ile Pro Asp Glu Asp Ile Thr Ala
            35                  40                  45

Ser Ser Gln Trp Ser Glu Ser Thr Ala Ala Lys Tyr Gly Arg Leu Asp
        50                  55                  60

Ser Glu Glu Gly Asp Gly Ala Trp Cys Pro Glu Ile Pro Val Gln Pro
 65                 70                  75                  80

Asp Asp Leu Lys Glu Phe Leu Gln Ile Asp Leu Arg Thr Leu His Phe
                85                  90                  95

Ile Thr Leu Val Gly Thr Gln Gly Arg His Ala Gly Gly His Gly Ile
            100                 105                 110

Glu Phe Ala Pro Met Tyr Lys Ile Asn Tyr Ser Arg Asp Gly Ser Arg
            115                 120                 125

Trp Ile Ser Trp Arg Asn Arg His Gly Lys Gln Val Leu Asp Gly Asn
    130                 135                 140

Ser Asn Pro Tyr Asp Val Phe Leu Lys Asp Leu Glu Pro Pro Ile Val
145                 150                 155                 160

Ala Arg Phe Val Arg Leu Ile Pro Val Thr Asp His Ser Met Asn Val
                165                 170                 175

Cys Met Arg Val Glu Leu Tyr Gly Cys Val Trp Leu Asp Gly Leu Val
            180                 185                 190

Ser Tyr Asn Ala Pro Ala Gly Gln Gln Phe Val Leu Pro Gly Gly Ser
            195                 200                 205

Ile Ile Tyr Leu Asn Asp Ser Val Tyr Asp Gly Ala Val Gly Tyr Ser
    210                 215                 220

Met Thr Glu Gly Leu Gly Gln Leu Thr Asp Gly Val Ser Gly Leu Asp
225                 230                 235                 240

Asp Phe Thr Gln Thr His Glu Tyr His Val Trp Pro Gly Tyr Asp Tyr
                245                 250                 255

Val Gly Trp Arg Asn Glu Ser Ala Thr Asn Gly Phe Ile Glu Ile Met
            260                 265                 270

Phe Glu Phe Asp Arg Ile Arg Asn Phe Thr Thr Met Lys Val His Cys
            275                 280                 285

Asn Asn Met Phe Ala Lys Gly Val Lys Ile Phe Lys Glu Val Gln Cys
290                 295                 300

Tyr Phe Arg Ser Glu Ala Ser Glu Trp Glu Pro Thr Ala Val Tyr Phe
305                 310                 315                 320

Pro Leu Val Leu Asp Asp Val Asn Pro Ser Ala Arg Phe Val Thr Val
                325                 330                 335

Pro Leu His His Arg Met Ala Ser Ala Ile Lys Cys Gln Tyr His Phe
                340                 345                 350
```

```
Ala  Asp  Thr  Trp  Met  Met  Phe  Ser  Glu  Ile  Thr  Phe  Gln  Ser  Asp  Ala
          355                      360                     365

Ala  Met  Tyr  Asn  Asn  Ser  Gly  Ala  Leu  Pro  Thr  Ser  Pro  Met  Ala  Pro
          370                 375                     380

Thr  Thr  Tyr  Asp  Pro  Met  Leu  Lys  Val  Asp  Asp  Ser  Asn  Thr  Arg  Ile
385                      390                     395                         400

Leu  Ile  Gly  Cys  Leu  Val  Ala  Ile  Ile  Phe  Ile  Leu  Leu  Ala  Ile  Ile
                    405                      410                     415

Val  Ile  Ile  Leu  Trp  Arg  Gln  Phe  Trp  Gln  Lys  Met  Leu  Glu  Lys  Ala
               420                      425                     430

Ser  Arg  Arg  Met  Leu  Asp  Asp  Glu  Met  Thr  Val  Ser  Leu  Ser  Leu  Pro
          435                      440                     445

Ser  Glu  Ser  Ser  Met  Phe  Asn  Asn  Asn  Arg  Ser  Ser  Ser  Pro  Ser  Glu
     450                      455                     460

Gln  Glu  Ser  Asn  Ser  Thr  Tyr  Asp  Arg  Ile  Phe  Pro  Leu  Arg  Pro  Asp
465                           470                     475                    480

Tyr  Gln  Glu  Pro  Ser  Arg  Leu  Ile  Arg  Lys  Leu  Pro  Glu  Phe  Ala  Pro
                    485                      490                     495

Gly  Glu  Glu  Glu  Ser  Gly  Cys  Ser  Gly  Val  Val  Lys  Pro  Ala  Gln  Pro
                    500                      505                     510

Asn  Gly  Pro  Glu  Gly  Val  Pro  His  Tyr  Ala  Glu  Ala  Asp  Ile  Val  Asn
               515                      520                     525

Leu  Gln  Gly  Val  Thr  Gly  Gly  Asn  Thr  Tyr  Cys  Val  Pro  Ala  Val  Thr
     530                      535                     540

Met  Asp  Leu  Leu  Ser  Gly  Lys  Asp  Val  Ala  Val  Glu  Glu  Phe  Pro  Arg
545                           550                     555                    560

Lys  Leu  Leu  Ala  Phe  Lys  Glu  Lys  Leu  Gly  Glu  Gly  Gln  Phe  Gly  Glu
                    565                      570                     575

Val  His  Leu  Cys  Glu  Val  Glu  Gly  Met  Glu  Lys  Phe  Lys  Asp  Lys  Asp
               580                      585                     590

Phe  Ala  Leu  Asp  Val  Ser  Ala  Asn  Gln  Pro  Val  Leu  Val  Ala  Val  Lys
          595                      600                     605

Met  Leu  Arg  Ala  Asp  Ala  Asn  Lys  Asn  Ala  Arg  Asn  Asp  Phe  Leu  Lys
     610                      615                     620

Glu  Ile  Lys  Ile  Met  Ser  Arg  Leu  Lys  Asp  Pro  Asn  Ile  Ile  Arg  Leu
625                           630                     635                    640

Leu  Ala  Val  Cys  Ile  Thr  Glu  Asp  Pro  Leu  Cys  Met  Ile  Thr  Glu  Tyr
                    645                      650                     655

Met  Glu  Asn  Gly  Asp  Leu  Asn  Gln  Phe  Leu  Ser  Arg  His  Glu  Pro  Leu
               660                      665                     670

Ser  Ser  Cys  Ser  Ser  Asp  Ala  Thr  Val  Ser  Tyr  Ala  Asn  Leu  Lys  Phe
          675                      680                     685

Met  Ala  Thr  Gln  Ile  Ala  Ser  Gly  Met  Lys  Tyr  Leu  Ser  Ser  Leu  Asn
     690                      695                     700

Phe  Val  His  Arg  Asp  Leu  Ala  Thr  Arg  Asn  Cys  Leu  Val  Gly  Lys  Asn
705                           710                     715                    720

Tyr  Thr  Ile  Lys  Ile  Ala  Asp  Phe  Gly  Met  Ser  Arg  Asn  Leu  Tyr  Ser
                    725                      730                     735

Gly  Asp  Tyr  Tyr  Arg  Ile  Gln  Gly  Arg  Ala  Val  Leu  Pro  Ile  Arg  Trp
               740                      745                     750

Met  Ser  Trp  Glu  Ser  Ile  Leu  Leu  Gly  Lys  Phe  Thr  Thr  Ala  Ser  Asp
          755                      760                     765

Val  Trp  Ala  Phe  Gly  Val  Thr  Leu  Trp  Glu  Thr  Phe  Thr  Phe  Cys  Gln
```

```
             770                         775                         780
Glu  Gln  Pro  Tyr  Ser  Gln  Leu  Ser  Asp  Glu  Gln  Val  Ile  Glu  Asn  Thr
785                      790                      795                      800

Gly  Glu  Phe  Phe  Arg  Asp  Gln  Gly  Arg  Gln  Ile  Tyr  Leu  Pro  Gln  Pro
                    805                      810                      815

Ala  Leu  Cys  Pro  Asp  Ser  Val  Tyr  Lys  Leu  Met  Leu  Ser  Cys  Trp  Arg
               820                      825                      830

Arg  Glu  Thr  Lys  His  Arg  Pro  Ser  Phe  Gln  Glu  Ile  His  Leu  Leu  Leu
          835                      840                      845

Leu  Gln  Gln  Gly  Ala  Glu
     850
```

( 2 ) INFORMATION FOR SEQ ID NO:21:

( i ) SEQUENCE CHARACTERISTICS:
        ( A ) LENGTH: 171 base pairs
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE:
        ( B ) CLONE: Tyro-11

( i x ) FEATURE:
        ( A ) NAME/KEY: CDS
        ( B ) LOCATION: 1..171

( x i ) SEQUENCE DESCRIPTION: SEQ ID NO:21:

```
AAC  ATC  CTG  GTC  AAC  AGT  AAC  CTG  GTC  TGC  AAG  GTG  TCC  GAC  TTT  GGC        48
Asn  Ile  Leu  Val  Asn  Ser  Asn  Leu  Val  Cys  Lys  Val  Ser  Asp  Phe  Gly
1                        5                        10                       15

CTC  TCC  AGA  TTC  CTG  GAG  GAG  AAC  TCC  TCT  GAT  CCC  ACC  TAC  ACA  AGT        96
Leu  Ser  Arg  Phe  Leu  Glu  Glu  Asn  Ser  Ser  Asp  Pro  Thr  Tyr  Thr  Ser
                    20                       25                       30

TCC  CTG  GGA  GGA  AAG  ATT  CCC  ATC  CGA  TGG  ACC  GCC  CCT  GAG  GCC  ATT       144
Ser  Leu  Gly  Gly  Lys  Ile  Pro  Ile  Arg  Trp  Thr  Ala  Pro  Glu  Ala  Ile
               35                       40                       45

GCC  TTC  AGG  AAA  TTC  ACG  TCT  GCC  AGT                                          171
Ala  Phe  Arg  Lys  Phe  Thr  Ser  Ala  Ser
     50                       55
```

( 2 ) INFORMATION FOR SEQ ID NO:22:

( i ) SEQUENCE CHARACTERISTICS:
        ( A ) LENGTH: 57 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Asn  Ile  Leu  Val  Asn  Ser  Asn  Leu  Val  Cys  Lys  Val  Ser  Asp  Phe  Gly
1                        5                        10                       15

Leu  Ser  Arg  Phe  Leu  Glu  Glu  Asn  Ser  Ser  Asp  Pro  Thr  Tyr  Thr  Ser
                    20                       25                       30

Ser  Leu  Gly  Gly  Lys  Ile  Pro  Ile  Arg  Trp  Thr  Ala  Pro  Glu  Ala  Ile
               35                       40                       45

Ala  Phe  Arg  Lys  Phe  Thr  Ser  Ala  Ser
     50                       55
```

( 2 ) INFORMATION FOR SEQ ID NO:23:

( i ) SEQUENCE CHARACTERISTICS:
    ( A ) LENGTH: 162 base pairs
    ( B ) TYPE: nucleic acid
    ( C ) STRANDEDNESS: single
    ( D ) TOPOLOGY: linear ( i i ) MOLECULE TYPE: DNA ( v i i ) IMMEDIATE SOURCE:
    ( B ) CLONE: Tyro-12

( i x ) FEATURE:
    ( A ) NAME/KEY: CDS
    ( B ) LOCATION: 1..162

( x i ) SEQUENCE DESCRIPTION: SEQ ID NO:23:

```
AAT  TGC  ATG  TTG  CGG  GAT  GAC  ATG  ACT  GTC  TGC  GTG  GCA  GAC  TTT  GGC      48
Asn  Cys  Met  Leu  Arg  Asp  Asp  Met  Thr  Val  Cys  Val  Ala  Asp  Phe  Gly
 1                   5                        10                       15

CTC  TCT  AAG  AAG  ATT  TAC  AGT  GGT  GAT  TAT  TAC  CGC  CAA  GGC  CGC  ATT      96
Leu  Ser  Lys  Lys  Ile  Tyr  Ser  Gly  Asp  Tyr  Tyr  Arg  Gln  Gly  Arg  Ile
              20                        25                       30

GCC  AAA  ATG  CCT  GTG  AAG  TGG  ATC  GCC  ATA  GAG  AGC  CTG  GCG  GAC  CGA     144
Ala  Lys  Met  Pro  Val  Lys  Trp  Ile  Ala  Ile  Glu  Ser  Leu  Ala  Asp  Arg
         35                        40                       45

GTC  TAC  ACA  AGC  AAG  AGT                                                        162
Val  Tyr  Thr  Ser  Lys  Ser
 50
```

( 2 ) INFORMATION FOR SEQ ID NO:24:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

```
Asn  Cys  Met  Leu  Arg  Asp  Asp  Met  Thr  Val  Cys  Val  Ala  Asp  Phe  Gly
 1                   5                        10                       15

Leu  Ser  Lys  Lys  Ile  Tyr  Ser  Gly  Asp  Tyr  Tyr  Arg  Gln  Gly  Arg  Ile
              20                        25                       30

Ala  Lys  Met  Pro  Val  Lys  Trp  Ile  Ala  Ile  Glu  Ser  Leu  Ala  Asp  Arg
         35                        40                       45

Val  Tyr  Thr  Ser  Lys  Ser
 50
```

( 2 ) INFORMATION FOR SEQ ID NO:25:

( i ) SEQUENCE CHARACTERISTICS:
        ( A ) LENGTH: 147 base pairs
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE:
        ( B ) CLONE: Tyro-13

( i x ) FEATURE:
        ( A ) NAME/KEY: CDS
        ( B ) LOCATION: 1..147

( x i ) SEQUENCE DESCRIPTION: SEQ ID NO:25:

```
AAT  GTG  CTG  GTG  TCT  GAG  GAC  AAC  GTG  GCC  AAA  GTC  AGT  GAC  TTT  GGC      48
Asn  Val  Leu  Val  Ser  Glu  Asp  Asn  Val  Ala  Lys  Val  Ser  Asp  Phe  Gly
 1                   5                        10                       15
```

```
CTC  ACT  AAG  GAA  GCT  TCC  AGC  ACT  CAG  GAC  ACA  GGC  AAA  CTG  CCA  GTC         96
Leu  Thr  Lys  Glu  Ala  Ser  Ser  Thr  Gln  Asp  Thr  Gly  Lys  Leu  Pro  Val
              20                        25                        30

AAG  TGG  ACA  GCT  CCT  GAA  GCC  TTG  AGA  GAG  AAG  AAA  TTT  TCC  ACC  AAG        144
Lys  Trp  Thr  Ala  Pro  Glu  Ala  Leu  Arg  Glu  Lys  Lys  Phe  Ser  Thr  Lys
         35                        40                        45

TCT                                                                                    147
Ser
```

(2) INFORMATION FOR SEQ ID NO:26:

(i) SEQUENCE CHARACTERISTICS:
        (A) LENGTH: 49 amino acids
        (B) TYPE: amino acid
        (D) TOPOLOGY: linear (ii) MOLECULE TYPE: protein (xi) SEQUENCE DESCRIPTION: SEQ ID NO:26:

```
Asn  Val  Leu  Val  Ser  Glu  Asp  Asn  Val  Ala  Lys  Val  Ser  Asp  Phe  Gly
 1                   5                        10                        15

Leu  Thr  Lys  Glu  Ala  Ser  Ser  Thr  Gln  Asp  Thr  Gly  Lys  Leu  Pro  Val
              20                        25                        30

Lys  Trp  Thr  Ala  Pro  Glu  Ala  Leu  Arg  Glu  Lys  Lys  Phe  Ser  Thr  Lys
         35                        40                        45

Ser
```

(2) INFORMATION FOR SEQ ID NO:27:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:27:

```
His  Arg  Asp  Leu  Ala  Ala  Arg
 1                   5
```

(2) INFORMATION FOR SEQ ID NO:28:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:28:

```
Asp  Val  Trp  Ser  Xaa  Gly  Xaa
 1                   5
```

(2) INFORMATION FOR SEQ ID NO:29:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:29:

```
Pro  Xaa  Xaa  Trp  Xaa  Ala  Pro  Glu
 1              5
```

( 2 ) INFORMATION FOR SEQ ID NO:30:

( i ) SEQUENCE CHARACTERISTICS:
        ( A ) LENGTH: 68 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:30:

```
His  Arg  Asp  Leu  Ala  Ala  Arg  Asn  Val  Leu  Val  Lys  Thr  Pro  Gln  His
 1              5                        10                       15

Val  Lys  Ile  Thr  Asp  Phe  Gly  Leu  Ala  Asp  Leu  Leu  Gly  Ala  Glu  Glu
              20                       25                       30

Lys  Glu  Tyr  His  Ala  Glu  Gly  Gly  Lys  Val  Pro  Ile  Lys  Trp  Met  Ala
         35                       40                       45

Leu  Glu  Ser  Ile  Leu  His  Arg  Ile  Tyr  Thr  His  Gln  Ser  Asp  Val  Trp
    50                       55                       60

Ser  Tyr  Gly  Val
65
```

( 2 ) INFORMATION FOR SEQ ID NO:31:

( i ) SEQUENCE CHARACTERISTICS:
        ( A ) LENGTH: 68 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:31:

```
His  Arg  Asp  Leu  Ala  Ala  Arg  Asn  Cys  Met  Val  Ala  His  Asp  Phe  Thr
 1              5                        10                       15

Val  Lys  Ile  Gly  Asp  Phe  Gly  Met  Thr  Arg  Asp  Ile  Tyr  Glu  Thr  Asp
              20                       25                       30

Tyr  Tyr  Arg  Lys  Gly  Gly  Lys  Gly  Leu  Leu  Pro  Val  Arg  Trp  Met  Ala
         35                       40                       45

Pro  Glu  Ser  Leu  Lys  Asp  Gly  Val  Phe  Thr  Thr  Ser  Ser  Asp  Met  Trp
    50                       55                       60

Ser  Phe  Gly  Val
65
```

( 2 ) INFORMATION FOR SEQ ID NO:32:

( i ) SEQUENCE CHARACTERISTICS:
        ( A ) LENGTH: 68 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:32:

```
His  Arg  Asp  Leu  Ala  Ala  Arg  Asn  Val  Leu  Ile  Cys  Glu  Gly  Lys  Leu
 1              5                        10                       15

Val  Lys  Ile  Cys  Asp  Phe  His  Leu  Ala  Arg  Asp  Ile  Met  Arg  Asp  Ser
              20                       25                       30

Asn  Tyr  Ile  Ser  Lys  Gly  Ser  Thr  Tyr  Leu  Pro  Leu  Lys  Trp  Met  Ala
         35                       40                       45
```

(2) INFORMATION FOR SEQ ID NO:33:

(i) SEQUENCE CHARACTERISTICS:
        (A) LENGTH: 68 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:33:

```
Pro Glu Ser Ile Phe Asn Ser Leu Tyr Thr Thr Leu Ser Asp Val Trp
    50                      55                  60
Ser Phe Gly Ile
65
```

```
His Arg Asp Leu Ala Ala Arg Asn Val Leu Ile Cys Glu Gly Lys Leu
1               5                   10                  15
Val Lys Ile Cys Asp Phe Gly Leu Ala Arg Asp Ile Met Arg Asp Ser
            20                  25                  30
Asn Tyr Ile Ile Asp Gly Ser Thr Tyr Leu Pro Leu Lys Trp Met Ala
            35                  40                  45
Pro Glu Ser Ile Phe Asn Ser Leu Tyr Thr Thr Leu Ser Asp Val Trp
    50                      55                  60
Ser Phe Gly Ile
65
```

(2) INFORMATION FOR SEQ ID NO:34:

(i) SEQUENCE CHARACTERISTICS:
        (A) LENGTH: 43 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:34:

```
His Arg Asp Leu Ala Ala Arg Asn Val Leu Val Val Lys Ile Asp Phe
1               5                   10                  15
Gly Leu Ala Arg Asp Ile Tyr Gly Leu Pro Lys Trp Met Ala Pro Glu
            20                  25                  30
Ser Tyr Thr Ser Asp Val Trp Ser Phe Gly Val
            35                  40
```

(2) INFORMATION FOR SEQ ID NO:35:

(i) SEQUENCE CHARACTERISTICS:
        (A) LENGTH: 27 base pairs
        (B) TYPE: nucleic acid
        (C) STRANDEDNESS: Not Relevant
        (D) TOPOLOGY: linear (ii) MOLECULE TYPE: protein (xi) SEQUENCE DESCRIPTION: SEQ ID NO:35:

```
GGAATTCCAT CGNGATTTNG CNGCNCG                                  27
```

(2) INFORMATION FOR SEQ ID NO:36:

(i) SEQUENCE CHARACTERISTICS:
        (A) LENGTH: 55 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:36:

| Asn | Cys | Leu | Val | Gly | Glu | Asn | Ile | Ile | Leu | Val | Lys | Val | Ala | Asp | Phe |
|---|---|---|---|---|---|---|---|---|---|---|---|---|---|---|---|
| 1 | | | | 5 | | | | | 10 | | | | | 15 | |
| Gly | Leu | Ser | Arg | Leu | Met | Thr | Gly | Asp | Thr | Tyr | Thr | Ala | Ile | Ile | Ala |
| | | | 20 | | | | | 25 | | | | | 30 | | |
| Gly | Ala | Lys | Phe | Pro | Ile | Lys | Trp | Thr | Ala | Pro | Glu | Ser | Leu | Ala | Tyr |
| | | 35 | | | | | 40 | | | | | 45 | | | |
| Asn | Lys | Phe | Ser | Ile | Lys | Ser | | | | | | | | | |
| | 50 | | | | | 55 | | | | | | | | | |

(2) INFORMATION FOR SEQ ID NO:37:

(i) SEQUENCE CHARACTERISTICS:
(A) LENGTH: 55 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:37:

| Asn | Cys | Leu | Val | Gly | Glu | Asn | Ile | Ile | Val | Val | Lys | Val | Ala | Asp | Phe |
|---|---|---|---|---|---|---|---|---|---|---|---|---|---|---|---|
| 1 | | | | 5 | | | | | 10 | | | | | 15 | |
| Gly | Leu | Ser | Arg | Leu | Met | Thr | Gly | Asp | Thr | Tyr | Thr | Ala | Ile | Ile | Ala |
| | | | 20 | | | | | 25 | | | | | 30 | | |
| Gly | Ala | Lys | Phe | Pro | Ile | Lys | Trp | Thr | Ala | Pro | Glu | Ser | Leu | Ala | Tyr |
| | | 35 | | | | | 40 | | | | | 45 | | | |
| Asn | Thr | Pro | Ser | Ile | Lys | Ser | | | | | | | | | |
| | 50 | | | | | 55 | | | | | | | | | |

(2) INFORMATION FOR SEQ ID NO:38:

(i) SEQUENCE CHARACTERISTICS:
(A) LENGTH: 54 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:38:

| Asn | Cys | Leu | Val | Thr | Glu | Lys | Asn | Val | Leu | Lys | Ile | Ser | Asp | Phe | Gly |
|---|---|---|---|---|---|---|---|---|---|---|---|---|---|---|---|
| 1 | | | | 5 | | | | | 10 | | | | | 15 | |
| His | Ser | Arg | Glu | Glu | Ala | Asp | Gly | Val | Tyr | Ala | Ala | Ser | Gly | Gly | Leu |
| | | | 20 | | | | | 25 | | | | | 30 | | |
| Arg | Gln | Val | Pro | Val | Lys | Trp | Thr | Ala | Pro | Glu | Ala | Leu | Asn | Tyr | Gly |
| | | 35 | | | | | 40 | | | | | 45 | | | |
| Arg | Tyr | Ser | Ser | Glu | Ser | | | | | | | | | | |
| | 50 | | | | | | | | | | | | | | |

(2) INFORMATION FOR SEQ ID NO:39:

(i) SEQUENCE CHARACTERISTICS:
(A) LENGTH: 53 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:39:

Asn Cys Leu Val Gly Glu Asn Asn Thr Leu Lys Ile Ser Asp Phe Gly
1               5                   10                  15

Met Ser Arg Gln Glu Asp Gly Gly Val Tyr Ser Ser Ser Gly Leu Lys
            20                  25                  30

Gln Ile Pro Ile Lys Trp Thr Ala Pro Glu Ala Leu His Tyr Gly Arg
            35                  40                  45

Tyr Ser Ser Glu Ser
50

(2) INFORMATION FOR SEQ ID NO:40:

(i) SEQUENCE CHARACTERISTICS:
(A) LENGTH: 53 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:40:

Asn Cys Leu Val Gly Ser Glu Asn Val Val Lys Val Ala Asp Phe Gly
1               5                   10                  15

Leu Ala Arg Tyr Val Leu Asp Asp Gln Tyr Thr Ser Ser Gly Gly Thr
            20                  25                  30

Lys Phe Pro Ile Lys Trp Ala Pro Pro Glu Val Leu Asn Tyr Thr Arg
            35                  40                  45

Phe Ser Ser Lys Ser
50

(2) INFORMATION FOR SEQ ID NO:41:

(i) SEQUENCE CHARACTERISTICS:
(A) LENGTH: 54 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:41:

Asn Ile Leu Val Asn Gln Asn Leu Cys Cys Lys Val Ser Asp Phe Gly
1               5                   10                  15

Leu Thr Arg Leu Leu Asp Asp Phe Asp Gly Thr Tyr Glu Thr Gln Gly
            20                  25                  30

Gly Lys Ile Pro Ile Arg Trp Thr Ala Pro Glu Ala Leu Ala His Arg
            35                  40                  45

Ile Phe Thr Thr Ala Ser
50

(2) INFORMATION FOR SEQ ID NO:42:

(i) SEQUENCE CHARACTERISTICS:
(A) LENGTH: 55 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:42:

Asn Ile Leu Val Asn Ser Asn Leu Val Cys Lys Val Ser Asp Phe Gly
1               5                   10                  15

Leu Ser Arg Val Leu Glu Asp Asp Pro Glu Ala Thr Tyr Thr Thr Ser
            20                  25                  30

Gly  Gly  Lys  Ile  Pro  Ile  Arg  Trp  Thr  Ala  Pro  Glu  Ala  Ile  Ser  Tyr
                      35                       40                      45

Arg  Lys  Phe  Thr  Ser  Ala  Ser
                      50                       55

( 2 ) INFORMATION FOR SEQ ID NO:43:

( i ) SEQUENCE CHARACTERISTICS:
        ( A ) LENGTH: 57 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:43:

Asn  Ile  Leu  Val  Asn  Ser  Asn  Leu  Val  Cys  Lys  Val  Ser  Asp  Phe  Gly
            1                   5                        10                      15

Leu  Ser  Arg  Tyr  Leu  Gln  Asp  Asp  Thr  Ser  Asp  Pro  Thr  Tyr  Thr  Ser
                            20                      25                      30

Ser  Leu  Gly  Gly  Lys  Ile  Pro  Val  Arg  Trp  Thr  Ala  Pro  Glu  Ala  Ile
                      35                       40                      45

Ala  Tyr  Arg  Lys  Phe  Thr  Ser  Ala  Ser
                      50                       55

( 2 ) INFORMATION FOR SEQ ID NO:44:

( i ) SEQUENCE CHARACTERISTICS:
        ( A ) LENGTH: 54 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:44:

Asn  Val  Leu  Val  Lys  Thr  Pro  Gln  His  Val  Lys  Ile  Thr  Asp  Phe  Gly
            1                   5                        10                      15

Leu  Ala  Lys  Leu  Leu  Gly  Ala  Glu  Glu  Lys  Glu  Tyr  His  Ala  Glu  Gly
                            20                      25                      30

Gly  Lys  Val  Pro  Ile  Lys  Trp  Met  Ala  Leu  Glu  Ser  Ile  Leu  His  Arg
                      35                       40                      45

Ile  Tyr  Thr  His  Gln  Ser
                      50

( 2 ) INFORMATION FOR SEQ ID NO:45:

( i ) SEQUENCE CHARACTERISTICS:
        ( A ) LENGTH: 54 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:45:

Asn  Val  Leu  Val  Lys  Ser  Pro  Asn  His  Val  Lys  Ile  Thr  Asp  Phe  Gly
            1                   5                        10                      15

Leu  Ala  Arg  Leu  Leu  Asp  Ile  Asp  Glu  Thr  Glu  Tyr  His  Ala  Asp  Gly
                            20                      25                      30

Gly  Lys  Val  Pro  Ile  Lys  Trp  Met  Ala  Leu  Glu  Ser  Ile  Leu  Arg  Arg
                      35                       40                      45

Arg  Phe  Thr  His  Gln  Ser 5 0

( 2 ) INFORMATION FOR SEQ ID NO:46:

( i ) SEQUENCE CHARACTERISTICS:
    ( A ) LENGTH: 54 amino acids
    ( B ) TYPE: amino acid
    ( C ) STRANDEDNESS: Not Relevant
    ( D ) TOPOLOGY: linear ( i i ) MOLECULE TYPE: protein ( x i ) SEQUENCE DESCRIPTION: SEQ ID NO:46:

```
Asn  Val  Leu  Val  Thr  Glu  Asn  Asn  Val  Met  Lys  Ile  Ala  Asp  Phe  Gly
 1                    5                   10                               15

Leu  Ala  Arg  Asp  Ile  His  His  Ile  Asp  Tyr  Tyr  Lys  Lys  Thr  Thr  Asn
              20                        25                        30

Gly  Arg  Leu  Pro  Val  Lys  Trp  Met  Ala  Pro  Glu  Ala  Leu  Phe  Asp  Arg
              35                        40                        45

Ile  Tyr  Thr  His  Gln  Ser
              50
```

( 2 ) INFORMATION FOR SEQ ID NO:47:

( i ) SEQUENCE CHARACTERISTICS:
    ( A ) LENGTH: 54 amino acids
    ( B ) TYPE: amino acid
    ( C ) STRANDEDNESS: Not Relevant
    ( D ) TOPOLOGY: linear ( i i ) MOLECULE TYPE: protein ( x i ) SEQUENCE DESCRIPTION: SEQ ID NO:47:

```
Asn  Val  Leu  Val  Thr  Glu  Asn  Asn  Val  Met  Lys  Ile  Ala  Asp  Phe  Gly
 1                    5                   10                               15

Leu  Ala  Arg  Asp  Ile  Asn  Asn  Ile  Asp  Tyr  Tyr  Lys  Lys  Thr  Thr  Asn
              20                        25                        30

Gly  Arg  Leu  Pro  Val  Lys  Trp  Met  Ala  Pro  Glu  Ala  Leu  Phe  Asp  Arg
              35                        40                        45

Val  Tyr  Thr  His  Gln  Ser
              50
```

( 2 ) INFORMATION FOR SEQ ID NO:48:

( i ) SEQUENCE CHARACTERISTICS:
    ( A ) LENGTH: 54 amino acids
    ( B ) TYPE: amino acid
    ( C ) STRANDEDNESS: Not Relevant
    ( D ) TOPOLOGY: linear ( i i ) MOLECULE TYPE: protein ( x i ) SEQUENCE DESCRIPTION: SEQ ID NO:48:

```
Asn  Val  Leu  Leu  Ala  Gln  Gly  Lys  Ile  Val  Lys  Ile  Cys  Asp  Phe  Gly
 1                    5                   10                               15

Leu  Ala  Arg  Asp  Ile  Met  His  Asp  Ser  Asn  Thr  Val  Ser  Lys  Gly  Ser
              20                        25                        30

Thr  Phe  Leu  Pro  Val  Lys  Trp  Met  Ala  Pro  Glu  Ser  Ile  Phe  Asp  Asn
              35                        40                        45

Leu  Thr  Tyr  Tyr  Leu  Ser
              50
```

( 2 ) INFORMATION FOR SEQ ID NO:49:

( i ) SEQUENCE CHARACTERISTICS:
  ( A ) LENGTH: 54 amino acids
  ( B ) TYPE: amino acid
  ( C ) STRANDEDNESS: Not Relevant
  ( D ) TOPOLOGY: linear ( i i ) MOLECULE TYPE: protein ( x i ) SEQUENCE DESCRIPTION: SEQ ID NO:49:

```
Asn Met Leu Ile Cys Glu Gly Lys Leu Val Lys Ile Cys Asp Phe Gly
1               5                   10                  15
Leu Ala Arg Asp Ile Met Arg Asp Ser Asn Tyr Ile Ser Lys Gly Ser
            20                  25                  30
Thr Phe Leu Pro Leu Lys Trp Met Ala Pro Glu Ser Ile Phe Asn Ser
        35                  40                  45
Leu Tyr Thr Thr Leu Ser
50
```

( 2 ) INFORMATION FOR SEQ ID NO:50:

( i ) SEQUENCE CHARACTERISTICS:
    ( A ) LENGTH: 54 amino acids
    ( B ) TYPE: amino acid
    ( C ) STRANDEDNESS: Not Relevant
    ( D ) TOPOLOGY: linear ( i i ) MOLECULE TYPE: protein ( x i ) SEQUENCE DESCRIPTION: SEQ ID NO:50:

```
Asn Val Leu Leu Thr Ser Gly His Val Ala Lys Ile Gly Asp Phe Gly
1               5                   10                  15
Leu Ala Arg Asp Ile Met Asn Asp Ser Asn Tyr Val Val Lys Gly Asn
            20                  25                  30
Ala Arg Leu Pro Val Lys Trp Met Ala Pro Glu Ser Ile Phe Asp Cys
        35                  40                  45
Val Tyr Thr Tyr Gln Ser
50
```

( 2 ) INFORMATION FOR SEQ ID NO:51:

( i ) SEQUENCE CHARACTERISTICS:
    ( A ) LENGTH: 54 amino acids
    ( B ) TYPE: amino acid
    ( C ) STRANDEDNESS: Not Relevant
    ( D ) TOPOLOGY: linear ( i i ) MOLECULE TYPE: protein ( x i ) SEQUENCE DESCRIPTION: SEQ ID NO:51:

```
Asn Ile Leu Leu Ser Glu Asn Asn Val Val Lys Ile Cys Asp Phe Gly
1               5                   10                  15
Leu Ala Arg Asp Ile Tyr Lys Asn Pro Asp Tyr Val Arg Arg Gly Asp
            20                  25                  30
Thr Arg Leu Pro Leu Lys Trp Met Ala Pro Glu Ser Ile Phe Asp Lys
        35                  40                  45
Val Tyr Ser Thr Lys Ser
50
```

( 2 ) INFORMATION FOR SEQ ID NO:52:

( i ) SEQUENCE CHARACTERISTICS:
    ( A ) LENGTH: 54 amino acids
    ( B ) TYPE: amino acid
    ( C ) STRANDEDNESS: Not Relevant
    ( D ) TOPOLOGY: linear (ii) MOLECULE TYPE: protein (xi) SEQUENCE DESCRIPTION: SEQ ID NO:52:

| Asn | Cys | Leu | Val | Gly | Gln | Gly | Leu | Val | Val | Lys | Ile | Gly | Asp | Phe | Gly |
|---|---|---|---|---|---|---|---|---|---|---|---|---|---|---|---|
| 1 | | | | 5 | | | | | 10 | | | | | 15 | |

| Met | Ser | Arg | Asp | Ile | Tyr | Ser | Thr | Asp | Tyr | Tyr | Arg | Val | Gly | Gly | Arg |
|---|---|---|---|---|---|---|---|---|---|---|---|---|---|---|---|
| | | | 20 | | | | | 25 | | | | | | 30 | |

| Thr | Met | Leu | Pro | Ile | Arg | Trp | Met | Pro | Pro | Glu | Ser | Ile | Leu | Tyr | Arg |
|---|---|---|---|---|---|---|---|---|---|---|---|---|---|---|---|
| | | 35 | | | | | 40 | | | | | 45 | | | |

| Lys | Phe | Thr | Thr | Glu | Ser |
|---|---|---|---|---|---|
| | | 50 | | | |

(2) INFORMATION FOR SEQ ID NO:53:

(i) SEQUENCE CHARACTERISTICS:
(A) LENGTH: 54 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:53:

| Asn | Cys | Leu | Val | Gly | Glu | Asn | Leu | Leu | Val | Lys | Ile | Gly | Asp | Phe | Gly |
|---|---|---|---|---|---|---|---|---|---|---|---|---|---|---|---|
| 1 | | | | 5 | | | | | 10 | | | | | 15 | |

| Met | Ser | Arg | Asp | Val | Tyr | Ser | Thr | Asp | Tyr | Tyr | Arg | Val | Gly | Gly | Arg |
|---|---|---|---|---|---|---|---|---|---|---|---|---|---|---|---|
| | | | 20 | | | | | 25 | | | | | | 30 | |

| Thr | Met | Leu | Pro | Ile | Arg | Trp | Met | Pro | Pro | Glu | Ser | Ile | Met | Tyr | Arg |
|---|---|---|---|---|---|---|---|---|---|---|---|---|---|---|---|
| | | 35 | | | | | 40 | | | | | 45 | | | |

| Lys | Phe | Thr | Thr | Glu | Ser |
|---|---|---|---|---|---|
| | | 50 | | | |

(2) INFORMATION FOR SEQ ID NO:54:

(i) SEQUENCE CHARACTERISTICS:
(A) LENGTH: 54 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:54:

| Asn | Cys | Met | Val | Ala | Glu | Asp | Phe | Thr | Val | Lys | Ile | Gly | Asp | Phe | Gly |
|---|---|---|---|---|---|---|---|---|---|---|---|---|---|---|---|
| 1 | | | | 5 | | | | | 10 | | | | | 15 | |

| Met | Thr | Arg | Asp | Ile | Tyr | Glu | Thr | Asp | Tyr | Tyr | Arg | Lys | Gly | Gly | Lys |
|---|---|---|---|---|---|---|---|---|---|---|---|---|---|---|---|
| | | | 20 | | | | | 25 | | | | | | 30 | |

| Gly | Leu | Leu | Pro | Val | Arg | Trp | Met | Ser | Pro | Glu | Ser | Leu | Lys | Asp | Gly |
|---|---|---|---|---|---|---|---|---|---|---|---|---|---|---|---|
| | | 35 | | | | | 40 | | | | | 45 | | | |

| Val | Phe | Thr | Thr | His | Ser |
|---|---|---|---|---|---|
| | | 50 | | | |

TYRO-3 PROTEIN TYROSINE KINASE

This is a divisional of application Ser. No. 08/237,401, filed May 2, 1994, which is a continuation of Ser. No. 07/884,486, filed May 15, 1992, now abandoned.

This work was supported by Grant Number NS-23896 from the National Institutes of Health. The United States Government may retain certain rights of this invention.

BACKGROUND OF THE INVENTION

1. Field of the Invention

This invention relates generally to the molecular cloning of genes which encode unique protein-tyrosine kinase receptor subtypes which can be used in an assay to screen various compositions which modulate these receptors.

2. Related Art

Among the signal transduction molecules implicated in neural development, the receptor protein-tyrosine kinases (PTKs) are of particular interest: These proteins function as transmembrane receptors for polypeptide growth factors, and contain a tyrosine kinase as an integral part of their cytoplasmic domains (Yarden and Ullrich, *Annu.Rev.Biochem.*, 57:443–478, 1988; Ullrich and Schlessinger, *Cell*, 61:203–212, 1990). Binding of a polypeptide ligand to its corresponding cell surface receptor results in rapid activation of that receptor's intracellular tyrosine kinase, which in turn results in the tyrosine phosphorylation of the receptor itself and of multiple downstream target proteins (Hunter and Cooper, *Annu. Rev. Biochem.*, 54:897–930, 1985; Hunter, et al, eds. J. B. Hook and G. Poste, Plenum Press, New York and London, pp. 119–139, 1990). For many receptor PTKs, growth factor binding ultimately triggers multiple rounds of cell division.

Molecular studies of mutations that affect cell differentiation have demonstrated that several of these receptor PTKs act as early determinants of cell fate. Loss-of-function mutations in the sevenless gene of Drosophila (Harris, et al., *J. Physiol.*, 256:415–439, 1976), for example, abolish the tyrosine kinase activity of a transmembrane receptor expressed in the developing ommatidia of the eye and result in the aberrant differentiation of the precursors to the number 7 photoreceptors (Basler and Haten, *Cell*, 54:299–311, 1988; Rubin, *Cell*, 57:519–520, 1989). Rather than becoming number 7 photoreceptor cells, these precursors instead differentiate into non-neuronal cone cells, which form the lens. In marked contrast, the remaining complement of photoreceptors (numbers 1–6 and 8) differentiate normally.

Mutations in genes encoding other receptor PTKs have also been shown to affect cell differentiation. For example, mutations in the torso gene of Drosophila specifically disrupt the terminal differentiation of extreme anterior and posterior structures in the embryo (Sprenger, et al., *Nature* 338:478–483, 1989), and mutations in the Drosophila Ellipse gene, which encodes a homolog of the mammalian epidermal growth factor (EGF) receptor, result in the developmental failure of multiple cell types in the eye (Baker and Rubin, *Nature*, 340:150–153, 1989). In vertebrates, mutations in the mouse dominant white spotting locus (W), which encodes the c-kit receptor PTK, produce pleiotropic developmental effects that include disruption of the normal proliferation and differentiation of neural crest-derived melanocytes (Chabot, et al., *Nature*, 335:88–89, 1988; Geissler, et al., *Cell*, 55:185–192, 1988).

Parallel to these studies of the developmental role of receptor PTKs has been the demonstration that many of the ligands for these receptors influence the differentiation of neural cells in culture. Platelet-derived growth factor (PDGF), for example, has been shown to stimulate the proliferation and prevent the premature differentiation of oligodendrocyte/type-2 astrocyte glial progenitor cells in rat optic nerve cultures (Noble, et al., *Nature*, 333:560–562, 1988; Raff, et al., *Nature*, 333:562–565, 1988).

Similarly, both acidic and basic fibroblast growth factor (bFGF) have been shown to stimulate the neuronal differentiation of cultured rat pheochromocytoma (PC-12) cells (Togari, et al., *J. Neurosci.*, 5:307–316, 1985; Wagner and D'Amore, *J. Cell Biol.*, 103:1363–1367,1986). bFGF has also been reported to prolong survival and stimulate neurite outgrowth in cultures of primary cortical and hippocampal neurons (Morrison, et al., *Proc. Natl. Acad. Sci. USA*, 83:7537–7541, 1986; Walicke, et al., *Proc. Natl. Acad. Sci. USA*, 83:3012–3016, 1986), to induce cell division, neuronal differentiation, and nerve growth factor (NGF) dependence in adrenal chromatifin cells (Stemple, et al., *Neuron*, 1:517–525, 1988), and to function as a survival factor, both in vivo and in vitro, for neural crest-derived non-neuronal cells during the early development of sensory ganglia (Kalcheim, *Dev. Biol.*, 134:1–10,1989). Recently, the product of the mouse mutant steel gene (SI), which interacts genetically with W, has been identified as a growth factor ligand for the c-kit receptor (Witte, *Cell*, 63:5–6, 1990). Genetic and biochemical studies of the expression patterns of the sevenless, torso and c-kit receptors suggest that specification of cell fates can be achieved through the spatially and temporally restricted expression of either the receptors or their ligands (Rubin, *Cell*, 57:519–520, 1989; Tomlinson and Ready, *Biol.*, 120:366–376, 1987; Reinke and Zipursky, *Cell*, 55:321–330, 1988; Banerjee and Zipursky, *Neuron*, 4:177–187, 1990; Stevens, et al., *Nature*, 346:660–663, 1990; Matsui, et al., *Nature*, 347:667–669, 1990).

SUMMARY OF THE INVENTION

In accordance with the present invention, novel receptor protein tyrosine kinase (PTK) subtype polypeptides have been isolated. These PTKs possess a tyrosine kinase domain and a unique tissue expression pattern different from all previously known receptor PTKs. These novel receptor PTK subtypes have been designated tyro-1 through tyro-8 and tyro-10 through tyro-12. Of particular interest among the new PTK subtypes are tyro-1 through tyro-6 which are found predominantly or exclusively in neural tissue.

By providing the polynucleotide sequences and corresponding polypeptide sequences for the new PTK subtypes, it is now possible to obtain polynucleotide sequences encoding the entire receptor PTK for each of the subtypes.

Further, the invention provides a method for identifying compositions which potentially affect the activity of the receptor PTK subtype. This method comprises (a) contacting cells containing DNA which expresses the PTK polypeptide with the composition under conditions suitable for cell culture; and (b) monitoring the cells for a physiological change resulting from this interaction.

In addition, the present invention provides unique oligonucleotide which align with the unique flanking regions of the receptor PTK subtypes, thereby allowing amplification of the polynucleotides encoding the receptor PTK subtype by such techniques as polymerase chain reaction (PCR).

The present invention also provides a method of gene therapy comprising introducing into a host subject an expression vector comprising a nucleotide sequence encoding a receptor PTK subtype capable of affecting a biological activity of the host subject cell.

DETAILED DESCRIPTION OF THE PREFERRED EMBODIMENT

Figure 1A:
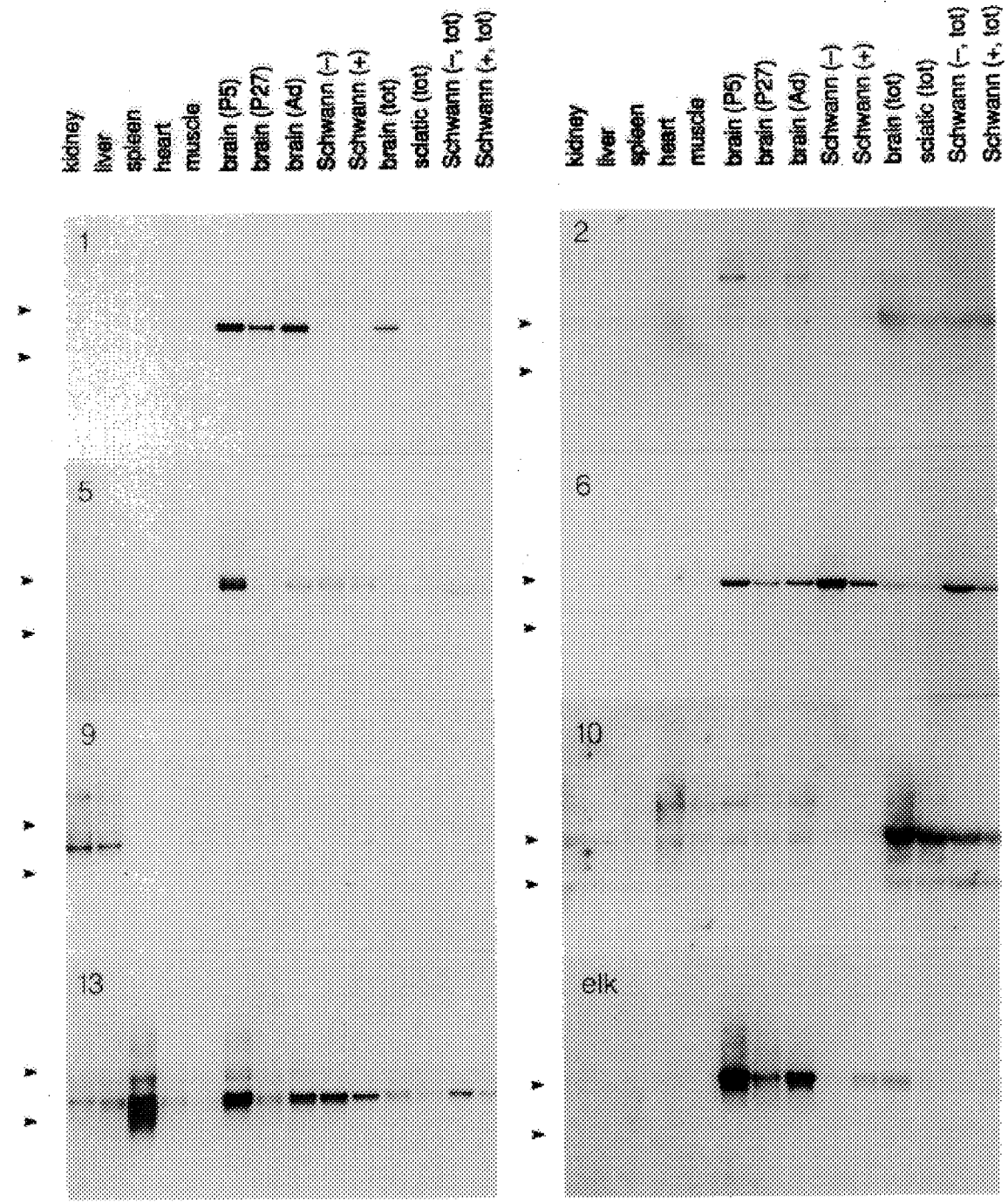
FIGS. 1A and 1B show the tissue expression profiles of the novel PTK mRNAs.

The present invention relates to novel protein tyrosine kinase (PTK) gene and polypeptides encoded by these genes. Various of these PTK subtypes are implicated in neural development where they function primarily as signal transduction molecules. The receptor PTKs of the invention are characterized as having a tyrosine kinase domain and a unique tissue expression pattern which differs from that of all known receptor PTKs.

The invention provides polynucleotides, such as DNA, cDNA, and RNA, encoding novel receptor PTK polypeptides. It is understood that all polynucleotides encoding all or a portion of the receptor PTKs of the invention are also included herein, so long as they exhibit at least one protein tyrosine kinase domain and the tissue expression pattern characteristic of a given subtype. Such polynucleotides include both naturally occurring and intentionally manipulated, for example, mutagenized polynucleotides.

DNA sequences of the invention can be obtained by several methods. For example, the DNA can be isolated using hybridization procedures which are well known in the art. These include, but are not limited to: 1) hybridization of probes to genomic or cDNA libraries to detect shared nucleotide sequences and 2) antibody screening of expression libraries to detect shared structural features.

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucleic Acid Research*, 9:879, 1981).

A receptor PTK cDNA library can be screened by injecting the various cDNAs into oocytes, allowing sufficient time for expression of the cDNA gene products to occur, and testing for the presence of the desired cDNA expression product, for example, by using antibody specific for the receptor PTK subtype polypeptide or by using functional assays for receptor PTK subtype activity and a tissue expression pattern characteristic of the desired subtype.

Alternatively, a cDNA library can be screened indirectly for receptor PTK polypeptides having at least one epitope using antibodies specific for receptor PTK subtypes of the invention. Such antibodies can be either polyclonally or monoclonally derived and used to detect expression product indicative of the presence of protein tyrosine kinase receptor PTK subtype cDNA.

The development of specific DNA sequences encoding receptor PTK subtypes of the invention can also be obtained by: (1) isolation of a double-stranded DNA sequence from the genomic DNA; (2) chemical manufacture of a DNA sequence to provide the necessary codons for the polypeptide of interest; and (3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Specifically embraced in (1) are genomic DNA sequences which encode allelic variant forms. Also included are DNA sequences which are degenerate as a result of the genetic code.

Of the three above-noted methods for developing specific DNA sequences for use in recombinant procedures, the use of genomic DNA isolates (1), is the least common. This is especially true when it is desirable to obtain the microbial expression of mammalian polypeptides because of the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the formation of cDNA sequences. Among the standard procedures for isolating cDNA sequences of interest is the formation of plasmid-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucleic Acid Research*, 11:2325, 1983).

Since the novel DNA sequences of the invention encode essentially all or part of a receptor PTK, it is now a routine matter to prepare, subclone, and express smaller polypeptide fragments of DNA from this or corresponding DNA sequences. Alternatively, by utilizing the DNA fragments disclosed herein which define the unique tyrosine kinase receptor subtype of the invention it is possible, in conjunction with known techniques, to determine the DNA sequences encoding the entire receptor subtypes. Such techniques are described in U.S. Pat. No. 4,394,443 and U.S. Pat. No. 4,446,235 which are incorporated herein by reference.

The polypeptide resulting from expression of a DNA sequence of the invention can be further characterized as being free from association with other eukaryotic polypeptides or other contaminants which might otherwise be associated with the protein kinase in its natural cellular environment.

Isolation and purification of microbially expressed polypeptides provided by the invention may be by conventional means including, preparative chromatographic separations and immunological separations involving monoclonal and/or polyclonal antibody preparation.

For purposes of the present invention, receptor PTK subtypes which are homologous to those of the invention can be identified by structural as well as functional similarity. Structural similarity can be determined, for example, by assessing polynucleotide strand hybridization or by screening with antibody, especially a monoclonal antibody, which recognizes a unique epitope present on the subtypes of the invention. When hybridization is used as criteria to establish structural similarity, those polynucleotide sequences which hybridize under stringent conditions to the polynucleotides of the invention are considered to be essentially the same as the polynucleotide sequences of the invention.

In the present invention, polynucleotide sequences encoding receptor PTK subtype may be introduced into a host cell by means of a recombinant expression vector. The term "recombinant expression vector" refers to a plasmid, virus or other vehicle known in the art that has been manipulated by insertion or incorporation of the polynucleotide sequences of the invention. Such expression vectors typically contain a promotor sequence which facilitates efficient transcription of the inserted sequence in the host. The expression vector also typically contains specific genes which allow phenotypic selection of the transformed cells. Alternatively, nucleotide sequences encoding a receptor PTK subtype can be introduced directly in the form of free nucleotide, for example, by microinjection, or transfection.

DNA sequences encoding receptor PTK subtypes of the invention can be expressed in vivo by DNA transfer into a suitable host cell. "Recombinant host cells" or "host cells" are cells in which a vector can be propagated and its DNA expressed. The term includes not only prokaryotes, but also such eukaryotes as yeast, filamentous fungi, as well as animal cells which can replicate and express an intron-free DNA sequence of the invention and any progeny of the subject host cell. It is understood that not all progeny are identical to the parental cell since there may be mutations that occur at replication. However, such progeny are included when the terms above are used.

Methods of expressing DNA sequences having eukaryotic coding sequences in prokaryotes are well known in the art. Biologically functional viral and plasmid DNA vectors capable of expression and replication in a host are known in the art. Such vectors are used to incorporate DNA sequences of the invention. Hosts include microbial, yeast and mammalian organisms.

Transformation of a host cell with recombinant DNA may be carried out by conventional techniques which are well known to those skilled in the art. Where the host is prokaryotic, such as *E. coli*, competent cells which are capable of DNA uptake can be prepared from cells harvested after exponential growth phase and subsequently treated by the $CaCl_2$ method well known in the art. Alternatively, $MgCl_2$ or RbCl can be used. Transformation can also be performed after forming a protoplast of the host cell.

When the host is a eukaryote, such methods of transfection of DNA as calcium phosphate co-precipitates, conventional mechanical procedures such as microinjection, insertion of a plasmid encased in liposomes, or virus vectors may be used. Eukaryotic cells can also be cotransformed with foreign cDNA encoding the desired receptor PTK subtype protein, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982).

Where the eukaryotic host cells are yeast, the cDNA can be expressed by inserting the cDNA into appropriate expression vectors and introducing the product into the host cells. Various shuttle vectors for the expression of foreign genes in yeast have been reported (Heinemann, et al., *Nature*, 340:205, 1989; Rose, et al., *Gene*, 60:237, 1987).

Isolation and purification of microbially expressed protein, or fragments thereof provided by the invention, may be carried out by conventional means including preparative chromatography and immunological separations involving monoclonal or polyclonal antibodies. Antibodies provided in the present invention are immunoreactive with the receptor PTK subtypes of the invention. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature*, 256:495, 1975; *Current Protocols in Molecular Biology*, Ausubel, et al., ed., 1989).

Minor modifications of the receptor PTK primary amino acid sequence may result in proteins which have substantially equivalent activity compared to the receptor PTKs described herein. Such modifications may be deliberate, as by site-directed mutagenesis, or may be spontaneous. All proteins produced by these modifications are included herein as long as tyrosine kinase activity and the characteristic tissue expression pattern for the subtype is present.

The invention also discloses a method for identifying a composition which affects the activity of a receptor PTK subtype of the invention. The receptor is, for example, capable of affecting cell division and/or differentiation. The composition is incubated in combination with cells under conditions suitable for cell culture, then subsequently monitoring the cells for a physiologic change.

The production of a receptor PTK can be accomplished by oligonucleotide(s) which are primers for amplification of the genomic polynucleotide encoding PTK receptor. These unique oligonucleotide primers were produced based upon identification of the flanking regions contiguous with the polynucleotide encoding the receptor PTK. These oligonucleotide primers comprise sequences which are capable of hybridizing with the flanking nucleotide sequence encoding a polypeptide having amino acid residues HRDLAAR and/or DVWS(F/Y)G(V/I) and sequences complementary thereto.

The primers of the invention embrace oligonucleotides of sufficient length and appropriate sequence so as to provide specific initiation of polymerization on a significant number of nucleic acids in the polynucleotide encoding the receptor PTK subtype. Specifically, the term "primer" as used herein refers to a sequence comprising two or more deoxyribonucleotides or ribonucleotides, preferably more than three, which sequence is capable of initiating synthesis of a primer extension product, which is substantially complementary to a receptor PTK strand. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxyribo-nucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 15–22 or more nucleotides, although it may contain fewer nucleotides.

Primers of the invention are designed to be "substantially" complementary to each strand of polynucleotide encoding the receptor PTK to be amplified. This means that the primers must be sufficiently complementary to hybridize with their respective strands under conditions which allow the agent for polymerization to perform. In other words, the primers should have sufficient complementarity with the flanking sequences to hybridize therewith and permit amplification of the polynucleotide encoding the receptor PTK Preferably, the primers have exact complementarity with the flanking sequence strand.

Oligonucleotide primers of the invention are employed in the amplification process which is an enzymatic chain reaction that produces exponential quantities of polynucleotide encoding the receptor PTK relative to the number of reaction steps involved. Typically, one primer is complementary to the negative (−) strand of the polynucleotide encoding the receptor PTK and the other is complementary to the positive (+) strand. Annealing the primers to denatured nucleic acid followed by extension with an enzyme, such as the large fragment of DNA Polymerase I (Klenow) and nucleotides, results in newly synthesized + and −strands containing the receptor PTK sequence. Because these newly synthesized sequences are also templates, repeated cycles of denaturing, primer annealing, and extension results in exponential production of the region (i.e., the tyrosine kinase receptor polynucleotide sequence) defined by the primer. The product of the chain reaction is a discrete nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (*Tetrahedron Letters,* 22:1859–1862, 1981). One method for synthesizing oligonucleotides on a modified solid support is described in U.S. Pat. No. 4,458,066.

Any nucleic acid specimen, in purified or nonpurified form, can be utilized as the starting nucleic acid or acids, provided it contains, or is suspected of containing, the specific nucleic acid sequence containing a protein receptor PTK of the invention. Thus, the process may employ, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the receptor PTK, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

DNA or RNA utilized herein may be extracted from a body sample, such as brain, or various other tissue, by a variety of techniques such as that described by Maniatis, et al. (*Molecular Cloning,* 280:281, 1982). If the extracted sample is impure (such as plasma, serum, or blood), it may be treated before amplification with an amount of a reagent effective to open the cells, fluids, tissues, or animal cell membranes of the sample, and to expose and/or separate the strand(s) of the nucleic acid(s). This lysing and nucleic acid denaturing step to expose and separate the strands will allow amplification to occur much more readily.

Where the target nucleic acid sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means, the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling (*CSH-Quantitative Biology,* 43:63, 1978) and techniques for using RecA are reviewed in C. Radding (*Ann. Rev. Genetics,* 16:405–437,1982).

If the nucleic acid containing the sequence to be amplified is single stranded, its complement is synthesized by adding one or two oligonucleotide primers. If a single primer is utilized, a primer extension product is synthesized in the presence of primer, an agent for polymerization, and the four nucleoside triphosphates described below. The product will be partially complementary to the single-stranded nucleic acid and will hybridize with a single-stranded nucleic acid to form a duplex of unequal length strands that may then be separated into single strands to produce two single separated complementary strands. Alternatively, two primers may be added to the single-stranded nucleic acid and the reaction carried out as described.

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7–9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

The deoxyribonucleotide triphosphates dATP, dCTP, dGTP, and dTTP are added to the synthesis mixture, either separately or together with the primers, in adequate amounts and the resulting solution is heated to about 90°–100° C.

from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions.

Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, E. coli DNA polymerase I, Klenow fragment of E. coli DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each receptor PTK nucleic acid strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

The newly synthesized receptor PTK strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The above process is repeated on the single-stranded molecules. Additional agent for polymerization, nucleotides, and primers may be added, if necessary, for the reaction to proceed under the conditions prescribed above. Again, the synthesis will be initiated at one end of each of the oligonucleotide primers and will proceed along the single strands of the template to produce additional nucleic acid. After this step, half of the extension product will consist of the specific nucleic acid sequence bounded by the two primers.

The steps of denaturing and extension product synthesis can be repeated as often as needed to amplify the receptor PTK nucleic acid sequence to the extent necessary for detection. The amount of the specific nucleic acid sequence produced will accumulate in an exponential fashion.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et al., Bio/Technology, 3:1008–1012, 1985), allele-specific oligonucleotide (ASO) probe analysis (Conner, et al., Proc. Natl. Acad. Sci. USA, 80:278, 1983), oligonucleotide ligation assays (OLAs) (Landegren, et al., Science, 241:1077, 1988), and the like. Molecular techniques for DNA analysis have been reviewed (Landegren, et al., Science, 242:229–237, 1988).

The present invention also provides methods for the treatment of disease employing gene therapy that modulates cellular differentiation or maturation. Such therapy can be affected by introduction of polynucleotide sequences of the invention into cells of a subject having a disease. Delivery of polynucleotide can be achieved using techniques well known in the art. For example, a recombinant expression vector, such as a chimeric virus, or a colloidal dispersion system can be employed.

Various viral vectors which can be utilized for introduction of polynucleotide according to the present invention, include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can incorporate a gene for a selectable marker so that transduced cells can be identified and generated.

By inserting a polynucleotide encoding the receptor PTK of interest into a viral vector, along with another gene which encodes ligand for a receptor on a specific target cell, the vector now becomes target specific. Retroviral vectors can be made target specific by including in the retroviral vector a polynucleotide encoding a target related binding substance. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the receptor PTK polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to, $\psi$2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for introduction of polynucleotides encoding the receptor PTKs of the invention is a colloidal dispersion system. Colloidal dispersion systems include macromolecular complexes, nanocapsules, microspheres, beads, and lipid-based systems including oil-in-water emulsions, micelles, mixed micelles, and liposomes. The preferred colloidal system of this invention is a liposome.

Since the receptor PTK polypeptide may be indiscriminate in its action with respect to cell type, a targeted delivery system offers a significant improvement over randomly injected non-specific liposomes. A number of procedures can be used to covalently attach either polyclonal or monoclonal antibodies to a liposome bilayer. Antibody-targeted liposomes can include monoclonal or polyclonal antibodies or fragments thereof such as Fab, or F(ab')$_2$, as long as they bind efficiently to an epitope on the target cells. Liposomes may also be targeted to cells expressing receptors for hormones or other serum factors.

Liposomes are artificial membrane vesicles which are useful as in vitro and in vivo delivery vehicles. It has been shown that large unilamellar vesicles (LUV), which range in size from 0.2–4.0 μm can encapsulate a substantial percentage of an aqueous buffer containing large macromolecules. RNA, DNA, intact virions and peptides can be encapsulated within the aqueous interior and be delivered to cells in a biologically active form (Fraley, et al., *Trends Biochem. Sci.*, 6:77,1981). In order for a liposome to be an efficient transfer vehicle, the following characteristics should be present: (1) encapsulation of polynucleotides of interest at high efficiency without compromising biological activity; (2) preferential and substantial binding to target cells relative to non-target cells; (3) delivery of aqueous contents of vesicle to the target cell cytoplasm at high efficiency; and (4) accurate and effective expression of genetic information (Mannino, et al., *Biotechniques,* 6:682, 1988).

The surface of the targeted delivery system may be modified in a variety of ways. In the case of a liposomal targeted delivery system, lipid groups can be incorporated into the lipid bilayer of the liposome in order to maintain the targeting receptor in stable association with the liposomal bilayer. Various linking groups can be used for joining the lipid chains to the targeting receptor.

In general, the targeted delivery system will be directed to cell surface receptors thereby allowing the delivery system to find and "home in" on the desired cells. Alternatively, the delivery system can be directed to any cell surface molecule preferentially found in the cell population for which treatment is desired and capable of association with the delivery system. Antibodies can be used to target liposomes to specific cell-surface molecules. For example, where a tumor is associated with a receptor PTK of the invention, certain antigens expressed specifically or predominantly on the cells of the tumor may be exploited for the purpose of targeting antibody tyrosine kinase receptor DNA-containing liposomes directly to a malignant tumor, if desired.

An alternative use for recombinant retroviral vectors comprises the introduction of polynucleotide sequences into the host by means of skin transplants of cells containing the virus. Long term expression of foreign genes in implants, using cells of fibroblast origin, may be achieved if a strong housekeeping gene promoter is used to drive transcription. For example, the dihydrofolate reductase (DHFR) gene promoter may be used. Cells such as fibroblasts, can be infected with virions containing a retroviral construct containing the receptor PTK gene of interest together with a gene which allows for specific targeting, such as a tumor-associated antigen and a strong promoter. The infected cells can be embedded in a collagen matrix which can be grafted into the connective tissue of the dermis in the recipient subject. As the retrovirus proliferates and escapes the matrix it will specifically infect the target cell population. In this way the transplantation results in increased amounts of receptor PTK being produced in cells manifesting the disease.

Because the present invention identifies nucleotide sequences encoding novel receptor PTKs, it is possible to design therapeutic or diagnostic protocols utilizing these sequences. Thus, where a disease is associated with a receptor PTK of the invention, the polynucleotide sequence encoding the PTK can be utilized to design sequences which interfere with the function of the receptor. This approach utilizes, for example, antisense nucleic acid and ribozymes to block translation of specific receptor mRNA, either by masking the mRNA with antisense nucleic acid or by cleaving it with ribozyme.

Antisense nucleic acids are DNA or RNA molecules that are complementary to at least a portion of a specific mRNA molecule (Weintraub, *Scientific American,* 262:40, 1990). In the cell, the antisense nucleic acids hybridize to the corresponding mRNA, forming a double-stranded molecule. The antisense nucleic acids interfere with the translation of the mRNA since the cell will not translate a mRNA that is double-stranded. Antisense oligomers of about 15 nucleotides are preferred, since they are easily synthesized and are less likely to cause problems than larger molecules when introduced into the target receptor-producing cell. The use of antisense methods to inhibit the in vitro translation of genes is well known in the art (Marcus-Sakura, *Anal.Biochem.,* 172:289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.,* 260:3030, 1988). A major advantage of this approach is that, because they are sequence-specific, only mRNAs with particular sequences are inactivated.

There are two basic types of ribozymes namely, tetrahymena-type (Hasselhoff, *Nature,* 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

Antisense sequences can be therapeutically administered by techniques as described above for the administration of receptor PTK polynucleotides. Targeted liposomes are especially preferred for therapeutic delivery of antisense sequences.

The following Examples are intended to illustrate, but not to limit the invention. While such Examples are typical of those that might be used, other procedures known to those skilled in the art may alternatively be utilized.

EXAMPLE 1

ISOLATION OF NOVEL PTK CLONES

PCR was used to amplify PTK-related sequences located between the degenerate oligonucleotide primer sequences shown in TABLE 1. These primers correspond to the amino acid sequences HRDLAAR (SEQ ID NO:27) (upstream) and DVWS(F/Y)G(I/V) (SEQ ID NO:28) (downstream), which flank a highly conserved region of the kinase domain shared by receptor PTKs (Hanks, et al., Science, 241:42–52, 1988). The upstream primer was chosen to exclude members of the src family of cytoplasmic tyrosine kinases. The downstream primer was chosen such that a second highly conserved amino acid sequence diagnostic or PTKs-P(I/V) (K/R)W(T/M)APE (SEQ ID NO:29)—would be contained within amplified PCR products.

The DNA substrates used for amplification were sciatic nerve cDNA populations prepared for use in the construction of subtracted cDNA libraries. Three different subtracted cDNAs were produced. The first two, UN and TWI, were enriched for transcripts expressed predominantly in Schwann cells. The third, BD, was enriched for transcripts shared between Schwann cells and myelinating stage (P17–23) brain. Two initial hybridizations were performed. Both samples contained 500 ng of single-stranded sciatic nerve cDNA mixed with the following poly(A)-selected RNAs: 10 µg of muscle, 7.5 µg of liver, and 5 µg of kidney.

Both samples also contained a series of RNAs synthesized in vitro; these encoded portions of the sense strand of the following Schwann cell transcripts: NGF receptor, glial fibrillary acidic protein, proteolipid protein, protein zero, myelin basic protein, and CNPase. The first sample contained, in addition, 10 µg of poly(A)-selected RNA from rat brain cerebellum (P19) and cortex (P3). Each hybridization was allowed to proceed to approximately $R_o t$ 2000. Following hybridization, these samples were bound to hydroxylapatite (0.12M phosphate buffer, 65° C.). For the first sample, material not binding to hydroxylapatite (HAP) was collected and converted to a double-stranded form. This material was designated UN (unbound). For the second sample, cDNA not binding to the column was further hybridized with 40 µg of poly(A)-selected RNA from rat cerebellum (equal mix of P17 and P23) until $R_o t$ 800. This mixture was re-applied to hydroxylapatite. The unbound material was collected and converted to a double-stranded form and designated TWI (twice unbound). The material that bound to the HAP column was then eluted and also converted to a double-stranded DNA form. This fraction was called BD (bound).

Approximately 2–4 ng of the UN and TWI subtract cDNAs and 1 ng of the BD cDNA were used in each of the amplifications, which were conducted using reagents and instructions provided by U.S. Biochemicals. The final concentration of magnesium ion was increased to 2.1 mM. Thirty-nine cycles of amplification were performed on a water-cooled vtwb Model 1 cycler (San Diego, Calif.). Amplification parameters included an initial 1 minute denaturation step at 94° C., a 5 minute annealing at 37° C., a 5 minute extension at 65° C., and a 0.3 minute denaturation at 94° C. Approximately 4 µg of each of the degenerate primers (TABLE 1) was included in each amplification. The unusually low annealing temperatures employed in these amplifications may favor polymerase extension from stably-hybridized oligonucleotide primers, resulting in a broader and less-biased amplified population than those obtained with previous protocols (Wilks, Proc. Natl. Acad. Sci. USA, 86:1603–1607, 1989).

TABLE 1

(SEQ ID NOS: 30–35)

| | | | | |
|---|---|---|---|---|
| EXTRACELLULAR | TM | | KINASE:DOMAIN | |

| HRDLAAR | | | | | | DVWSFGV |
|---|---|---|---|---|---|---|
| EGF-R | HRDLAARNVL VKTPQ | HVKITDFGL AKLLG AEEKEYHA | EGGKVPI KWMALESI | LHRI YTHQSDVWSYGV |
| INS-R | HRDLAARNCMVAHDF | TVKIGDFGMTRDI YETDYYRKG | GKGLLP VRWMAPESL | KDGVFTTS SDMWSFGV |
| PDGF-R | HRDLAARNVL I CEGK | LVKICDFGL ARDI MRDSNYI SK | GSTYLPLKWMAPESI | FNSLYTTLSDVWSFGI |
| FGF-R | HRDLAARNVL VTEDN | VMKIADFGL ARDI HHI DYYKKT | TNGRLP VKWMAPEAL | FDRI YTHQSDMWSYGV |
| CONSENSUS | HRDLAARNVL V | VKI DFGL ARDI   Y | G LP KWMAPES | YT SDVWSFGV |

```
                                                              Y    I
                       H R  D L  A  A  R            D  V   W S F  G  V
OGLIGONUCLEOTIDE              C     CC      A       A       ACA AA     C
PRIMERS        5' GGAATTCCATCGNGATTTNGCNGCNCG 3'   3' CTGCANACCTGGATGCCNTAGAGCTCC 5'
```

Amplified DNAs were size fractionated on 5% non-denaturing acrylamide gels. The gels were stained with ethidium bromide (1 µg/ml) and amplified bands of ~220 bp were excised. These bands were eluted overnight into 0.5M ammonium acetate. 1 mM EDTA, 0.2% SDS, and eluted DNA was then precipitated with 10 µg of tRNA carrier. Recovered PCR products were blunt-ended using T4 DNA polymerase, and phosphorylated using T4 polynucleotide kinase. Approximately 40 ng of insert was then ligated with 200 ng of dephosphorylated SmaI/EcoRV-digested pBluescript plasmid. One-tenth of each ligation was used to transform MC1061 bacteria.

The DNA sequence of both strands of each PCR product subclone was determined from alkaline lysis miniprep DNA, using the dideoxy chain termination method. In those cases in which clones having apparently identical inserts were isolated multiple times, the sequence of complementary strands was derived from independent clones.

EXAMPLE 2

SEQUENCE ANALYSIS OF PCR SUBCLONES

Sequence analysis of 168 PCR product subclone yielded 155 with significant similarity to the tyrosine kinase family. TABLE 2 lists the 27 distinct kinase domain sequences contained in this set, which includes those of the abl (human; Shtivelman, et al., Cell, 47:277–284, 1986) arg (human: Kruh, et al., Science, 234:1545–1548, 1986), and fer cytoplasmic (nonreceptor) kinases (human, Hao, et al., Mol. Cell. Biol., 9:1587–1593, 1989), as well as those of the receptors for EGF-R (human; Ullrich, et al., Nature 309, 418–425, 1984), PDGF-A (human; Matsui, et al., Science, 243:800–804, 1989; rat; Lee, et al., Science, 245:57–60, 1989; Reid, et al., Proc. Natl. Acad. Sci. USA, 87:1596–1600, 1990; Safran, et al., Oncogene, 5:635–643, 1990), colony-stimulating factor 1 (CSF-1; human; Coussens, et al., Nature, 320:277–280, 1986; mouse; Rothwell and Rohrschneider, Oncogene Res., 1:311–324, 1987, and insulin-like growth factor 1 (IGF-1; human; Ullrich, et al., EMBO, J., 5:2503–2512, 1986).

Other domain sequences listed include fes (human; Roebroek, et al., EMBO J., 4:2897–2903, 1985); Dsrc (Drosophila; Gregory, et al., Mol. Cell. Biol., 7:2119–2127, 1987); eph (human; Hirai, et al., Science, 238:1717–1720, 1987; eck (human; Lindberg and Hunter, Mol. Cell. Biol., in press, 1990); elk (rat; Letwin, et al., Oncogene, 3:621–627, 1988); neu (Bargmann, et al., Nature, 319:226–230, 1986); bek (mouse; Kombluth, et al., Mol. Cell. Biol., 8:5541–5544, 1988); fit (human; Shibuya, et al., Oncogene, 5:519–524, 1990); trk, (human; Martin-Zanca, et al., Nature, 319:743–748, 1986), and trk B (mouse; Klein, et al., EMBO J., 8:3701–3709, 1989).

Amino acid sequences were deduced from the nucleotide sequence of the 27 different PTK domain cDNAs. Deduced amino acid sequences corresponding to the oligonucleotide primers used for PCR amplification were not included. Kinase domain sequences are segmented according to the subdomains defined by Hanks, et al. (Science, 241:42–52, 1988). After each sequence is a number indicating the number of times it was identified. Numbers listed parenthetically correspond to clones uniquely obtained from amplification of the BD substrate. The segregation of kinase domain subfamilies is based solely on amino acid sequence conservation; sequences denoted by an asterisk were not encountered in this survey but have been included to facilitate comparisons.

The high percentage of isolates encoding tyrosine kinases (92%) and the large number of different kinase clones obtained probably reflect the highly degenerate primers and low temperature annealing and extension parameters used for PCR amplification, as well as the stringent size criteria used in the subcloning and sequencing of PCR products.

Of the 27 different kinases identified in this nervous system survey, 11 (tyro-1 through tyro-8 and tyro-10 through tyro-12) are novel. For the previously identified kinases, several rat isolates differ by 1 or 2 amino acids from the kinase domain sequences reported for other species. Nucleotide sequence comparisons suggest that these differences are accounted for by species variation and do not represent the amplification of novel kinase cDNAs. The novel isolates tyro-1 and tyro-11 were each obtained only a single time.

The kinase domain sequences of tyro-1 through tyro-13 have been grouped by similarity to the equivalent sequences of other PTKs (TABLE 2). The indicated subfamilies were defined with reference to a computer-generated phylogenetic tree, constructed from an analysis of 13 novel partial PTK sequences along with a set of 55 additional PTKs, according to the methods of Fitch and Margoliash (Science, 15:279–284, 1967) as implemented by the programs of Feng and Doolittle (J. Mol. Evol., 25:351–360, 1987). The resulting closely related sequence clusters were used to organize the kinase subfamilies presented in TABLE 2. Tyro-1 and tyro-4, for example, are related to the epithelial cell kinase (eck) (Lindberg and Hunter, Mol. Cell. Biol., in press, 1990), tyro-2 to the EGF receptor and the neu proto-oncogene (Bargmann, et al., Nature, 319:226–230, 1986), tyro-5, tyro-6, and tyro-11 to the elk kinase (Letwin, et al., Oncogene, 3:621–627, 1988), tyro-9 to the bFGF receptor, and tyro-10 to trk and trkB (Martin-Zanca, et al., Nature, 319:743–748, 1986; Klein, et al., EMBO J., 8:3701–3709, 1989). Although they exhibit similarity to the insulin receptor, tyro-3, tyro-7, and tyro-12 are listed as a novel subfamily since they are more closely related to each other than to any previously described kinase. The eck- and elk-related sequences are listed in separate subsets, but it is important to note the high degree of similarity between these subfamilies. The sequences of fes, trk, trkB, and Dsrc28 (each marked with an asterisk) are included in TABLE 2 only for comparison, since they were not encountered in these cloning studios.

EXAMPLE 3

TISSUE EXPRESSION PROFILE OF NOVEL PTK mRNAs

The expression pattern of the 13 novel kinase clones were characterized by first examining the relative levels of mRNA present in a variety of neonatal and adult rat tissues. Radiolabeled cDNA probes for each of these clones, as well as probes prepared from isolates of the bFGF receptor, bek, and elk kinases, were hybridized to a set of eight parallel Northern blots containing RNA isolated from kidney, liver, spleen, heart, skeletal muscle, brain, sciatic nerve, and cultured Schwann cells. RNA was isolated from Schwann cells cultured in both the presence and absence of the adenylate cyclase activator forskolin, since at least one receptor PTK gene (that encoding the PDGF-B receptor) exhibits ell-specific cAMP induction in these cells (Weinmaster and Lemke, EMBO J., 9:915–920, 1990) individual blots were in some cases reutilized for as many as four rounds of hybridization.

Total RNA from various tissues was prepared by the method of Chomczynski and Sacchi (Anal. Biochem., 162:156–159, 1987). One additional phenol-chloroform extraction was performed prior to nucleic acid precipitation. Poly(A)-selected RNA samples were purified by either column chromatography or in batch using oligo(dT)-cellulose type III (Collaborative Research). RNA samples were denatured in 50% formamide, 2.2M formaldehyde, and MOPS at 65° C. for 10 min, electrophoresed in 1.0% agarose, 2.2M formaldehyde, and MOPS, transferred to Nytran filters (Schleicher & Schuell) and baked at 80° C. for 2 hr as previously described (Monuki, et al., Neuron, 3:783–793, 1989). Probes for blot hybridizations were prepared using [$\alpha$-$^{32}$P] dCTP and a random hexamer priming kit, according to instructions provided by the manufacturer (Bethesda Research Laboratories). In all cases, final wash stringency for Northern blots was set at 0.2×SSC, 0.2% SDS, 65° C.

In situ hybridization was performed according to Simmons, et al. (J. Histotechnology, 12:169–181, 1989), with minor modifications. Paraformaldehyde-fixed brain sections (30 μm), from either adult or 33-day-old rats were used. Antisense probes from PCR product subclone were prepared using 125 μCi or [$^{35}$S] UTP (1250 Ci/mmol: New England Nuclear) in a 10 μl transcription reaction, with reagents obtained from Stratagene (La Jolla, Calif.). Hybridizations were performed at 55° C. for 22 hr using approximately 75 μl or 5×10$^6$ cpm/ml probe per slide. RNAase A digestions were performed in buffer prewarmed to 37° C. The final wash stringency was 0.1×SSC at 60° C. for 35 min. Emulsion-dipped slides were exposed for 2 weeks prior to developing. Slides were counterstained with thionin.

Figure 1B:
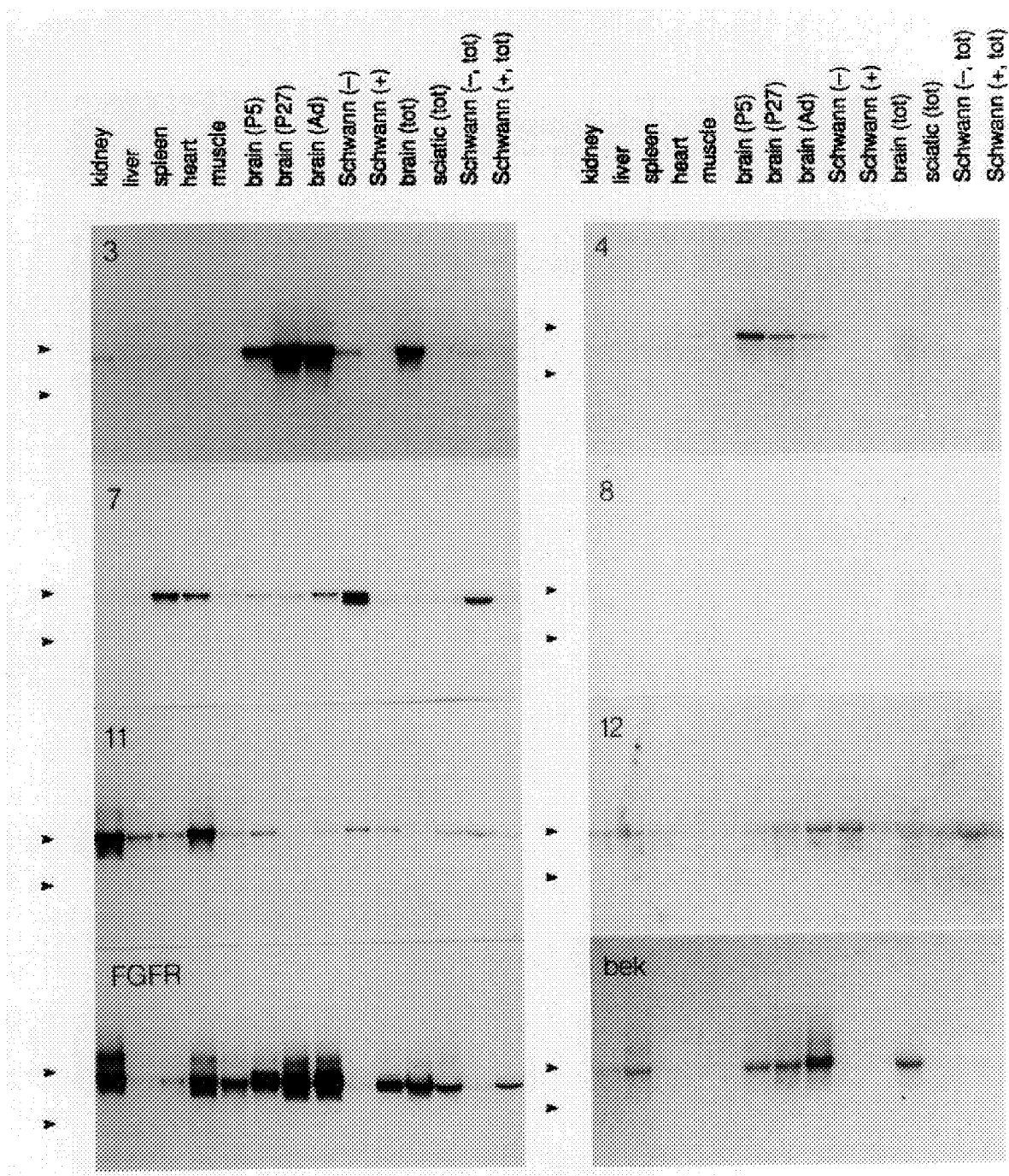

The various tissue expression profiles are shown in FIG. 1. Poly(A) (left 10 lanes) or total RNA (tot, right 4 lanes) from the indicated rat tissues was analyzed for expression of PTK mRNAs. All tissues were taken from animals 27 days postnatal, except where otherwise indicated. Sciatic nerves (sciatic) were obtained from 7-to-8-day-old rats. Rat Schwann cells were cultured in either the presence (+) or absence (−) of 20 μM forskolin for 48 hr prior to harvesting. All lanes contain either 2.5 μg of poly(A)$^+$ RNA or 10 μg of total RNA, except for the cultured Schwann cell poly(A)$^+$ lanes, which contain 1.0 μg each. The relative migration of 18S and 28S ribosomal RNAs, as determined by methylene blue staining, is indicated by the arrowheads. Filters 1–13 show hybridization with $^{32}$P radiolabeled cDNA probes to tyro-1 through tyro-13. Also shown for comparison is the hybridization observed using isolates of elk, the bFGF receptor (FGFR), and the bek FGF receptor.

Exposure times were as follows: 34 hr (1, 5, 6, 7, 11), 41 hr (3, 4, FGFR), 120 hr (2, 9, 10, bek), 158 hr (8, 13, elk), 8 days (12).

The results of this analysis (FIG. 1) demonstrate that 6 of the 11 novel kinase genes (tyro-1 through tyro-6), together with the elk gene, are preferentially expressed by cells of the nervous system. For example, tyro-1, a novel member of the eck kinase subfamily, exhibited strong hybridization to brain mRNA, a faint signal in Schwann cells, and very faint signals in kidney and heart. Tyro-4 also a novel member of the eck subfamily, exhibited more modest hybridization to two mRNAs in postnatal day 5(P5) brain, with lower signals evident in older brains as well as kidney and heart. The novel EGF receptor homolog tyro-2 identified a high molecular weight mRNA in brain that could also be detected in kidney and heart. It is possible that the very low tyro-1, tyro-2, and tyro-4 hybridization signals observed in kidney and heart are due to neural contamination from the adrenal gland and cardiac ganglia, respectively. Tyro-3, a member of the novel kinase subfamily with similarity to the insulin receptor, showed intense hybridization to brain mRNA, with very faint signals in perhaps all other tissues.

Members of the same receptor-configured kinase subfamily occasionally exhibited very different patterns of expression. Within the elk subfamily, for example, elk itself and the related kinases tyro-5 and tyro-6 were exclusively or predominantly expressed in neural tissues, elk strongly hybridized to two mRNA species in brain and Schwann cells, tyro-5 exhibited strong hybridization to P5 brain mRNA with reduced signals present in later stage brains and in Schwann cells, and tyro-6 gave a strong hybridization signal in cultured Schwann cells, weaker signals in brain, and very faint but detectable signals in other tissues. In contrast, expression of the elk-related kinase tyro-11 was predominant in heart and kidney, but expressed at lower levels in neural tissue. The distinct hybridization patterns observed between members of this closely related subfamily indicate that despite significant similarity at the nucleotide level, cross-hybridization is not readily detected when hybridizations are carried out at high stringency. Tyro-5 and tyro-6, the most closely related of the PTK domains we analyzed, exhibit 84.2% nucleotide identity over the kinase domain, but their hybridization profiles can be readily distinguished (FIG. 1, compare profiles 5 and 6).

Among those kinases not restricted to neural cells, tyro-9, a member of the FGF receptor subfamily, exhibited a pattern of expression that was distinct from that of either the bFGF receptor or bek. Most strongly expressed in kidney and liver, it exhibited only weak hybridization signals with brain mRNA. At two extremes of expression, tyro-12 yielded weak hybridization signals in all tissues, with expression being somewhat lower in heart and muscle, but, tyro-8 (distantly related to Dsrc28) yielded only an extremely faint signal in spleen and heart.

Schwann cell expression of certain kinase genes was strongly regulated by cAMP (FIG. 1). As for the PDGF receptor gene (Weinmaster and Lemke, *EMBO J.*, 9:915–920, 1990), expression of the elk and FGF receptor genes was significantly up-regulated by 48 hr treatment with forskolin. Since cAMP induction of the PDGF receptor appears to account for the synergistic effect on Schwann cell proliferation achieved with combined application of PDGF and forskolin (Weinmaster and Lemke, *EMBO J.*, 9:915–920, 1990), cAMP induction of the FGF receptor may also explain the similar synergistic effect observed for the combination of FGF and forskolin (Davis and Stroobant, *J. Cell Biol.*, 110:1353–1360, 1990). Importantly, cAMP induction was not observed for most of the receptor PTKs expressed by Schwann cells; the tyro-1, tyro-3, tyro-6, tyro-7, tyro-12, and tyro-13 mRNAs were down-regulated in the presence of forskolin, and expression of the tyro-5 and tyro-11 genes was not affected by the drug.

Several receptor PTKs exhibited relatively modest signals in sciatic nerve compared with cultured Schwann cells or other tissues. This is probably a function of both the cellular heterogeneity of the nerve, which contains a substantial number of fibroblasts and endothelial cells, and the great sensitivity of PCR amplification.

EXAMPLE 4

DEVELOPMENTAL EXPRESSION PROFILE OF NEURAL PTK mRNAs

Figure 2:
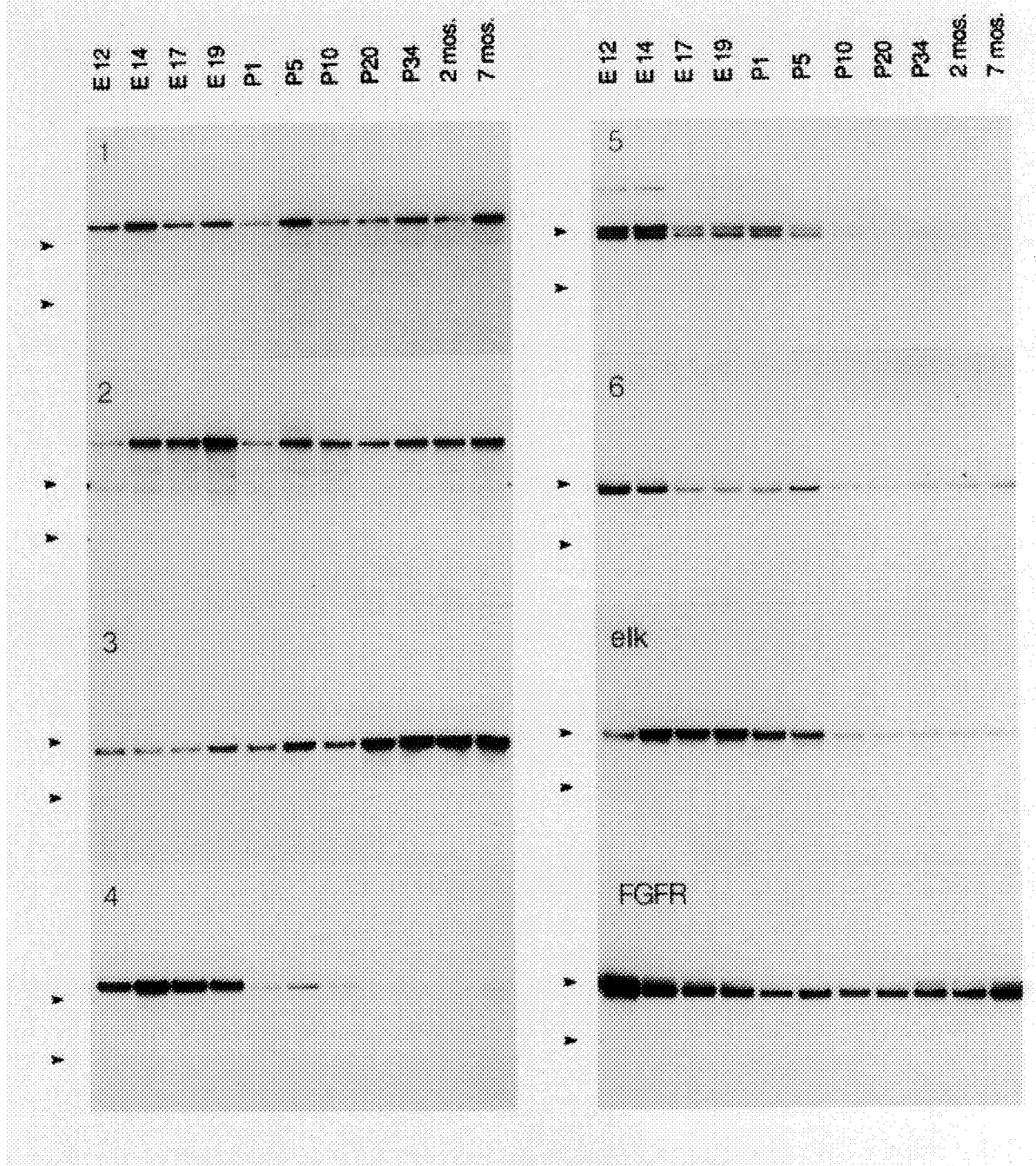
FIG. 2 shows the developmental tissue profiles of the novel PTK mRNAs which were predominantly or exclusively neural in their distribution.

Since many of the determinative events in mammalian neural development occur near the midpoint of embryogenesis, a study was performed to determine whether any of the novel neural kinase genes were expressed embryonically. To assess their developmental expression, a set of Northern blots containing mRNA isolated from the brains of rats ranging in age from embryonic day 12 (E12) to adult were probed. For comparison, included were the bFGF receptor and elk in this survey, the results of which are presented in FIG. 2. For each of the novel kinase genes, expression was observed in the developing central nervous system at E12, a time at which multiple influences on both neural cell proliferation and differentiation are known to be exercised.

Poly(A)$^+$ RNA (2 μg) from rat brains obtained from animals of the indicated ages (E12 to 7 months postnatal) was analyzed for the expression of PTK mRNAs. Filters 1–6 show hybridization obtained with $^{32}$P-radiolabled cDNA probes to tyro-1 through tyro-6. Also shown are the hybridization profiles obtained using isolates of elk and the bFGF receptor (FGFR). The relative migration of 18S and 28S ribosomal RNAs, as determined by methylene blue staining, is indicated by the arrowheads. Exposure times are as follows: 15 hr (1, 3, 5, elk, FGFR), 22 hr (4, 6), 50 hr (2).

Although detected in adult brain, three of the novel kinase genes were maximally expressed embryonically. mRNA encoding the elk-related kinase tyro-6, for example, was most abundantly expressed at E12; expression gradually fell until P10 and was relatively constant thereafter. Similarly, mRNA encoding the closely related kinase tyro-5 was maximally expressed at E14; expression fell sharply after P5 to a much lower steady-state level in the adult brain. The gene encoding the eck- related kinase tyro-4 exhibited a similar, though even more dramatic regulation, with a peak in expression at E14/17, a sharp drop at birth, and a low steady-state level after P10.

In contrast to the pronounced drop in expression for tyro4 and tyro-5, expression of mRNA encoding the eck-like kinase tyro-1, while exhibiting some temporal fluctuation, was relatively constant throughout neural development. A similar, though less variable-developmental profile, was observed for mRNA encoding the bFGF receptor. Although maximal expression was observed at E12, bFGF receptor mRNA levels fell only modestly during the course of brain development and remained high in adult animals. Of the novel kinase genes analyzed in FIG. 2, only tyro-3 exhibited a significant increase in expression during late neural development, with appreciably higher mRNA levels (relative to E12) evident after P20.

EXAMPLE 5

IN SITU LOCALIZATION OF NOVEL PTK TRANSCRIPTS IN BRAIN

To determine whether any of the novel neural kinases exhibited cell type-restricted expression in the vertebrate central nervous system, radiolabeled antisense RNA probes for each of the clones were prepared and these probes hybridized in situ to 30 μm brain sections prepared from 33-day-old and adult male rats. For comparison, antisense probes prepared from our isolates of the bFGF receptor and the related FGF receptor bek were included.

Although the profiles of these brain sections represented a selective sampling of the brain, they nonetheless demonstrated that expression of each of the novel neural kinases is highly regionalized. Tyro-1 mRNA was the most widely expressed in adult brain. Tyro-1 probes exhibited exceptionally strong and continuous hybridization in all fields of the hippocampus and the dentate gyrus and throughout the neocortex, with a diffuse band present in layer 3. Strong hybridization was also seen in the Purkinje cell layer, the inferior olive, and lateral nucleus of the cerebellum, but not in the cerebellar granule cell layers.

In contrast, the tyro-2 gene exhibited a much more restricted pattern of expression. Hybridization was again evident throughout all fields of the hippocampus and the dentate gyrus, but signals were restricted to occasional (~1 in 10) cells. This striking, punctate pattern of hippocampal hybridization was not seen for any other PTK gene. A similarly restricted pattern of tyro-2 hybridization was also observed throughout the neocortex. Stronger and more continuous hybridization was evident in the medial habenula and in the reticular nucleus of the thalamus, but in contrast to tyro-1, no signal above background was observed in the remainder of the thalamus. The strongest tyro-2 hybridization signal in the brain was observed in an intercalated nucleus of the amygdala. No signal was evident in the Purkinje cell layer in the cerebellum. The hybridization pattern have observed for tyro-2 is largely consistent with its expression by a subset of 7-amino-n-butyric acid (GABA) -ergic neurons.

In situ hybridization signals corresponding to tyro-3 mRNA presented an equally striking pattern. In the hippocampus, strong hybridization was observed in the CA1 field. However, upon crossing the border from CA1 to the shorter CA2 field an abrupt drop in the tyro-3 hybridization signal was observed. The tyro-3 signal remained much reduced in CA3 (relative to CA1), and no signal at all in the dentate gyrus was observed. Tyro-3 therefore provides an excellent molecular marker for the CA1/CA2 transition, previously defined on the basis of hippocampal cell size and circuitry. Robust tyro-3 hybridization was also evident in large cells throughout neocortex, with the strongest signals being observed in deeper layers. In the cerebellum, strong hybridization was observed to granule cells, but not to Purkinje cells, a pattern that was the opposite of that observed for tyro-1.

Consistent with their developmental expression profiles, tyro4, tyro-5, and tyro-6 exhibited the most restricted patterns of expression in adult brain. Distinct hybridization to tyro-4 was evident in the facial nucleus of the pons, with more modest signals present in the bed nucleus of the anterior commissure and the triangular nucleus of the septum. The tyro-5 gene was expressed weakly in cortex, at a modest level in all fields of the hippocampus, and in a subset of Purkinje cells in the cerebellum. The tyro-6 gene showed a similar pattern of expression, giving a signal in Purkinje cells and weak signals in the hippocampus.

The two FGF receptor genes examined, those encoding the bFGF receptor and bek, exhibited very different patterns of expression in the brain. mRNA encoding the bFGF receptor was expressed at high levels in hippocampal neurons, but exhibited a field distribution that was nearly the inverse of tyro-3., i.e., expression was reduced in CA1 relative to CA2 and CA3. mRNA levels in the dentate gyrus were lowest of all. The expression of bFGF receptor mRNA in the choroid plexus and in the central nucleus of the amygdala and in a narrow band of cells in layer 6 of neocortex, a region not seen in the previous work of Wanaka, et al. (*Neuron,* 5:267–281, 1990) was also observed. In contrast, expression of bek mRNA was largely confined to non-neuronal cells. High level expression was observed in the choroid plexus, and in the white matter glia of the cerebellum and the pons. Diffusely localized hybridization to a layer of cells that may be Bergmann glia was also apparent in the cerebellum. The cerebellar expression pattern of bek was clearly distinct from the patterns observed for tyro-5 and tyro6, which marked Purkinje cells, but exhibited no hybridization to white matter glia.

TABLE 2

(Seq. ID Nos: 36–54)

| KINASE | | DEDUCED AMINO ACID SEQUENCES FOR PUTATIVE TYROSINE KINASES | | | | |
|--------|------------|-----------|------------------------|------------------|------------|-----------|
| SUB-FAMILY | | VI | VII | VIII | IX | INCIDENCE |
| abl | abl | NCLVGENH | LVKVADFGLSRLMTGDTYTAH | AGAKFPIKWTAPESL | AYNKESIXS | 6 |
| | arg | NCLVGENH | VVKVADFGLSRLMTGDIYTAH | AGAKFPIKWTAPESL | AYNTFSIKS | 3 |
| | fes/fps* | NCLVTEKM | VLKISDFGMSREEADGVYAASG | GLRQVPVKWTAPEAL | NYGRYSSES | |
| | fer | NCLVGENM | TLKISDFGMSRQEDGGVYSSS | GLKOIPIKWTAPEAL | NYGRYSSES | 2 |
| src | Dsrc28* | NCLVGSEN | VVKVADFGLABYVLDDQYTSSG | GRKFPIXWAPPEVL | NYTRFSSKS | |

TABLE 2-continued (Seq. ID Nos: 36–54)

| KINASE SUB-FAMILY | | DEDUCED AMINO ACID SEQUENCES FOR PUTATIVE TYROSINE KINASES | | | | INCIDENCE |
|---|---|---|---|---|---|---|
| | | VI | VII | VIII | IX | |
| | tyro-8 | NCLVDSOL | SVKVSDFGMTRYVLDDQYVSSV | GTKFPVKWSAPEVF | NYFKTSSKS | 2 |
| tyro-13 | tyro-13 | NVLVSEDN | VAKVSDFGLTXEASSTQ | DTGXLPVKWTAPEAL | REKKTSTXS | 11 |
| epb/eck/elk | eph* | NILVNQNL | CCKVSDFGLTRLL DDFDGTYET | OGGKIPIRWTAPEAI | AHRIFTTAS | |
| | eck | NILVNSNL | VCKVSDFGLSRVLEDDPEATYTT | SGGKIPIRNTAPEAI | SYRKFTSAS | 5 |
| | tyro-1 | NILVNSNL | VCKVSDFGMSRVLEDDPEAAYTT | RGGKEPIRWTAPEAI | AYRKETSAS | 1 |
| | tyro-4 | NILINSNL | VCKVSDFGLSRVLEDDPEAAYTT | RGGKIPIRWTSPEAI | AYRKFTSAS | 4 |
| | elk | NILVNSNL | VCKVSDFGLSRYLQDOTSDPTYTSS | LGGKIPVRWTAPEAI | AYRKFTSAS | 1 |
| | tyro-5 | NILVNSNL | VCKVSDFGLSRFLEDDTSDPTYTSA | LGGKIPIRWTAPEAI | QYRKFTSAS | (3) |
| | tyro-6 | NILVNSNL | VCKVSDFGLSRFLEDDPSDPTYTSS | LGGKIPIRWTAPEAI | AYRKFISAS | 3 |
| | tyro-11 | NILVNSNL | VCKVSDEGLBRFLEENSSDPTYTSS | LGGKIPIRNTAPEAI | ATRKFTSAS | (1) |
| EGF-R | EGF-R | NVLVKIPO | NVXITDFGLAXLIGAEEKEYHA | EGGKVPIKWMALESI | LHRIYTHOS | 3 |
| | neu | NVLVKSPN | HVXITDFGLARLIDIDETEYHA | DGGKVPIKWMALESI | LRRRFTHOS | 10 |
| | tyro-2 | NVLVKSPN | KVXITDFGLARLLEGDEXEYNA | DGGKMPIKWMALECI | HYRNFTHOS | 8 |
| FGF-R | bFGF-R | NVLVTEDN | VMKIADFGLARDIHHIDYYKKT | TNGRLPVKWMAPEAL | FDRIYTHOS | 4 |
| | bek | NVLVTENN | VMKIADFGLARDINNIDYYKKT | TNGRLPVKWMAPEAL | FDRVYTHOS | 2 |
| | tyro-9 | NVLVTEDD | VMKIADFGLARGVKKIDYYKKT | SNGRLPVKWMAPEAL | FDRVYTHOS | 1 |
| PDGF-R | PDGF-A R | NVLLAQGK | IVKICDFGLARDIMHDSNYVSK | GSTFLPVXWMAPESI | FONLYTTLS | 3 |
| | PDGF-B R | NMLICEGK | LVKICDFGLARDIMRDSNYISK | GSTFLPLKWMAPESI | FNSLYTTLS | 1 |
| | CSF-1 R | NVLLTSGH | VAKIGDFGLARDIMNDSNYVVK | GNARLPVKWMAPESI | FDCVXTVQS | 20 |
| | flt | NILLSENN | VVKICDFGLARDIYKNPDYVRR | GDTRLPLKWMAPESI | RDKVYSTXS | 5 |
| tyro-3 | tyro-3 | NCMLAEDM | TVCVADEGLSRKIYSGDYYRQG | CASKLPVKWLAIESL | ADSLYTVBS | 3 |
| | tyro-7 | NCMLNENM | SVCVADFGLSXKIYNGDYYRQG | PEAKMPVKWIAIESL | ADRVYTSMS | 4 |
| | tyro-12 | NCMLRDDM | TVCVADFGLSXKIYSGDYYRQG | RIAKMPVKWIAIESL | ADRVYTSKS | (3) |
| Insulin-R | trk* | NCLVGQGL | VVKIGDFGMSRDIYSTDYYRVG | GRTNLPIRWMPPESI | LYRKETTES | |
| | trkS* | NCLVGENL | LVXIGDFGMSRDVYSTDYYRVG | GRTNLPIRWMPPESI | MYRKETTES | |
| | IGEIR | NGMVAEDF | TVKIGDFGMSRDVYSTDYYRVG | GRTNLPIRWMPPESI | MYRKETTES | 2 |
| | tyro-IO | NCLVGKNY | TIKIADFGMSRNLYSGDYYRIQ | GRAVLPIRWMSWESI | LLGKETTAS | (6) |

The foregoing is meant to illustrate, but not to limit, the scope of the invention. Indeed, those of ordinary skill in the art can readily envision and produce further embodiments, based on the teachings herein, without undue experimentation.

We claim:
1. An isolated tyro-3 polypeptide.
2. The polypeptide of claim 1, wherein the polypeptide is encoded by a polynucleotide as set forth in SEQ ID NO:5.
3. The polypeptide of claim 1, having an amino acid sequence as set forth in SEQ ID NO:6.
4. The polypeptide of claim 1, wherein the polypeptide is expressed in brain tissue.

* * * * *